(12) United States Patent
Zhong et al.

(10) Patent No.: US 10,723,768 B2
(45) Date of Patent: *Jul. 28, 2020

(54) CAPSID MODIFIED RAAV VECTORS AND METHODS OF USE

(71) Applicant: University of Florida Research Foundation, Incorporated, Gainesville, FL (US)

(72) Inventors: Li Zhong, Gainesville, FL (US); Sergei Zolotukhin, Gainesville, FL (US); Lakshmanan Govindasamy, Gainesville, FL (US); Mavis Agbandje-McKenna, Gainesville, FL (US); Arun Srivastava, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/680,668

(22) Filed: Aug. 18, 2017

(65) Prior Publication Data

US 2018/0036428 A1 Feb. 8, 2018

Related U.S. Application Data

(63) Continuation of application No. 14/847,528, filed on Sep. 8, 2015, now Pat. No. 9,775,918, which is a continuation of application No. 13/855,640, filed on Apr. 2, 2013, now Pat. No. 9,157,098, which is a continuation of application No. 12/595,196, filed as application No. PCT/US2008/059647 on Apr. 8, 2008, now Pat. No. 8,445,267.

(60) Provisional application No. 60/910,798, filed on Apr. 9, 2007.

(51) Int. Cl.
| | |
|---|---|
| *C07K 14/005* | (2006.01) |
| *C12N 15/86* | (2006.01) |
| *A61K 48/00* | (2006.01) |
| *A61K 39/00* | (2006.01) |
| *C12N 15/864* | (2006.01) |
| *A61K 35/76* | (2015.01) |
| *C12N 7/00* | (2006.01) |

(52) U.S. Cl.
CPC .......... *C07K 14/005* (2013.01); *A61K 35/76* (2013.01); *A61K 39/0011* (2013.01); *A61K 48/005* (2013.01); *A61K 48/0008* (2013.01); *A61K 48/0091* (2013.01); *C12N 7/00* (2013.01); *C12N 15/86* (2013.01); *C12N 15/8645* (2013.01); *A61K 2039/5158* (2013.01); *C12N 2750/14122* (2013.01); *C12N 2750/14132* (2013.01); *C12N 2750/14142* (2013.01); *C12N 2750/14143* (2013.01); *C12N 2750/14145* (2013.01); *C12N 2750/14171* (2013.01); *C12N 2810/6027* (2013.01)

(58) Field of Classification Search
None
See application file for complete search history.

(56) References Cited

U.S. PATENT DOCUMENTS

| | | | |
|---|---|---|---|
| 6,156,303 A | 12/2000 | Russell et al. | |
| 7,052,692 B1 | 5/2006 | Srivastava et al. | |
| 8,445,267 B2 | 5/2013 | Zhong et al. | |
| 8,802,440 B2 | 8/2014 | Zhong et al. | |
| 9,157,098 B2 | 10/2015 | Zhong et al. | |
| 9,611,302 B2 | 4/2017 | Srivastava et al. | |
| 9,725,485 B2 | 8/2017 | Srivastava et al. | |
| 9,775,918 B2 | 10/2017 | Zhong et al. | |
| 9,920,097 B2 | 3/2018 | Zhong et al. | |
| 10,011,640 B2 | 7/2018 | Srivastava et al. | |
| 10,294,281 B2 | 5/2019 | Srivastava et al. | |
| 2003/0138772 A1 | 7/2003 | Gao et al. | |
| 2003/0219733 A1 | 11/2003 | Clark et al. | |
| 2006/0292117 A1 | 12/2006 | Loiler et al. | |
| 2010/0104561 A1 | 4/2010 | Zhong et al. | |
| 2013/0203841 A1 | 8/2013 | Zhong et al. | |
| 2013/0216501 A1 | 8/2013 | Zhong et al. | |
| 2013/0224836 A1 | 8/2013 | Muramatsu | |
| 2013/0310443 A1 | 11/2013 | Srivastava et al. | |
| 2014/0050701 A1 | 2/2014 | Zhong et al. | |
| 2014/0341852 A1 | 11/2014 | Srivastava et al. | |
| 2015/0133530 A1 | 5/2015 | Srivastava et al. | |
| 2016/0106865 A1 | 4/2016 | Zhong et al. | |
| 2016/0333372 A1 | 11/2016 | Srivastava et al. | |
| 2016/0361439 A1 | 12/2016 | Agbandje-Mckenna et al. | |

(Continued)

FOREIGN PATENT DOCUMENTS

| | | |
|---|---|---|
| CA | 2826273 A1 | 8/2012 |
| CN | 102159713 A | 8/2011 |

(Continued)

OTHER PUBLICATIONS

US 10,221,219 B2, 03/2019, Srivastava et al. (withdrawn)

(Continued)

*Primary Examiner* — Nancy A Treptow
(74) *Attorney, Agent, or Firm* — Wolf, Greenfield & Sacks, P.C.

(57) ABSTRACT

Disclosed are tyrosine-modified rAAV vectors, as well as infectious virions, compositions, and pharmaceutical formulations that comprise them. Also disclosed are methods of preparing and methods for using the disclosed tyrosine-phosphorylated capsid protein mutant rAAV vectors in a variety of diagnostic and therapeutic applications including in vivo and ex vivo gene therapy, and large-scale production of rAAV vectors.

31 Claims, 22 Drawing Sheets

Specification includes a Sequence Listing.

(56) References Cited

U.S. PATENT DOCUMENTS

| | | |
|---|---|---|
| 2016/0369299 A1 | 12/2016 | Boye et al. |
| 2017/0275337 A1 | 9/2017 | Srivastava et al. |
| 2018/0030096 A1 | 2/2018 | Aslanidi et al. |
| 2018/0105559 A1 | 4/2018 | Zhong et al. |
| 2018/0135074 A1 | 5/2018 | Srivastava et al. |
| 2018/0223312 A1 | 8/2018 | Srivastava et al. |
| 2018/0244727 A1 | 8/2018 | Zhong et al. |
| 2019/0000943 A1 | 1/2019 | Aslanidi |
| 2019/0016759 A1 | 1/2019 | Srivastava et al. |
| 2019/0127424 A1 | 5/2019 | Srivastava et al. |
| 2019/0284244 A1 | 9/2019 | Srivastava et al. |

FOREIGN PATENT DOCUMENTS

| | | |
|---|---|---|
| CN | 102994549 A | 3/2013 |
| CN | 103060331 A | 4/2013 |
| CN | 104470945 A | 3/2015 |
| EP | 1310571 A2 | 5/2003 |
| EP | 1 486 567 A1 | 12/2004 |
| EP | 2 660 325 A2 | 11/2013 |
| WO | WO 03/006616 A2 | 1/2003 |
| WO | WO 03/052052 A2 | 6/2003 |
| WO | WO 2004/027019 A2 | 4/2004 |
| WO | WO 2004/111248 A2 | 12/2004 |
| WO | WO 2005/033321 A2 | 4/2005 |
| WO | WO 2006/110689 A2 | 10/2006 |
| WO | WO 2006/119150 A2 | 11/2006 |
| WO | WO 2008/124724 A1 | 10/2008 |
| WO | WO 2008/145400 A2 | 12/2008 |
| WO | WO 2011/133890 | 10/2011 |
| WO | WO 2012/057363 A2 | 5/2012 |
| WO | WO 2013/158879 A1 | 10/2013 |

OTHER PUBLICATIONS

EP Examination Report dated Jan. 27, 2011, issued in EP 08733161.7-2405 (3 pages).

Response to EP Examination Report dated Jul. 25, 2011, issued in EP 08733161.7-2405 (8 pages).

Examination Report dated Oct. 22, 2013, issued in CIPO 2,720,097 (2 pages).

International Preliminary Report on Patentability for Application No. PCT/US2008/059647 dated Oct. 13, 2009.

International Search Report and Written Opinion for Application No. PCT/US2008/059647 dated Sep. 10, 2008.

International Search Report and Written Opinion for Application No. PCT/US2013/041234 dated Feb. 13, 2014.

International Preliminary Report on Patentability for Application No. PCT/US2013/041234 dated Nov. 27, 2014.

International Search Report and Written Opinion for Application No. PCT/US2014/039015 dated Nov. 24, 2014.

International Preliminary Report on Patentability for Application No. PCT/US2014/039015 dated Dec. 3, 2015.

International Search Report and Written Opinion for Application No. PCT/US2016/016422 dated May 5, 2016.

International Preliminary Report on Patentability for Application No. PCT/US2016/016422 dated Aug. 17, 2017.

Aslanidi, George V. et al, High-Efficiency Transduction of Human Monocyte-Derived Dendritic Cells by Capsid-Modified Recombinant AAV2 Vectors, Vaccine 30:3908-3917 (2012), .COPYRGT. 2012 Elsevier Ltd., pp. 3908-3917.

Aslanidi, George V. et al, Optimization of the Capsid of Recombinant Adeno-Associated Virus 2 (AAV2) Vectors: The Final Threshold?, PLoS ONE 8(3): e59142 (Mar. 2013), 12 pages.

Aslanidi et al., Abstract C240: Modification on the capsid of recombinant adeno-associated virus vectors (rAAV) leads to high-efficiency transduction of human monocyte-derived dendritic cells (moDCs). Mol Cancer Ther. Nov. 10, 2011(11): Abstract C240. 3 Pages.

Bantel-Schaal et al., Human adeno-associated virus type 5 is only distantly related to other known primate helper-dependent parvoviruses. J Virol. Feb. 1999;73(2):939-47.

Cheng, Binbin et al, Development of Optimized AAV3 Serotype Vectors: Mechanism of High-Efficiency Transduction of Human Liver Cancer Cells,Gene Ther. Apr. 2011; 19(4): 375-384, 24 pages.

Chiorini et al., Capsid Protein [Adeno-associated virus—5] GENBANK Accession No. YP-068409 Dec. 8, 2008.

Dalkara, D., et al., Enhanced Gene Delivery to the Neonatal Retina Through Systemic Administration of Tyrosine-Mutated AAV9,. COPYRGT. 2012 Macmillan Publishers Limited (0969-7128/12), www.nature.com/gt, Gene Therapy (2012) 19, pp. 176-181.

Doroudchi, M. Mehdi, et al., Virally Delivered Channeirhodopsin-2 Safely and Effectively Restores Visual Function in Multiple Mouse Models of Blindness, .COPYRGT. The American Society of Gene & Cell Therapy, www.moleculartherapy.org, vol. 19, No. 7, Jul. 2011, pp. 1220-1229.

Gabriel et al., Targeted Mutagenesis of Ubiquitin-Binding Lysine Residues on the Adeno-Associated Virus (AAV)2 Capsid Improves Its Transduction Efficiency. Mol Ther. 2012;20(Supp 1):S146.

Horowitz, Eric D., et al., Tyrosine Cross-Linking Reveals Interfacial Dynamics in Adeno-Associated Viral Capsids During Infection, ACS Chemical Biology, pubs.acs.org/acschemicalbiology, ACS Publications, .COPYRGT. American Chemical Society,dx.doi.org/10.1021/cb3000265, Mar. 29, 2012, pp. A-H.

Jayandharan, Giridhara R. et al., Activation of the NF-kB Pathway by Adeno-Associated Virus (AAV) Vectors and its Implications in Immune Response and Gene Therapy, PNAS, Mar. 1, 2011, vol. 108, No. 9, pp. 3743-3748.

Kauss, M. Ariel, et al., Enhanced Long-Term Transduction and Multilineage Engraftment of Human Hematopoietic Stem Cells Transduced With Tyrosine-Modified Recombinant Adeno-Associated Virus Serotype 2, Human Gene Therapy 21:1129-1136 (Sep. 2010),.COPYRGT. Mary Ann Liebert, Inc., doi: 10.1089/hum.2010.016, pp. 1129-1136.

Kay et al., Targeting photoreceptors via intravitreal delivery using novel, capsid-mutated AAV vectors. PLoS One. Apr. 26, 2013;8(4):e62097. doi: 10.1371/journal.pone.0062097. Print 2013.

Kern et al., Identification of a heparin-binding motif on adeno-associated virus type 2 capsids. J Virol. Oct. 2003;77(20):11072-81.

Ku, Cristy A., et al., Gene Therapy Using Self-Complementary T733F Capsid Mutant AAV2/8 Restores Vision in a Model of Early Onset Leber Congenital Amaurosis, .COPYRGT. The Author 2011, Published by Oxford University Press, Human MolecularGenetics, 2011, doi: 10.1093/hmg/ddr391, pp. 1-13.

Le Meur, G. et al., Restoration of vision in RPE65-deficient Briard dogs using an AAV serotype 4 vector that specifically targets the retinal pigmented epithelium, Gene Therapy 14(4):292-303 (Feb. 2007), 12 pages.

Li et al., Site-Directed Mutagenesis of Surface-Exposed Lysine Residues Leads to Improved Transduction by Recombinant Aav2 and Aav8 Vectors in Murine Hepatocytes in Vivo. Mol Ther. 2013;21(Supp 1):S208-9.

Ling et al, Selective in vivo targeting of human liver tumors by optimized AAV3 vectors in a murine xenograft model. Hum Gene Ther. Dec. 2014;25(12):1023-34. doi: 10.1089/hum.2014.099.

Lochrie, Michael A. et al., Mutations on the External Surfaces of Adeno-Associated Virus Type 2 Capsids That Affect Transduction and Neutralization,Journal of Virology 80(2):821-834 (Jan. 2006), 14 pages.

Locke, Michelle, et al., Transduction of Human Adipose-Derived Mesenchymal Stem Cells by Recombinant Adeno-Associated Virus Vectors, COPYRGT. Mary Ann Liebert, Inc., DOI: 10.1089/ten.tec.2011.0153, Tissue Engineering: Part C; vol. 17, No. 9,2011, pp. 949-959.

Markusic, David M. et al., High-Efficiency Transduction and Correction of Murine Hemophelia B Using AAV2 Vectors Devoid of Multiple Surface-Exposed Tyrosines, Molecular Therapy (Dec. 2010), vol. 18, No. 12, pp. 2048-2056.

Opie et al., Identification of amino acid residues in the capsid proteins of adeno-associated virus type 2 that contribute to heparan sulfate proteoglycan binding. J Virol. Jun. 2003;77(12):6995-7006.

(56) References Cited

OTHER PUBLICATIONS

Pandya et al., Rationally designed capsid and transgene cassette of AAV6 vectors for dendritic cell-based cancer immunotherapy. Immunol Cell Biol. Feb. 2014;92(2):116-23. doi: 10.1038/icb.2013.74. Epub Nov. 12, 2013.
Pang, Ji-Jing, et al., Long-Term Retinal Function and Structure Rescue Using Capsid Mutant AAV8 Vector in the rd10 Mouse, a Model or Recessive Retinitis Pigmentosa,.COPYRGT. The American Society of Gene & Cell Therapy, Molecular Therapy, pp. 1-9,2010.
Petrs-Silva, Hilda, et al., High-Efficiency Transduction of the Mouse Retina by Tyrosine-Mutant AAV Serotype Vectors .COPYRGT. The American Society of Gene & Cell Therapy, www.moleculartherapy. org, Molecular Therapy, vol. 17, No. 3, pp. 463-471,Mar. 2009.
Petrs-Silva, Hilda, et al., Novel Properties of Tyrosine-Mutant AAV2 Vectors in the Mouse Retina, .COPYRGT. The American Society of Gene & Cell Therapy, Molecular Therapy, www. moleculartherapy.org, pp. 1-9, 2010.
Qi, YanFei, et al., Comparison of Transduction Efficiency of Tyrosine-Mutant AAV Serotype Vectors in Kidney, .COPYRGT. 2012 The Authors Clinical and Experimental Pharmacology and Physiology, .COPYRGT. 2012 Wiley Publishing Asia Pty Ltd., doi:10.1111/1440-1681.12037, 8 pages.
Qiao, Chunping, et al., Adeno-Associated Virus Serotype 6 Capsid Tyrosine-to-Phenylalanine Mutations Improve Gene Transfer to Skeletal Muscle, Human Gene Therapy 21:1343-1348 (Oct. 2010), .COPYRGT. Mary Ann Liebert, Inc., doi:10.1089/hum.2010.003, pp. 1343-1348.
Qiao, Chunping, et al., Single Tyrosine Mutation in AAV8 and AAV9 Capsids Is Insufficient to Enhance Gene Delivery to Skeletal Muscle and Heart, Human Gene Therapy Methods: Part B 23:29-37 (Feb. 2012), .COPYRGT. Mary Ann Liebert, Inc., doi:10.1089/hgtb.2011.229, pp. 29-37.
Ruan, Qing, et al., Development of an Anti-Angiogenic Therapeutic Model Combining scAAV2-delivered siRNAs and Noninvasive Photoacoustic Imaging of Tumor Vasculature Development, Cancer Lett. (2012), http://dx.doi.org/10.1016/j.canlet.2012.11.016,Dec. 4, 2012, 10 pages.
Ryals, Renee C., et al., Quantifying Transduction Efficiencies of Unmodified and Tyrosine Capsid Mutant AAV Vectors in Vitro Using Two Ocular Cell Lines, Molecular Vision 2011; 17:1090-1102 (http://www.molvis.org/molvis/v17/a124), Apr. 29, 2011,pp. 1090-1102.
Schaffer et al., GenBank Submission: ADW24587. Apr. 7, 2005.
Shin, Jin-Hong, et al., A Simplified Immune Suppression Scheme Leads to Persistent Micro-Dystrophin Expression in Duchenne Muscular Dystrophy Dogs, Human Gene Therapy 23:202-209 (Feb. 2012), .COPYRGT. Mary Ann Libert, Inc., doi:10.1089/hum.2011,147,pp. 202-209.
Song et al., High-efficiency transduction of primary human hematopoietic stem cells and erythroid lineage-restricted expression by optimized AAV6 serotype vectors in vitro and in a murine xenograft model in vivo. PLoS One. 2013;8(3):e58757. doi: 10.1371/journal.pone.0058757. Epub Mar. 14, 2013.
Ussher, James E., et al., Optimized Transduction of Human Monocyte-Derived Dendritic Cells by Recombinant Adeno-Associated Virus Serotype 6, Human Gene Therapy 21:1675-1686 (Dec. 2010), .COPYRGT. Mary Ann Liebert, Inc., doi: 10.1089/hum.2010.078,pp. 1675-1686.
Vandenberghe et al., B4Y882_9VIRU sequence alignment, Submitted Sep. 23, 2008.
Vandenberghe et al., Naturally occurring singleton residues in AAV capsid impact performance and illustrate structural constraints. Submitted 2007. EMBL/GenBank/DDBJ databases. Accession No. B4Y882_9VIRU.
Yan, Ziying et al. Ubiquitination of both Adeno-Associated Virus Type 2 and 5 Capsid Proteins Affects the Transduction Efficiency of Recombinant Vectors, Journal of Virology 76(5):2043-2053 (Mar. 2002), 11 pages.
Zhong, Li et al., A Dual Role of EGFR Protein Tyrosine Kinase Signaling in Ubiquitination of AAV2 Capsids and Viral Second-strand DNA Synthesis, The American Society of Gene Therapy, Molecular Therapy 15(7):1323-1330 (Jul. 2007), 8 pages.
Zhong, Li et al., Evaluation of Primitive Murine Hematopoietic Stem and Progenitor Cell Transduction In Vitro and In Vivo by Recombinant Adeno-Associated Virus Vector Serotypes 1 Through 5, Human Gene Therapy 17(3):321-333 (Mar. 2006), 13 pages.
Zhong, Li et al., Next generation of adeno-associated virus 2 vectors: Point mutations in tyrosines lead to high-efficiency transduction at lower doses, Proceedings of the National Academy of Sciences of the United States of America105(22),7827-7832 (Jun. 2008), 7 pages.
Extended European Search Report for Application No. EP 18201865.5 dated Feb. 27, 2019.
Aslanidi et al., Abstract 333: High-Efficiency Transduction of Primary Human Monocyte-Derived Dendritic Cells by Recombinant AAV6 Vectors Containing Mutations in Surface-Exposed Serine and Threonine Residues. Molecular Therapy. May 2013;21(S1):S129.
Aslanidi et al., Abstract 334: Optimization of the capsid of recombinant adeno-associated virus 2 (AAV2) vectors: the final threshold? Molecular Therapy. 2013 May;21(S1):S129.
De Oliveira et al., Herpes simplex virus type 1/adeno-associated virus hybrid vectors. Open Virol J. Jun. 18, 2010;4:109-22. doi: 10.2174/1874357901004030109.
Gabriel et al., Bioengineering of AAV2 capsid at specific serine, threonine, or lysine residues improves its transduction efficiency in vitro and in vivo. Hum Gene Ther Methods. Apr. 2013;24(2):80-93. doi: 10.1089/hgtb.2012.194. Epub Mar. 15, 2013.
Gao et al., Clacles of Adeno-associated viruses are widely disseminated in human tissues. J Virol. Jun. 2004;78(12):6381-8.
Gao et al., Novel adeno-associated viruses from rhesus monkeys as vectors for human gene therapy. Proc Natl Acad Sci USA. Sep. 3, 2002;99(18):11854-9. Epub Aug. 21, 2002.
Li et al., Site-Directed Mutagenesis of Surface-Exposed Lysine Residues Leads to Improved Transduction by AAV2, But Not AAV8, Vectors in Murine Hepatocytes In Vivo. Hum Gene Ther Methods. Dec. 2015;26(6):211-20. doi: 10.1089/hgtb.2015.115. Epub Oct. 27, 2015.
Li et al., The fecal viral flora of California sea lions. J Virol. Oct. 2011;85(19):9909-17. doi: 10.1128/JVI.05026-11. Epub Jul. 27, 2011.
Mori et al., Two novel adeno-associated viruses from cynomolgus monkey: pseudotyping characterization of capsid protein. Virology. Dec. 20, 2004;330(2):375-83.
Radivojac et al., Identification, analysis, and prediction of protein ubiquitination sites. Proteins. Feb. 1, 2010;78(2):365-80. Author manuscript.
Rakoczy et al., Development of Gene Therapy-Based Strategies for the Treatment of Eye Diseases. Drug Development Research. 1999;46:277-285.
Rutledge et al., Infectious clones and vectors derived from adeno-associated virus (AAV) serotypes other than AAV type 2. J Virol. Jan. 1998;72(1):309-19.
Wang et al., Limitations of encapsidation of recombinant self-complementary adeno-associated viral genomes in different serotype capsids and their quantitation. Hum Gene Ther Methods. Aug. 2012;23(4):225-33. doi: 10.1089/hgtb.2012.090.
U.S. Appl. No. 16/565,191, filed Sep. 9, 2019, Aslanidi et al.
EP 18202680.7, Apr. 29, 2019, Partial European Search Report.
EP 18202680.7, Jul. 31, 2019, Extended European Search Report.
U.S. Appl. No. 61/635,273, Mustafa et al., filed Apr. 18, 2012.
U.S. Appl. No. 61/794,995, Mustafa et al., filed Mar. 15, 2013.
Partial European Search Report for Application EP 18202680.7 dated Apr. 29, 2019.
Extended European Search Report for Application No. EP 118202680.7 dated Jul. 31, 2019.

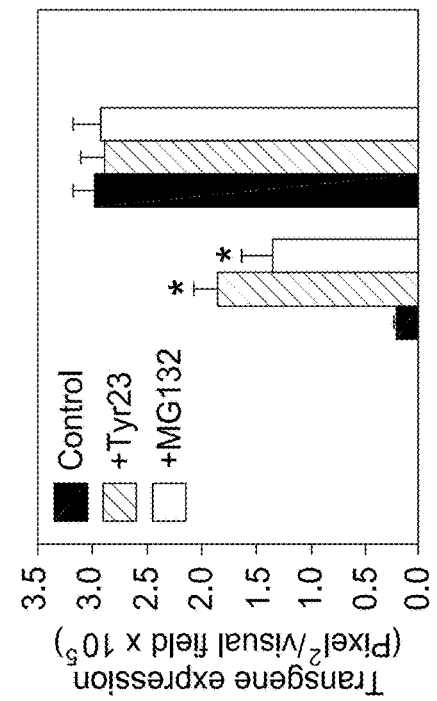
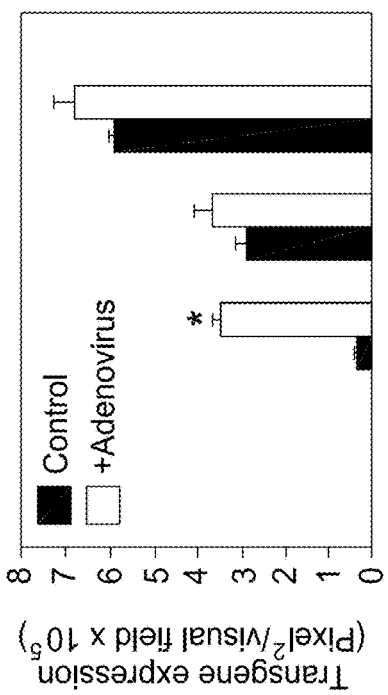
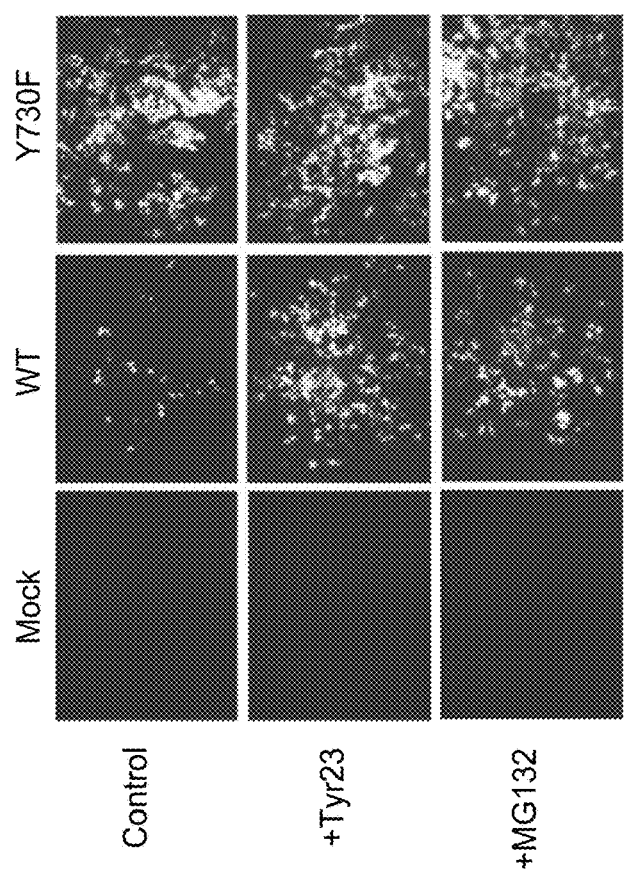
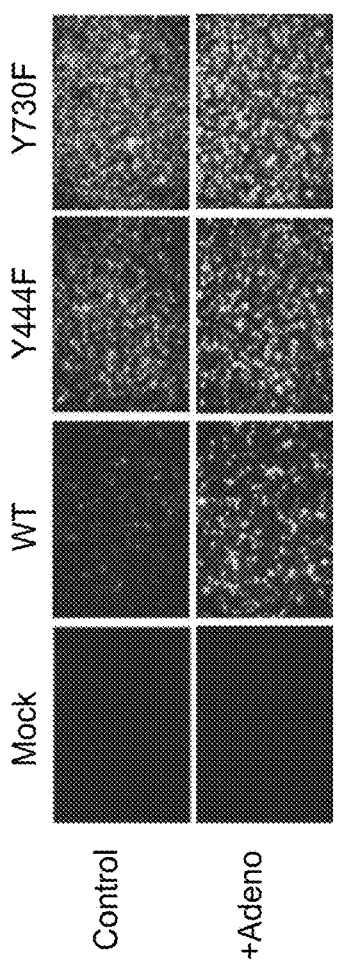

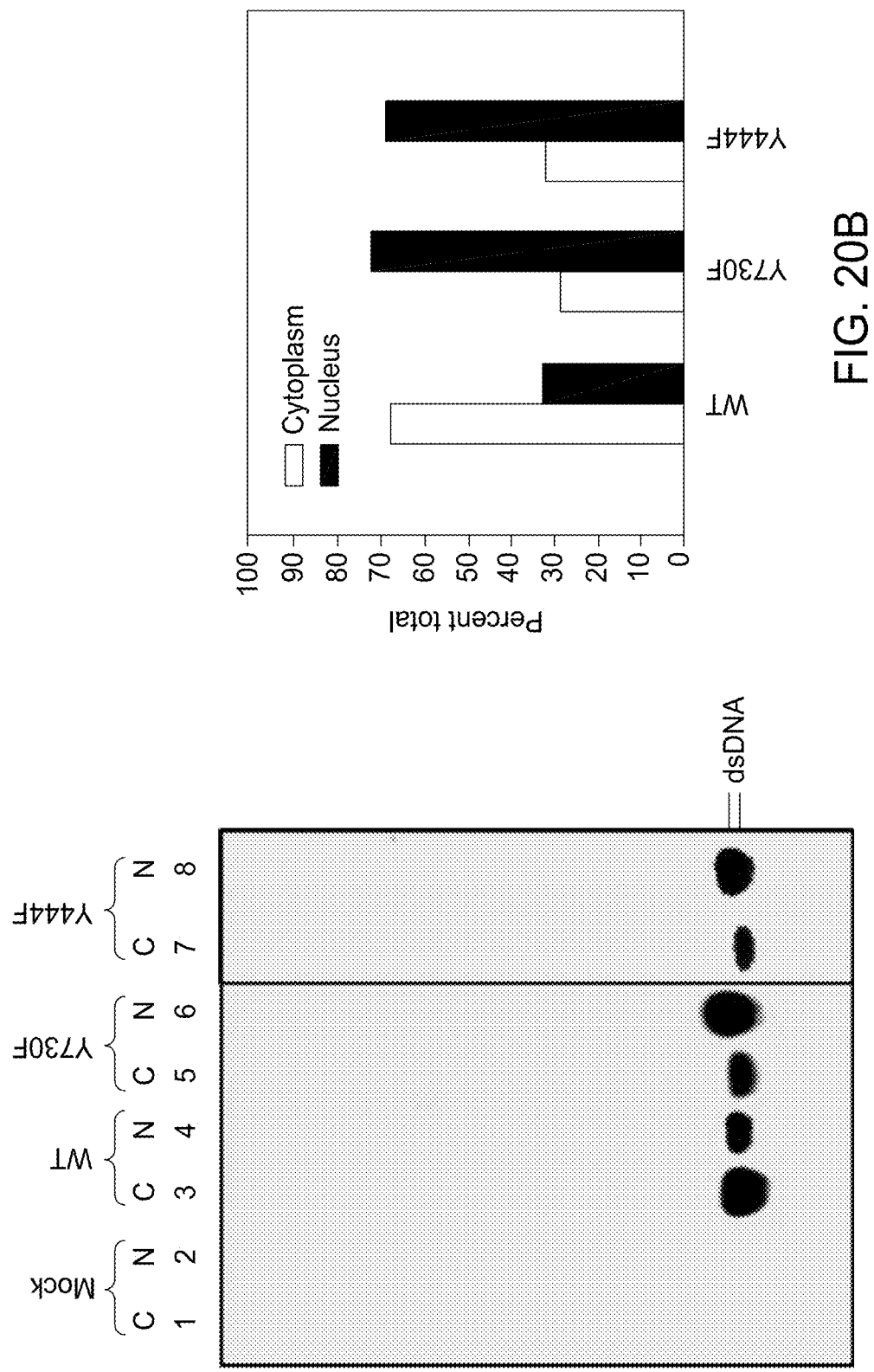

CAPSID MODIFIED RAAV VECTORS AND METHODS OF USE

RELATED APPLICATIONS

The present application is a continuation of U.S. application Ser. No. 14/847,528, filed Sep. 8, 2015, which is a continuation of U.S. application Ser. No. 13/855,640, filed Apr. 2, 2013, which is a continuation of U.S. application Ser. No. 12/595,196, filed Dec. 31, 2009, which is a national stage filing under 35 U.S.C. § 371 of International PCT Application No. PCT/US2008/059647, filed Apr. 8, 2008, which claims priority from provisional application Ser. No. 60/910,798 filed Apr. 9, 2007, the entire contents of each of which are incorporated herein by reference in their entireties.

GOVERNMENT SPONSORSHIP

The invention was made with government support under Grant Nos. DK058327, HL051811, HL059412, HL078810, DK062302, EB002073, GM082946, HL065570, HL076901, and HL097088 awarded by the National Institutes of Health. The government has certain rights in the invention.

FIELD OF THE INVENTION

The present invention relates generally to the fields of molecular biology and virology, and in particular, to the development of gene delivery vehicles. Also disclosed are improved rAAV vector compositions useful in expressing a variety of nucleic acid segments, including those encoding therapeutic proteins polypeptides, peptides, antisense oligonucleotides, and ribozyme constructs, in various gene therapy regimens. Methods are also provided for preparing and using these modified rAAV-based vector constructs in a variety of viral-based gene therapies, and in particular, treatment and prevention of human diseases using conventional gene therapy approaches. The invention also provides rAAV-based vector delivery systems which may be used to assess the relative efficiency and infectivity of a variety of AAV particles having mutations in one or more tyrosine residues of viral capsid proteins.

DESCRIPTION OF RELATED ART

Major advances in the field of gene therapy have been achieved by using viruses to deliver therapeutic genetic material. The adeno-associated virus (AAV) has attracted considerable attention as a highly effective viral vector for gene therapy due to its low immunogenicity and ability to effectively transduce non-dividing cells. AAV has been shown to infect a variety of cell and tissue types, and significant progress has been made over the last decade to adapt this viral system for use in human gene therapy.

In its normal "wild type" form, recombinant AAV (rAAV) DNA is packaged into the viral capsid as a single stranded molecule about 4600 nucleotides (nt) in length. Following infection of the cell by the virus, the molecular machinery of the cell converts the single DNA strand into a double-stranded form. Only the double-stranded DNA form is useful to the polypeptides of the cell that transcribe the contained gene or genes into RNA.

AAV has many properties that favor its use as a gene delivery vehicle: 1) the wild type virus is not associated with any pathologic human condition; 2) the recombinant form does not contain native viral coding sequences; and 3) persistent transgenic expression has been observed in many applications.

The transduction efficiency of recombinant adeno-associated virus 2 (AAV) vectors varies greatly in different cells and tissues in vitro and in vivo. Systematic studies have been performed to elucidate the fundamental steps in the life cycle of AAV. For example, it has been documented that a cellular protein, FKBP52, phosphorylated at tyrosine residues by epidermal growth factor receptor protein tyrosine kinase (EGFR-PTK), inhibits AAV second-strand DNA synthesis and consequently, transgene expression in vitro[24, 25] as well as in vivo.[19, 27, 28] It has also been demonstrated that EGFR-PTK signaling modulates the ubiquitin/proteasome pathway-mediated intracellular trafficking as well as FKBP52-mediated second-strand DNA synthesis of AAV vectors. In those studies, inhibition of EGFR-PTK signaling led to decreased ubiquitination of AAV capsid proteins, which in turn, facilitated nuclear transport by limiting proteasome-mediated degradation of AAV vectors, implicating EGFR-PTK-mediated phosphorylation of tyrosine residues on AAV capsids.

SUMMARY OF THE INVENTION

The present invention overcomes limitations and deficiencies inherent in the prior art by providing novel rAAV-based genetic constructs that encode one or more therapeutic agents useful in the preparation of medicaments for the prevention, treatment, and/or amelioration of one or more diseases, disorders or dysfunctions resulting from a deficiency in one or more of such polypeptides. In particular, the invention provides AAV-based genetic constructs encoding one or more mammalian therapeutic agents (including, e.g., proteins, polypeptides, peptides, antibodies, antigen binding fragments, siRNAs, RNAis, antisense oligo- and polynucleotides, ribozymes, and variants and/or active fragments thereof), for use in the diagnosis, prevention, treatment, and/or amelioration of symptoms of a variety of mammalian diseases, disorders, dysfunctions, trauma, injury, and such like.

Based on the inventors' latest discoveries, a new category of modified rAAV vectors have been developed which provide a higher-efficiency transduction into selected cells than conventional and wild-type rAAV vectors.

By studying site-directed mutational analyses of surface-exposed tyrosine residues on various AAV capsid proteins, the inventors have identified that removal of one or more virion surface-presenting tyrosine residues (which provide a crucial signal for ubiquitination of capsid proteins) yield novel rAAV vectors and viral particles comprising them that bypass the ubiquitination step, thereby avoiding proteasome-mediated degradation, resulting in high-efficiency transduction. The creation of these new vectors dramatically reduces the number of viral particles needed for conventional gene therapy regimens. The resulting tyrosine-modified AAV vectors described herein are more efficient, more stable, less immunogenic, and produced at much lower cost than traditional vectors currently employed in human gene therapy.

Importantly, the methods of the present invention facilitate the production of novel AAV vectors with mutation of one or more surface-exposed tyrosine residues on capsid proteins. These novel mutated vectors avoid degradation by the proteasome, and thus significantly increase the transduction efficiency of these vectors. The inventors have demonstrated that mutation of one or more of the tyrosine residues on the outer surface of the capsid proteins [including, for example, but not limited to, mutation of Tyr252 to Phe272 (Y252F), Tyr272 to Phe272 (Y272F), Tyr444 to Phe444 (Y444F), Tyr500 to Phe500 (Y500F), Tyr700 to Phe700 (Y700F), Tyr704 to Phe704 (Y704F), and Tyr730 to Phe730 (Y730F)] resulted in improved transduction efficiency of the rAAV vectors when compared to wild-type.

In one aspect, the invention provides compositions comprising recombinant adeno-associated viral (AAV) vectors, virions, viral particles, and pharmaceutical formulations thereof, useful in methods for delivering genetic material encoding one or more beneficial or therapeutic product(s) to mammalian cells and tissues. In particular, the compositions and methods of the invention provide a significant advancement in the art through their use in the treatment, prevention, and/or amelioration of symptoms of one or more mammalian diseases. It is contemplated that human gene therapy will particularly benefit from the present teachings by providing new and improved viral vector constructs for use in the treatment of a number of diverse diseases, disorders, and dysfunctions.

In another aspect, the invention concerns modified rAAV vector that encode one or more mammalian therapeutic agents for the prevention, treatment, and/or amelioration of one or more disorders in the mammal into which the vector construct is delivered. In particular, the invention provides rAAV-based expression constructs that encode one or more mammalian therapeutic agent(s) (including, but not limited to, for example, protein(s), polypeptide(s), peptide(s), enzyme(s), antibodies, antigen binding fragments, as well as variants, and/or active fragments thereof, for use in the treatment, prophylaxis, and/or amelioration of one or more symptoms of a mammalian disease, dysfunction, injury, and/or disorder.

In another embodiment, the invention concerns genetically modified rAAV vectors that comprise at least a first nucleic acid segment that encodes one or more therapeutic agents that alter, inhibit, reduce, prevent, eliminate, or impair the activity of one or more endogenous biological processes in the cell. In particular embodiments, such therapeutic agents may be those that selectively inhibit or reduce the effects of one or more metabolic processes, dysfunctions, disorders, or diseases. In certain embodiments, the defect may be caused by injury or trauma to the mammal for which treatment is desired. In other embodiments, the defect may be caused the over-expression of an endogenous biological compound, while in other embodiments still; the defect may be caused by the under-expression or even lack of one or more endogenous biological compounds.

When the use of such vectors is contemplated for introduction of one or more exogenous proteins, polypeptides, peptides, ribozymes, siRNAs, and/or antisense oligonucleotides, to a particular cell transfected with the vector, one may employ the modified AAV vectors disclosed herein by incorporating into the vector at least a first exogenous polynucleotide operably positioned downstream and under the control of at least a first heterologous promoter that expresses the polynucleotide in a cell comprising the vector to produce the encoded therapeutic agent, including for example, peptides, proteins, polypeptides, antibodies, ribozymes, siRNAs, and antisense oligo- or polynucleotides. Such constructs may employ one or more heterologous promoters to express the therapeutic agent of interest. Such promoters may be constitutive, inducible, or even cell- or tissue-specific. Exemplary promoters include, but are not limited to, a CMV promoter, a β-actin promoter, a hybrid CMV promoter, a hybrid β-actin promoter, an EF1 promoter, a U1a promoter, a U1b promoter, a Tet-inducible promoter, a VP16-LexA promoter, a joint-specific promoter and a human-specific promoter.

The genetically-modified rAAV vectors or expression systems of the invention may also further comprise a second nucleic acid segment that comprises, consists essentially of, or consists of, one or more enhancers, regulatory elements, transcriptional elements, to alter or effect transcription of the heterologous gene cloned in the rAAV vectors. For example, the rAAV vectors of the present invention may further comprise a second nucleic acid segment that comprises, consists essentially of, or consists of, at least a first CMV enhancer, a synthetic enhancer, or a cell- or tissue-specific enhancer. The second nucleic acid segment may also further comprise, consist essentially of, or consist of one or more intron sequences, post-transcriptional regulatory elements, or such like. The vectors and expression systems of the invention may also optionally further comprise a third nucleic acid segment that comprises, consists essentially of, or consists of, one or more polylinker or multiple restriction sites/cloning region(s) to facilitate insertion of one or more selected genetic elements, polynucleotides, and the like into the rAAV vectors at a convenient restriction site.

In aspects of the invention, the exogenous polynucleotides that are comprised within one or more of the improved rAAV vectors disclosed herein are preferably of mammalian origin, with polynucleotides encoding polypeptides and peptides of human, primate, murine, porcine, bovine, ovine, feline, canine, equine, epine, caprine, or lupine origin being particularly preferred.

As described above, the exogenous polynucleotide will preferably encode one or more proteins, polypeptides, peptides, enzymes, antibodies, siRNAs, ribozymes, or antisense polynucleotides, oligonucleotides, PNA molecules, or a combination of two or more of these therapeutic agents. In fact, the exogenous polynucleotide may encode two or more such molecules, or a plurality of such molecules as may be desired. When combinational gene therapies are desired, two or more different molecules may be produced from a single rAAV expression system, or alternatively, a selected host cell may be transfected with two or more unique rAAV expression systems, each of which may comprise one or more distinct polynucleotides that encode a therapeutic agent.

In other embodiments, the invention also provides genetically-modified rAAV vectors that are comprised within an infectious adeno-associated viral particle or a virion, or pluralities of such particles, which themselves may also be comprised within one or more diluents, buffers, physiological solutions or pharmaceutical vehicles, formulated for administration to a mammal such as a human for therapeutic, and/or prophylactic gene therapy regimens. Such vectors, virus particles, virions, and pluralities thereof may also be provided in excipient formulations that are acceptable for veterinary administration to selected livestock, exotic or domesticated animals, companion animals (including pets and such like), as well as non-human primates, zoological or otherwise captive specimens, and such like, wherein the use of such vectors and related gene therapy is indicated to produce a beneficial effect upon administration to such an animal.

The invention also concerns host cells that comprise at least one of the disclosed rAAV vectors, virus particles, or virions. Such host cells are particularly mammalian host cells, with human host cells being particularly highly preferred, and may be either isolated, in cell or tissue culture. In the case of genetically modified animal models, the transformed host cells may even be comprised within the body of a non-human animal itself.

In certain embodiments, the creation of recombinant non-human host cells, and/or isolated recombinant human host cells that comprise one or more of the disclosed rAAV vectors is also contemplated to be useful for a variety of diagnostic, and laboratory protocols, including, for example, means for the production of large-scale quantities of the rAAV vectors described herein. Such virus production methods are particularly contemplated to be an improvement over existing methodologies including in particular, those that require very high titers of the viral stocks in order to be useful as a gene therapy tool. The inventors contemplate that one very significant advantage of the present methods will be the ability to utilize lower titers of viral particles in mammalian transduction protocols, yet still retain transfection rates at a suitable level.

Compositions comprising one or more of the disclosed rAAV vectors, expression systems, infectious AAV particles, or host cells also form part of the present invention, and particularly those compositions that further comprise at least a first pharmaceutically-acceptable excipient for use in therapy, and for use in the manufacture of medicaments for the treatment of one or more mammalian diseases, disorders, dysfunctions, or trauma. Such pharmaceutical compositions may optionally further comprise one or more diluents, buffers, liposomes, a lipid, a lipid complex; or the tyrosine-modified rAAV vectors may be comprised within a microsphere or a nanoparticle. Pharmaceutical formulations suitable for intramuscular, intravenous, or direct injection into an organ or tissue or a plurality of cells or tissues of a human or other mammal are particularly preferred, however, the compositions disclosed herein may also find utility in administration to discreet areas of the mammalian body, including for example, formulations that are suitable for direct injection into one or more organs, tissues, or cell types in the body. Such injection sites include, but are not limited to, the brain, a joint or joint capsule, a synovium or subsynovium tissue, tendons, ligaments, cartilages, bone, periarticular muscle or an articular space of a mammalian joint, as well as direct administration to an organ such as the heart, liver, lung, pancreas, intestine, brain, bladder, kidney, or other site within the patient's body, including, for example, introduction of the viral vectors via intraabdominal, intrathorascic, intravascular, or intracerebroventricular delivery.

Other aspects of the invention concern recombinant adeno-associated virus virion particles, compositions, and host cells that comprise, consist essentially of, or consist of, one or more of the rAAV vectors disclosed herein, such as for example pharmaceutical formulations of the vectors intended for administration to a mammal through suitable means, such as, by intramuscular, intravenous, intra-articular, or direct injection to one or more cells, tissues, or organs of a selected mammal. Typically, such compositions may be formulated with pharmaceutically-acceptable excipients as described hereinbelow, and may comprise one or more liposomes, lipids, lipid complexes, microspheres or nanoparticle formulations to facilitate administration to the selected organs, tissues, and cells for which therapy is desired.

Kits comprising one or more of the disclosed rAAV vectors, virions, viral particles, transformed host cells or pharmaceutical compositions comprising such; and instructions for using the kit in a therapeutic, diagnostic, or clinical embodiment also represent preferred aspects of the present disclosure. Such kits may further comprise one or more reagents, restriction enzymes, peptides, therapeutics, pharmaceutical compounds, or means for delivery of the composition(s) to host cells, or to an animal (e.g., syringes, injectables, and the like). Such kits may be therapeutic kits for treating, preventing, or ameliorating the symptoms of a disease, deficiency, dysfunction, and/or injury, and may comprise one or more of the modified rAAV vector constructs, expression systems, virion particles, or a plurality of such particles, and instructions for using the kit in a therapeutic and/or diagnostic medical regimen. Such kits may also be used in large-scale production methodologies to produce large quantities of the viral vectors themselves (with or without a therapeutic agent encoded therein) for commercial sale, or for use by others, including e.g., virologists, medical professionals, and the like.

Another important aspect of the present invention concerns methods of use of the disclosed rAAV vectors, virions, expression systems, compositions, and host cells described herein in the preparation of medicaments for preventing, treating or ameliorating the symptoms of various diseases, dysfunctions, or deficiencies in an animal, such as a vertebrate mammal. Such methods generally involve administration to a mammal, or human in need thereof, one or more of the disclosed vectors, virions, viral particles, host cells, compositions, or pluralities thereof, in an amount and for a time sufficient to prevent, treat, or lessen the symptoms of such a disease, dysfunction, or deficiency in the affected animal. The methods may also encompass prophylactic treatment of animals suspected of having such conditions, or administration of such compositions to those animals at risk for developing such conditions either following diagnosis, or prior to the onset of symptoms.

As described above, the exogenous polynucleotide will preferably encode one or more proteins, polypeptides, peptides, ribozymes, or antisense oligonucleotides, or a combination of these. In fact, the exogenous polynucleotide may encode two or more such molecules, or a plurality of such molecules as may be desired. When combinational gene therapies are desired, two or more different molecules may be produced from a single rAAV expression system, or alternatively, a selected host cell may be transfected with two or more unique rAAV expression systems, each of which will provide unique heterologous polynucleotides encoding at least two different such molecules.

In other embodiment, the invention also concerns the disclosed rAAV vectors comprised within an infectious adeno-associated viral particle, comprised within one or more pharmaceutical vehicles, and may be formulated for administration to a mammal such as a human for therapeutic, and/or prophylactic gene therapy regimens. Such vectors may also be provided in pharmaceutical formulations that are acceptable for veterinary administration to selected livestock, domesticated animals, pets, and the like.

The invention also concerns host cells that comprise the disclosed rAAV vectors and expression systems, particularly mammalian host cells, with human host cells being particularly preferred.

Compositions comprising one or more of the disclosed rAAV vectors, expression systems, infectious AAV particles, host cells also form part of the present invention, and particularly those compositions that further comprise at least a first pharmaceutically-acceptable excipient for use in the manufacture of medicaments and methods involving therapeutic administration of such rAAV vectors. Such pharmaceutical compositions may optionally further comprise liposomes, a lipid, a lipid complex; or the rAAV vectors may be comprised within a microsphere or a nanoparticle. Pharmaceutical formulations suitable for intramuscular, intravenous, or direct injection into an organ or tissue of a human are particularly preferred.

Other aspects of the invention concern recombinant adeno-associated virus virion particles, compositions, and host cells that comprise one or more of the AAV vectors disclosed herein, such as for example pharmaceutical formulations of the vectors intended for administration to a mammal through suitable means, such as, by intramuscular, intravenous, or direct injection to cells, tissues, or organs of a selected mammal. Typically, such compositions may be formulated with pharmaceutically-acceptable excipients as described hereinbelow, and may comprise one or more liposomes, lipids, lipid complexes, microspheres or nanoparticle formulations to facilitate administration to the selected organs, tissues, and cells for which therapy is desired.

Kits comprising one or more of the disclosed vectors, virions, host cells, viral particles or compositions; and (ii) instructions for using the kit in therapeutic, diagnostic, or clinical embodiments also represent preferred aspects of the present disclosure. Such kits may further comprise one or more reagents, restriction enzymes, peptides, therapeutics, pharmaceutical compounds, or means for delivery of the compositions to host cells, or to an animal, such as syringes, injectables, and the like. Such kits may be therapeutic kits for treating or ameliorating the symptoms of particular diseases, and will typically comprise one or more of the modified AAV vector constructs, expression systems, virion particles, or therapeutic compositions described herein, and instructions for using the kit.

Another important aspect of the present invention concerns methods of use of the disclosed vectors, virions, expression systems, compositions, and host cells described herein in the preparation of medicaments for treating or ameliorating the symptoms of various polypeptide deficiencies in a mammal. Such methods generally involve administration to a mammal, or human in need thereof, one or more of the disclosed vectors, virions, host cells, or compositions, in an amount and for a time sufficient to treat or ameliorate the symptoms of such a deficiency in the affected mammal. The methods may also encompass prophylactic treatment of animals suspected of having such conditions, or administration of such compositions to those animals at risk for developing such conditions either following diagnosis, or prior to the onset of symptoms.

BRIEF DESCRIPTION OF THE DRAWINGS

The following drawings form part of the present specification and are included to further demonstrate certain aspects of the present invention. The invention may be better understood by reference to the following description taken in conjunction with the accompanying drawings, in which like reference numerals identify like elements, and in which:

FIG. 1A shows transgene expression was detected by fluorescence microscopy at 48 hr post-infection. Original magnification 100×. FIG. 1B shows quantitative analyses of AAV2 transduction efficiency. Images from five visual fields were analyzed quantitatively by ImageJ® analysis software. Transgene expression was assessed as total area of green fluorescence (pixel$^2$) per visual field (mean±SD). Analysis of variance (ANOVA) was used to compare test results with the control and they were determined to be statistically significant. *$P<0.05$ vs. control+ssAAV2-EGFP; # $P<0.05$ vs. control+scAAV2-EGFP.

FIG. 2A shows transgene expression was detected by fluorescence microscopy at 48-hr post-infection (original magnification: 100×). FIG. 2B illustrates the quantitative analyses of AAV2 transduction efficiency was assessed as described in the legend to FIG. 1A and FIG. 1B, and were determined to be statistically significant. *$P<0.05$ vs. control+ssAAV2-EGFP; # $P<0.05$ vs. control+scAAV2-EGFP.

FIG. 4A shows HeLa cells mock-treated or treated with Tyr23, MG132 or both, and cells stably transfected with the wt TC-PTP expression plasmid were either mock-treated or treated with MG132 followed by infection with AAV-lacZ vectors. Cells were fixed and stained with X-Gal. Transgene expression was detected by microscopy at 48-hr post-infection (original magnification: 100×). FIG. 4B shows the quantitative analyses of AAV transduction efficiency assessed as described in the legend to FIG. 1A and FIG. 1B, and were determined to be statistically significant. *$P<0.05$ vs. control+ssAAV2-lacZ.

FIG. 5A shows HeLa cells mock-treated or treated with Tyr23, MG132, or both, and cells either mock-transfected or stably transfected with the wt- or mTC-PTP expression plasmids were either mock-treated or treated with MG132. Transgene expression was detected by fluorescence microscopy at 48 hr post-infection (original magnification 100×). FIG. 5B: Quantitative analyses of AAV transduction efficiency was assessed as described in the legend to FIG. 1A and FIG. 1B, and were determined to be statistically significant. *$P<0.05$ vs. control+scAAV2-EGFP.

FIG. 14A: HeLa cells were infected by ssAAV2-RFP vectors, which were pre-incubated with ATP, EGFR-TPK or both. Transgene expression was detected by fluorescence microscopy at 48 hr post-infection (original magnification: 100×). FIG. 14B shows the quantitative analyses of AAV2 transduction efficiency. Images from five visual fields were analyzed quantitatively by ImageJ® analysis software. Transgene expression was assessed as total area of red fluorescence (pixel$^2$) per visual field (mean±SD). Analysis of variance (ANOVA) was used to compare test results with the control and they were determined to be statistically significant. *$P<0.05$ vs. ssAAV2-RFP.

In FIG. 15A HeLa cells were infected by scAAV2-EGFP vectors, which were pre-incubated with ATP, EGFR-TPK or both. Transgene expression was detected by fluorescence microscopy at 48 hr post-infection (original magnification: 100×). FIG. 15B shows the quantitative analyses of AAV2 transduction efficiency assessed as described in the legend to FIG. 14A and FIG. 14B, and determined to be statistically significant. *$P<0.05$ vs. scAAV2-EGFP.

FIG. 17A shows transgene expression was detected by fluorescence microscopy 2 weeks post-injection of $1\times10^{10}$ viral particles/animal via the tail vein (n=2 per experimental group) (original magnification: 50×). FIG. 17B illustrates quantitation of the transduction efficiency in hepatocytes in C57BL/6 mice. *$P<0.01$ vs. WT scAAV2-EGFP.

FIG. 18A, FIG. 18B, FIG. 18C, and FIG. 18D show comparative analyses of AAV2-mediated transduction efficiency in HeLa C12 cells with or without co-infection with adenovirus, and treatment with proteasome- or EGFR-PTK-inhibitors following transduction with tyrosine-mutant capsid scAAV2-EGFP vectors. FIG. 18A shows cells mock-infected or infected with adenovirus, following transduction with the WT, Y444F or Y730F AAV2-EGFP vectors (original magnification: 100×). FIG. 18B illustrates quantitation of the transduction efficiency in HeLa C12 cells. Shown in FIG. 18C are cells that were mock-treated or treated with Tyr23 or MG132, following transduction with the WT or Y730F AAV2-EGFP vectors (original magnification: 100×). FIG. 18D illustrates quantitation of the transduction efficiency. *$P<0.05$ vs. control.

FIG. 20A and FIG. 20B depict Southern hybridization analyses for intracellular trafficking of the WT and tyrosine-mutant scAAV2-EGFP vectors and cytoplasmic [C] and nuclear [N] distribution of AAV2 genomes. HeLa cells were mock-infected (lanes 1 and 2) or infected with the WT (lanes 2 and 3), Y730F (lanes 5 and 6) or Y444F (lanes 7 and 8) scAAV2-EGFP vectors. In FIG. 20A, nuclear and cytoplasmic fractions were obtained 18 hr post-infection, low-$M_r$ DNA samples were isolated and electrophoresed on 1% agarose gels followed by Southern blot hybridization using a $^{32}$P-labeled lacZ DNA probe. In FIG. 20B quantitation of relative amounts of viral genomes is demonstrated. These results are representative of two independent studies.

Figure 21A:
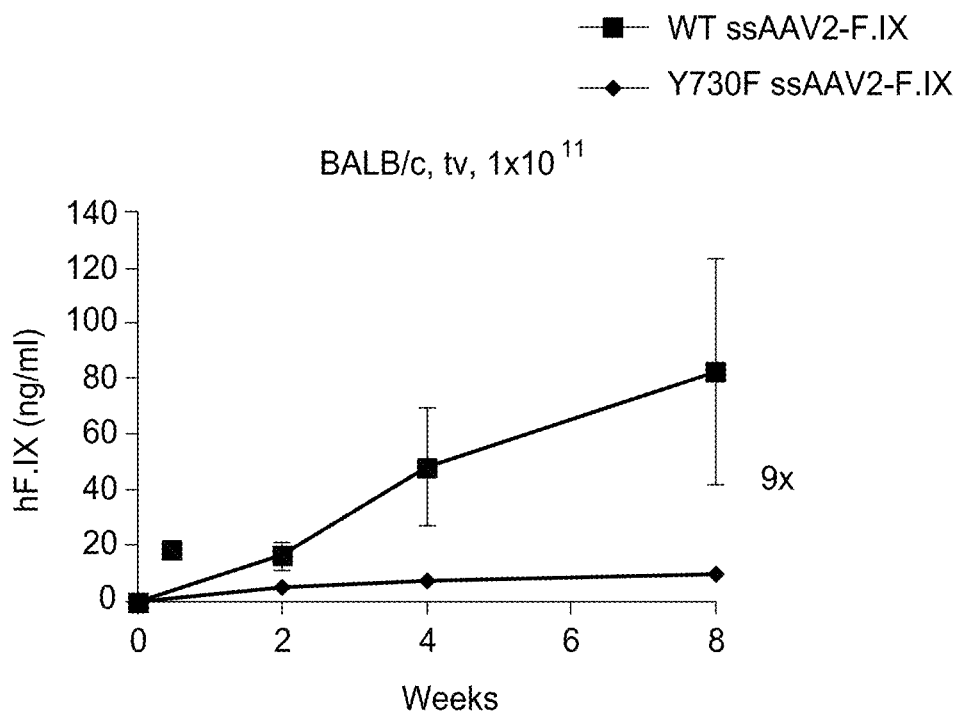
FIG. 21A, FIG. 21B, FIG. 21C, and FIG. 21D illustrate comparative analyses of the WT or Y730F ssAAV2-ApoE/hAAT-hF.IX vector-mediated transduction efficiency in hepatocytes in mice in vivo. Human F.IX (hF.IX) expression in plasma was determined as a function of time after injection of $1\times10^{11}$ viral particles/animal in BALB/c (FIG.
Figure 21B:
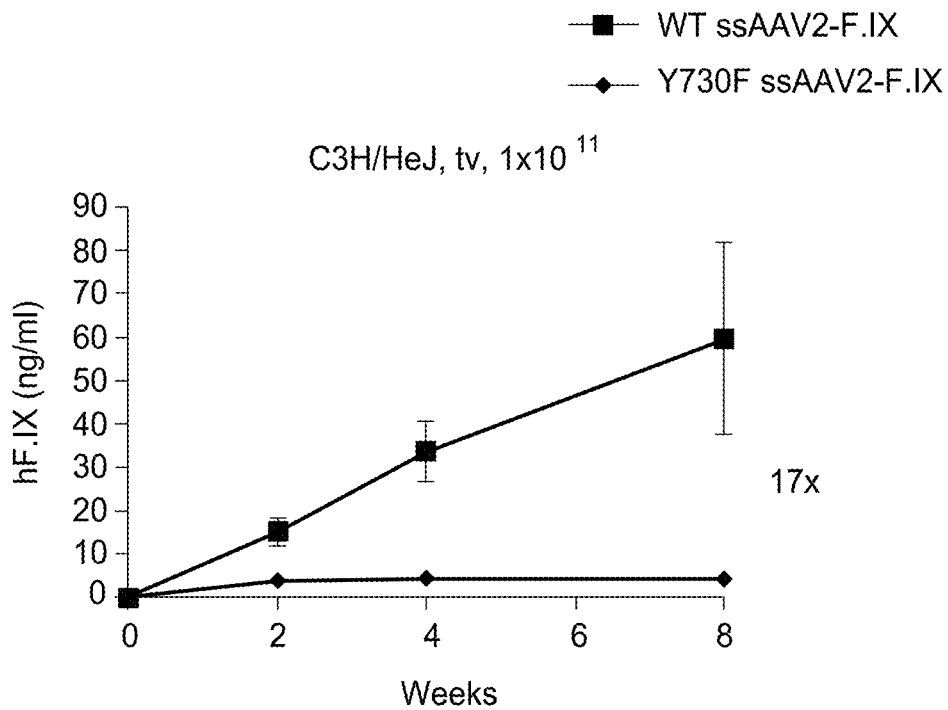
Figure 21C:
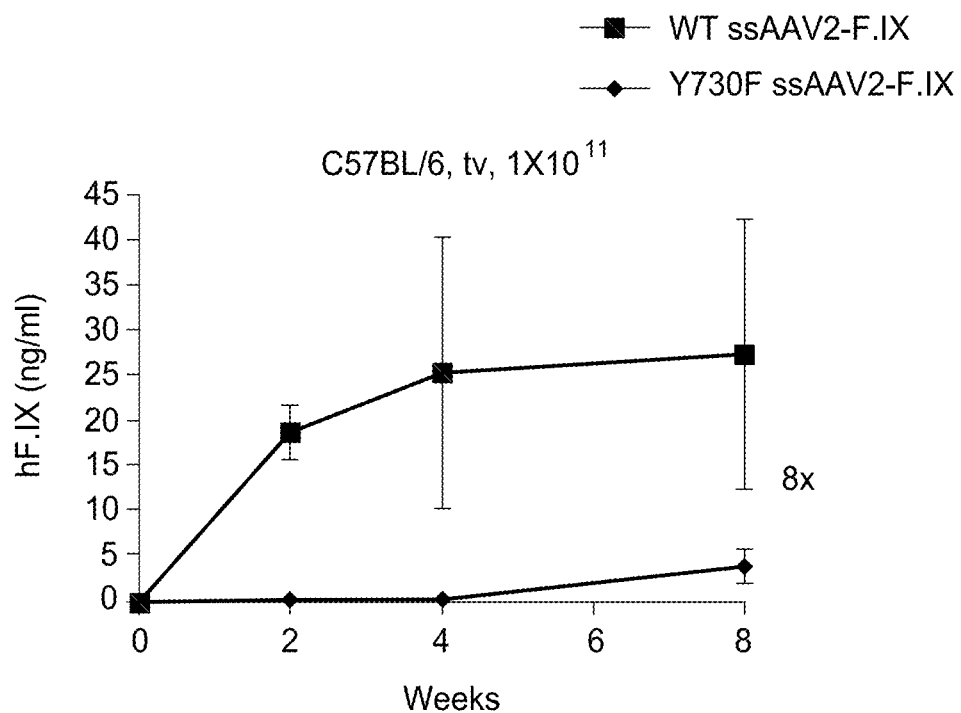
Figure 21D:
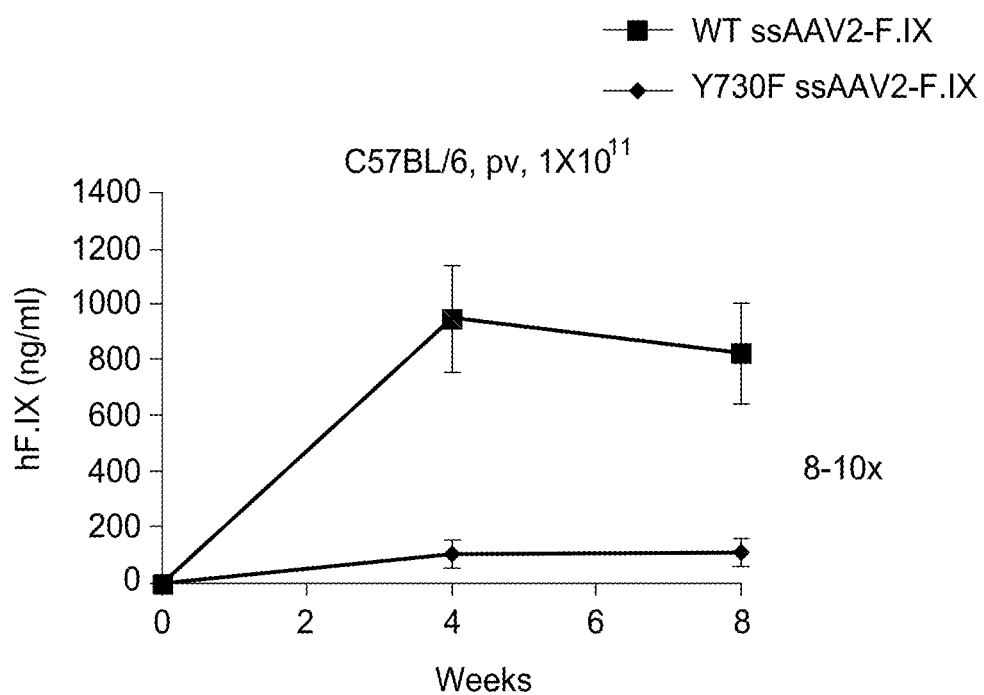

21A), and C3H/HeJ (FIG. 21B) mice via tail vein (tv), and $1 \times 10^{10}$ viral particles/animal in C57BL/6 mice via tail vein (tv) (FIG. 21C), or portal vein (pv) (FIG. 21D). Fold-increase of hF.IX peak levels of Y730F vectors compared to the WT capsid vectors is indicated for each panel. Data are mean±SD (n=4 per experimental group).

DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The adeno-associated virus 2 (AAV2) is a non-pathogenic human parvovirus which has gained attention as an alternative to the more commonly used retrovirus- and adenovirus-based vectors for gene transfer and gene therapy. Recombinant AAV2 vectors have been shown to transduce a wide variety of cells and tissues in vitro and in vivo, and are currently in use in Phase I/II clinical trials for gene therapy of a number of diseases such as cystic fibrosis, α-1 antitrypsin deficiency, Parkinson's disease, Batten's disease, and muscular dystrophy. Systematic studies have been undertaken to elucidate some of the fundamental steps in the life cycle of AAV2 vectors, which include viral binding and entry, intracellular trafficking, uncoating, second-strand DNA synthesis and transgene expression, and viral genome integration into the host cell chromosome.

The ubiquitin-proteasome pathway has been shown to play an essential role in AAV2 intracellular trafficking. It has also been observed that perturbations in EGFR-PTK signaling affects AAV2 transduction efficiency by not only augmenting viral second-strand DNA synthesis, but also by facilitating intracellular trafficking from the cytoplasm to the nucleus. Previously it was reported that intact AAV2 capsids could be phosphorylated at tyrosine residues by EGFR-PTK, but not at serine/threonine residues by casein kinase II (CKII) under cell-free conditions in vitro, and that tyrosine-phosphorylation of AAV2 capsids negatively affects viral intracellular trafficking and transgene expression in intact cells in vivo. Based on these studies, it was hypothesized that EGFR-PTK-mediated phosphorylation of capsid proteins at tyrosine residues is a pre-requisite for ubiquitination of intact AAV2 particles, and that a substantial number of ubiquitinated virions are recognized and degraded by cytoplasmic proteasomes on their way to the nucleus, leading to inefficient nuclear transport.

Substitution of surface exposed tyrosine residues on AAV2 capsids thus permits the vectors to escape ubiquitination and thus, proteasome-mediated degradation. The inventors have demonstrated that AAV capsids can be phosphorylated at tyrosine residues by EGFR-PTK in an in vitro phosphorylation assay, and that the phosphorylated AAV capsids retain their structural integrity. Although phosphorylated AAV vectors could enter cells as efficiently as their unphosphorylated counterparts, their transduction efficiency was significantly reduced. This reduction was not due to impaired viral second-strand DNA synthesis since transduction efficiency of both single-stranded AAV (ssAAV) and self-complementary AAV (rAAV) vectors was decreased by ~68% and ~74%, respectively. Intracellular trafficking of tyrosine-phosphorylated AAV vectors from cytoplasm to nucleus was also significantly decreased, most likely led to ubiquitination of AAV capsids followed by proteasome-mediated degradation.

In one embodiment, the invention provides a recombinant adeno-associated viral (rAAV) vector that comprises at least a first capsid protein comprising at least a first phosphorylated tyrosine amino acid residue, and wherein said vector further comprises at least a first nucleic acid segment that encodes a therapeutic agent operably linked to a promoter capable of expressing said segment in a host cell that comprises said vector.

The rAAV vector may optionally further comprise at least one enhancer sequence that is operably linked to the nucleic acid segment.

Exemplary enhancer sequences include, but are not limited to, one or more selected from the group consisting of a CMV enhancer, a synthetic enhancer, a liver-specific enhancer, an vascular-specific enhancer, a brain-specific enhancer, a neural cell-specific enhancer, a lung-specific enhancer, a muscle-specific enhancer, a kidney-specific enhancer, a pancreas-specific enhancer, and an islet cell-specific enhancer.

Exemplary promoters include one or more heterologous, tissue-specific, constitutive or inducible promoters, including, for example, but not limited to, a promoter selected from the group consisting of a CMV promoter, a β-actin promoter, an insulin promoter, an enolase promoter, a BDNF promoter, an NGF promoter, an EGF promoter, a growth factor promoter, an axon-specific promoter, a dendrite-specific promoter, a brain-specific promoter, a hippocampal-specific promoter, a kidney-specific promoter, an elafin promoter, a cytokine promoter, an interferon promoter, a growth factor promoter, an alpha-1 antitrypsin promoter, a brain-specific promoter, a neural cell-specific promoter, a central nervous system cell-specific promoter, a peripheral nervous system cell-specific promoter, an interleukin promoter, a serpin promoter, a hybrid CMV promoter, a hybrid β-actin promoter, an EF1 promoter, a U1a promoter, a U1b promoter, a Tet-inducible promoter and a VP16-LexA promoter. In exemplary embodiments, the promoter is a mammalian or avian β-actin promoter.

The first nucleic acid segment may also further comprise a post-transcriptional regulatory sequence or a polyadenylation signal, including, for example, but not limited to, a woodchuck hepatitis virus post-transcription regulatory element, or a polyadenylation signal sequence.

Exemplary therapeutic agents include, but are not limited to, an agent selected from the group consisting of a polypeptide, a peptide, an antibody, an antigen binding fragment, a ribozyme, a peptide nucleic acid, an siRNA, an RNAi, an antisense oligonucleotide and an antisense polynucleotide.

In exemplary embodiments, the rAAV vectors of the invention will encode a therapeutic protein or polypeptide selected from the group consisting of an adrenergic agonist, an anti-apoptosis factor, an apoptosis inhibitor, a cytokine receptor, a cytokine, a cytotoxin, an erythropoietic agent, a glutamic acid decarboxylase, a glycoprotein, a growth factor, a growth factor receptor, a hormone, a hormone receptor, an interferon, an interleukin, an interleukin receptor, a kinase, a kinase inhibitor, a nerve growth factor, a netrin, a neuroactive peptide, a neuroactive peptide receptor, a neurogenic factor, a neurogenic factor receptor, a neuropilin, a neurotrophic factor, a neurotrophin, a neurotrophin receptor, an N-methyl-D-aspartate antagonist, a plexin, a protease, a protease inhibitor, a protein decarboxylase, a protein kinase, a protein kinsase inhibitor, a proteolytic protein, a proteolytic protein inhibitor, a semaphoring, a semaphorin receptor, a serotonin transport protein, a serotonin uptake inhibitor, a serotonin receptor, a serpin, a serpin receptor, and a tumor suppressor.

In certain applications, the modified high-transduction efficiency vectors may comprise a nucleic acid segment that encodes a polypeptide selected from the group consisting of BDNF, CNTF, CSF, EGF, FGF, G-SCF, GM-CSF, gonadotropin, IFN, IFG-1, M-CSF, NGF, PDGF, PEDF, TGF, TGF-B2, TNF, VEGF, prolactin, somatotropin, XIAP1, IL-1, IL-2, IL-3, IL-4, IL-5, IL-6, IL-7, IL-8, IL-9, IL-10, IL-10(I87A), viral IL-10, IL-11, IL-12, IL-13, IL-14, IL-15, IL-16, IL-17, and IL-18. Such therapeutic agents may be of human, murine, avian, porcine, bovine, ovine, feline, canine, equine, epine, caprine, lupine or primate origin.

In exemplary embodiments, the mutation may be made at one or more of the following amino acid residues: Tyr252, Tyr272, Tyr444, Tyr500, Tyr700, Tyr704, Tyr730; Tyr275, Tyr281, Tyr508, Tyr576, Tyr612, Tyr673 or Tyr720. Exemplary mutations are tyrosine-to-phenylalanine mutations including, but not limited to, Y252F, Y272F, Y444F, Y500F, Y700F, Y704F, Y730F, Y275F, Y281F, Y508F, Y576F, Y612G, Y673F and Y720F.

The rAAV vectors of the present invention may be comprised within an adeno-associated viral particle or infectious rAAV virion, including for example, virions selected from the group consisting of an AAV serotype 1, an AAV serotype 2, an AAV serotype 3, an AAV serotype 4, an AAV serotype 5 and an AAV serotype 6.

The rAAV vectors of the present invention may also be comprised within an isolated mammalian host cell, including for example, human, primate, murine, feline, canine, porcine, ovine, bovine, equine, epine, caprine and lupine host cells. The rAAV vectors may be comprised within an isolated mammalian host cell such as a human endothelial, epithelial, vascular, liver, lung, heart, pancreas, intestinal, kidney, muscle, bone, neural, blood, or brain cell.

In related embodiments, the invention also provides a composition that comprises one or more of the disclosed tyrosine-modified rAAV vectors comprised within a kit for diagnosing, preventing, treating or ameliorating one or more symptoms of a mammalian disease, injury, disorder, trauma or dysfunction. Such kits may be useful in diagnosis, prophylaxis, and/or therapy, and particularly useful in the treatment, prevention, and/or amelioration of one or more symptoms of cancer, diabetes, autoimmune disease, kidney disease, cardiovascular disease, pancreatic disease, intestinal disease, liver disease, neurological disease, neuromuscular disorder, neuromotor deficit, neuroskeletal impairment, neurological disability, neurosensory dysfunction, stroke, ischemia, eating disorder, $\alpha_1$-antitrypsin (AAT) deficiency, Batten's disease, Alzheimer's disease, Huntington's disease, Parkinson's disease, skeletal disease, trauma, or pulmonary disease.

The invention also provides for the use of a composition disclosed herein in the manufacture of a medicament for treating, preventing or ameliorating the symptoms of a disease, disorder, dysfunction, injury or trauma, including, but not limited to, the treatment, prevention, and/or prophylaxis of a disease, disorder or dysfunction, and/or the amelioration of one or more symptoms of such a disease, disorder or dysfunction. Exemplary conditions for which rAAV viral based gene therapy may find particular utility include, but are not limited to, cancer, diabetes, autoimmune disease, kidney disease, cardiovascular disease, pancreatic disease, intestinal disease, liver disease, neurological disease, neuromuscular disorder, neuromotor deficit, neuroskeletal impairment, neurological disability, neurosensory dysfunction, stroke, $\alpha_1$-antitrypsin (AAT) deficiency, Batten's disease, ischemia, an eating disorder, Alzheimer's disease, Huntington's disease, Parkinson's disease, skeletal disease and pulmonary disease.

The invention also provides a method for treating or ameliorating the symptoms of such a disease, injury, disorder, or dysfunction in a mammal Such methods generally involve at least the step of administering to a mammal in need thereof, one or more of the tyrosine-modified rAAV vectors as disclosed herein, in an amount and for a time sufficient to treat or ameliorate the symptoms of such a disease, injury, disorder, or dysfunction in the mammal.

Such treatment regimens are particularly contemplated in human therapy, via administration of one or more compositions either intramuscularly, intravenously, subcutaneously, intrathecally, intraperitoneally, or by direct injection into an organ or a tissue of the mammal under care.

The invention also provides a method for providing to a mammal in need thereof, a therapeutically-effective amount of the rAAV compositions of the present invention, in an amount, and for a time effective to provide the patient with a therapeutically-effective amount of the desired therapeutic agent(s) encoded by one or more nucleic acid segments comprised within the rAAV vector. Preferably, the therapeutic agent is selected from the group consisting of a polypeptide, a peptide, an antibody, an antigen binding fragment, a ribozyme, a peptide nucleic acid, an siRNA, an RNAi, an antisense oligonucleotide and an antisense polynucleotide.

AAV Vector Compositions

One important aspect of the present methodology is the fact that the improved rAAV vectors described herein permit the delivery of smaller titers of viral particles in order to achieve the same transduction efficiency as that obtained using higher levels of conventional, non-surface capsid modified rAAV vectors. To that end, the amount of AAV compositions and time of administration of such compositions will be within the purview of the skilled artisan having benefit of the present teachings. In fact, the inventors contemplate that the administration of therapeutically-effective amounts of the disclosed compositions may be achieved by a single administration, such as for example, a single injection of sufficient numbers of infectious particles to provide therapeutic benefit to the patient undergoing such treatment. Alternatively, in some circumstances, it may be desirable to provide multiple, or successive administrations of the AAV vector compositions, either over a relatively short, or a relatively prolonged period of time, as may be determined by the medical practitioner overseeing the administration of such compositions. For example, the number of infectious particles administered to a mammal may be on the order of about $10^7$, $10^8$, $10^9$, $10^{10}$, $10^{11}$, $10^{12}$, $10^{13}$, or even higher, infectious particles/ml given either as a single dose, or divided into two or more administrations as may be required to achieve therapy of the particular disease or disorder being treated. In fact, in certain embodiments, it may be desirable to administer two or more different AAV vector compositions, either alone, or in combination with one or more other therapeutic drugs to achieve the desired effects of a particular therapy regimen. In most rAAV-based gene therapy regimens, the inventors believe that a lower titer of infectious particles will be required when using the modified-capsid rAAV vectors, than compared to conventional gene therapy protocols.

As used herein, the terms "engineered" and "recombinant" cells are intended to refer to a cell into which an exogenous polynucleotide segment (such as DNA segment that leads to the transcription of a biologically-active therapeutic agent) has been introduced. Therefore, engineered cells are distinguishable from naturally occurring cells, which do not contain a recombinantly introduced exogenous DNA segment. Engineered cells are, therefore, cells that comprise at least one or more heterologous polynucleotide segments introduced through the hand of man.

To express a therapeutic agent in accordance with the present invention one may prepare a tyrosine-modified rAAV expression vector that comprises a therapeutic agent-encoding nucleic acid segment under the control of one or more promoters. To bring a sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded polypeptide. This is the meaning of "recombinant expression" in this context. Particularly preferred recombinant vector constructs are those that comprise an rAAV vector. Such vectors are described in detail herein.

When the use of such vectors is contemplated for introduction of one or more exogenous proteins, polypeptides, peptides, ribozymes, and/or antisense oligonucleotides, to a particular cell transfected with the vector, one may employ the rAAV vectors or the tyrosine-modified rAAV vectors disclosed herein by genetically modifying the vectors to further comprise at least a first exogenous polynucleotide operably positioned downstream and under the control of at least a first heterologous promoter that expresses the polynucleotide in a cell comprising the vector to produce the encoded peptide, protein, polypeptide, ribozyme, siRNA, RNAi or antisense oligonucleotide. Such constructs may employ heterologous promoters that are constitutive, inducible, or even cell-specific promoters. Exemplary such promoters include, but are not limited to, viral, mammalian, and avian promoters, including for example a CMV promoter, a β-actin promoter, a hybrid CMV promoter, a hybrid β-actin promoter, an EF1 promoter, a U1a promoter, a U1b promoter, a Tet-inducible promoter, a VP16-LexA promoter, and such like.

The vectors or expression systems may also further comprise one or more enhancers, regulatory elements, transcriptional elements, to alter or effect transcription of the heterologous gene cloned in the rAAV vectors. For example, the rAAV vectors of the present invention may further comprise at least a first CMV enhancer, a synthetic enhancer, or a cell- or tissue-specific enhancer. The exogenous polynucleotide may also further comprise one or more intron sequences.

Pharmaceutical Compositions

The genetic constructs of the present invention may be prepared in a variety of compositions, and may also be formulated in appropriate pharmaceutical vehicles for administration to human or animal subjects. The rAAV molecules of the present invention and compositions comprising them provide new and useful therapeutics for the treatment, control, and amelioration of symptoms of a variety of disorders, and in particular, articular diseases, disorders, and dysfunctions, including for example osteoarthritis, rheumatoid arthritis, and related disorders. Moreover, pharmaceutical compositions comprising one or more of the nucleic acid compounds disclosed herein, provide significant advantages over existing conventional therapies—namely, (1) their reduced side effects, (2) their increased efficacy for prolonged periods of time, (3) their ability to increase patient compliance due to their ability to provide therapeutic effects following as little as a single administration of the selected therapeutic rAAV composition to affected individuals. Exemplary pharmaceutical compositions and methods for their administration are discussed in significant detail hereinbelow.

The invention also provides compositions comprising one or more of the disclosed rAAV vectors, expression systems, virions, viral particles; or mammalian cells. As described hereinbelow, such compositions may further comprise a pharmaceutical excipient, buffer, or diluent, and may be formulated for administration to an animal, and particularly a human being. Such compositions may further optionally comprise a liposome, a lipid, a lipid complex, a microsphere, a microparticle, a nanosphere, or a nanoparticle, or may be otherwise formulated for administration to the cells, tissues, organs, or body of a mammal in need thereof. Such compositions may be formulated for use in a variety of therapies, such as for example, in the amelioration, prevention, and/or treatment of conditions such as peptide deficiency, polypeptide deficiency, peptide overexpression, polypeptide overexpression, including for example, conditions which result in diseases or disorders such as cancers, tumors, or other malignant growths, neurological deficit dysfunction, autoimmune diseases, articular diseases, cardiac or pulmonary diseases, ischemia, stroke, cerebrovascular accidents, transient ischemic attacks (TIA); diabetes and/or other diseases of the pancreas; cardiocirculatory disease or dysfunction (including, e.g., hypotension, hypertension, atherosclerosis, hypercholesterolemia, vascular damage or disease; neural diseases (including, e.g., Alzheimer's, Huntington's, Tay-Sach's and Parkinson's disease, memory loss, trauma, motor impairment, neuropathy, and related disorders); biliary, renal or hepatic disease or dysfunction; musculoskeletal or neuromuscular diseases (including, e.g., arthritis, palsy, cystic fibrosis (CF), amyotrophic lateral sclerosis (ALS), multiple sclerosis (MS), muscular dystrophy (MD), and such like).

In certain embodiments, the present invention concerns formulation of one or more rAAV-based compositions disclosed herein in pharmaceutically acceptable solutions for administration to a cell or an animal, either alone or in combination with one or more other modalities of therapy, and in particular, for therapy of human cells, tissues, and diseases affecting man.

It will also be understood that, if desired, nucleic acid segments, RNA, DNA or PNA compositions that express one or more of therapeutic gene products may be administered in combination with other agents as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, given that the additional agents do not cause a significant adverse effect upon contact with the target cells or host tissues. The rAAV-based genetic compositions may thus be delivered along with various other agents as required in the particular instance. Such compositions may be purified from host cells or other biological sources, or alternatively may be chemically synthesized as described herein. Likewise, such compositions may further comprise substituted or derivatized RNA, DNA, siRNA, mRNA, tRNA, ribozyme, catalytic RNA molecules, or PNA compositions and such like.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, intra-articular, intramuscular administration and formulation.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound(s) in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the AAV vector-based therapeutic constructs in suitably formulated pharmaceutical compositions disclosed herein either subcutaneously, intraocularly, intravitreally, parenterally, subcutaneously, intravenously, intracerebro-ventricularly, intramuscularly, intrathecally, orally, intraperitoneally, by oral or nasal inhalation, or by direct injection to one or more cells, tissues, or organs by direct injection. The methods of administration may also include those modalities as described in U.S. Pat. No. 5,543,158; U.S. Pat. No. 5,641,515 and U.S. Pat. No. 5,399,363 (each specifically incorporated herein by reference in its entirety). Solutions of the active compounds as freebase or pharmacologically acceptable salts may be prepared in sterile water and may also suitably mixed with one or more surfactants, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms of the AAV-based viral compositions suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active AAV vector-delivered therapeutic polypeptide-encoding DNA fragments in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The AAV vector compositions disclosed herein may also be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

The amount of AAV compositions and time of administration of such compositions will be within the purview of the skilled artisan having benefit of the present teachings. It is likely, however, that the administration of therapeutically-effective amounts of the disclosed compositions may be achieved by a single administration, such as for example, a single injection of sufficient numbers of infectious particles to provide therapeutic benefit to the patient undergoing such treatment. Alternatively, in some circumstances, it may be desirable to provide multiple, or successive administrations of the AAV vector compositions, either over a relatively short, or a relatively prolonged period of time, as may be determined by the medical practitioner overseeing the administration of such compositions. For example, the number of infectious particles administered to a mammal may be on the order of about $10^7$, $10^8$, $10^9$, $10^{10}$, $10^{11}$, $10^{12}$, $10^{13}$, or even higher, infectious particles/ml given either as a single dose, or divided into two or more administrations as may be required to achieve therapy of the particular disease or disorder being treated. In fact, in certain embodiments, it may be desirable to administer two or more different AAV vector compositions, either alone, or in combination with one or more other therapeutic drugs to achieve the desired effects of a particular therapy regimen.

Expression Vectors

The present invention contemplates a variety of AAV-based expression systems, and vectors. In one embodiment the preferred AAV expression vectors comprise at least a first nucleic acid segment that encodes a therapeutic peptide, protein, or polypeptide. In another embodiment, the preferred AAV expression vectors disclosed herein comprise at least a first nucleic acid segment that encodes an antisense molecule. In another embodiment, a promoter is operatively linked to a sequence region that encodes a functional mRNA, a tRNA, a ribozyme or an antisense RNA.

The choice of which expression vector and ultimately to which promoter a polypeptide coding region is operatively linked depend directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the functional RNA to which it is operatively linked.

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

A variety of methods have been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

Therapeutic and Diagnostic Kits

The invention also encompasses one or more of the genetically-modified rAAV vector compositions described herein together with one or more pharmaceutically-acceptable excipients, carriers, diluents, adjuvants, and/or other components, as may be employed in the formulation of particular rAAV-polynucleotide delivery formulations, and in the preparation of therapeutic agents for administration to a mammal, and in particularly, to a human. In particular, such kits may comprise one or more of the disclosed rAAV compositions in combination with instructions for using the viral vector in the treatment of such disorders in a mammal, and may typically further include containers prepared for convenient commercial packaging.

As such, preferred animals for administration of the pharmaceutical compositions disclosed herein include mammals, and particularly humans. Other preferred animals include murines, bovines, equines, porcines, canines, and felines. The composition may include partially or significantly purified rAAV compositions, either alone, or in combination with one or more additional active ingredients, which may be obtained from natural or recombinant sources, or which may be obtainable naturally or either chemically synthesized, or alternatively produced in vitro from recombinant host cells expressing DNA segments encoding such additional active ingredients.

Therapeutic kits may also be prepared that comprise at least one of the compositions disclosed herein and instructions for using the composition as a therapeutic agent. The container means for such kits may typically comprise at least one vial, test tube, flask, bottle, syringe or other container means, into which the disclosed rAAV composition(s) may be placed, and preferably suitably aliquoted. Where a second therapeutic polypeptide composition is also provided, the kit may also contain a second distinct container means into which this second composition may be placed. Alternatively, the plurality of therapeutic biologically active compositions may be prepared in a single pharmaceutical composition, and may be packaged in a single container means, such as a vial, flask, syringe, bottle, or other suitable single container means. The kits of the present invention will also typically include a means for containing the vial(s) in close confinement for commercial sale, such as, e.g., injection or blow-molded plastic containers into which the desired vial(s) are retained.

RAAV Capsid Proteins

Supramolecular assembly of 60 individual capsid protein subunits into a non-enveloped, T-1 icosahedral lattice capable of protecting a 4.7-kb single-stranded DNA genome is a critical step in the life-cycle of the helper-dependent human parvovirus, adeno-associated virus2 (AAV2). The mature 20-nm diameter AAV2 particle is composed of three structural proteins designated VP1, VP2, and VP3 (molecular masses of 87, 73, and 62 kDa respectively) in a ratio of 1:1:18. Based on its symmetry and these molecular weight estimates, of the 60 capsid proteins comprising the particle, three are VP1 proteins, three are VP2 proteins, and fifty-four are VP3 proteins. The employment of three structural proteins makes AAV serotypes unique among parvoviruses, as all others known package their genomes within icosahedral particles composed of only two capsid proteins. The antiparallel β-strand barreloid arrangement of these 60 capsid proteins results in a particle with a defined tropism that is highly resistant to degradation. Modification of one or more tyrosine residues in one or more of the capsid proteins has been shown by the inventors to achieve superior transfection at lower dose and lower cost than conventional protocols. By site-specifically modifying one or more tyrosine residues on the surface of the capsid, the inventors have achieved significant improvement in transduction efficiency.

Nucleic Acid Amplification

In certain embodiments, it may be necessary to employ one or more nucleic acid amplification techniques to produce the nucleic acid segments of the present invention. Various methods are well-known to artisans in the field, including for example, those techniques described herein: Nucleic acid, used as a template for amplification, may be isolated from cells contained in the biological sample according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to nucleic acids corresponding to the ribozymes or conserved flanking regions are contacted with the isolated nucleic acid under conditions that permit selective hybridization. The term "primer", as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed.

Primers may be provided in double-stranded or single-stranded form, although the single-stranded form is preferred. Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (e.g., Affymax® technology). A number of template dependent processes are available to amplify the marker sequences present in a given template sample. One of the best-known amplification methods is the polymerase chain reaction (referred to as PCR™), which is described in detail in U.S. Pat. No. 4,683,195, U.S. Pat. No. 4,683,202 and U.S. Pat. No. 4,800,159 (each of which is incorporated herein by reference in its entirety).

Briefly, in PCR™, two primer sequences are prepared that are complementary to regions on opposite complementary strands of the marker sequence. An excess of deoxynucleoside triphosphates is added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al. (1989). Alternative methods for reverse transcription utilize thermostable, RNA-dependent DNA polymerases. These methods are described in Int. Pat. Appl. Publ. No. WO 90/07641 (specifically incorporated herein by reference). Polymerase chain reaction methodologies are well known in the art.

Another method for amplification is the ligase chain reaction ("LCR"), disclosed in EPA No. 320 308, and incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qβ Replicase (QβR), described in Int. Pat. Appl. No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[α-thio]-triphosphates in one strand of a restriction site may also be useful in the amplification of nucleic acids in the present invention.

Strand Displacement Amplification (SDA), described in U.S. Pat. Nos. 5,455,166, 5,648,211, 5,712,124 and 5,744,311, each incorporated herein by reference, is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in Int. Pat. Appl. No. PCT/US89/01025, each of which is incorporated herein by reference in its entirety, may be used in accordance with the present invention. In the former application, "modified" primers are used in a PCR™-like, template- and enzyme-dependent synthesis. The primers may be modified by labeling with a capture moiety (e.g., biotin) and/or a detector moiety (e.g., enzyme). In the latter application, an excess of labeled probes is added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR Gingeras et al., Int. Pat. Appl. Publ. No. WO 88/10315, incorporated herein by reference. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer that has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNAs are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (ds-DNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., Int. Pat. Appl. Publ. No. WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR™" (Frohman, 1990, specifically incorporated herein by reference).

Methods based on ligation of two (or more) oligonucleotides in the presence of nucleic acid having the sequence of the resulting "di-oligonucleotide," thereby amplifying the di-oligonucleotide, may also be used in the amplification step of the present invention.

Following any amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods (see e.g., Sambrook et al., 1989).

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography.

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols. See Sambrook et al., 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Biological Functional Equivalents

Modification and changes to the structure of the polynucleotides and polypeptides of wild-type rAAV vectors to provide the improved rAAV virions as described in the present invention to obtain functional viral vectors that possess desirable characteristics, particularly with respect to improved delivery of therapeutic gene constructs to selected mammalian cell, tissues, and organs for the treatment, prevention, and prophylaxis of various diseases and disorders, as well as means for the amelioration of symptoms of such diseases, and to facilitate the expression of exogenous therapeutic and/or prophylactic polypeptides of interest via rAAV vector-mediated gene therapy. As mentioned above, one of the key aspects of the present invention is the creation of one or more mutations into specific polynucleotide sequences that encode one or more of the therapeutic agents encoded by the disclosed rAAV constructs. In certain circumstances, the resulting polypeptide sequence is altered by these mutations, or in other cases, the sequence of the polypeptide is unchanged by one or more mutations in the encoding polynucleotide to produce modified vectors with improved properties for effecting gene therapy in mammalian systems.

When it is desirable to alter the amino acid sequence of a polypeptide to create an equivalent, or even an improved, second-generation molecule, the amino acid changes may be achieved by changing one or more of the codons of the encoding DNA sequence, according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the polynucleotide sequences disclosed herein, without appreciable loss of their biological utility or activity.

TABLE 1

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG CGU |
| Serine | Ser | S | AGC | AGU | UCA | UCC | UCG UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/ cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those that are within ±1 are particularly preferred, and those within ±0.5 are even more particularly preferred. It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take several of the foregoing characteristics into consideration are well known to those of skill in the art and include: arginine and lysine; glutamate and aspartate; serine and threonine; glutamine and asparagine; and valine, leucine and isoleucine.

EXEMPLARY DEFINITIONS

In accordance with the present invention, polynucleotides, nucleic acid segments, nucleic acid sequences, and the like, include, but are not limited to, DNAs (including and not limited to genomic or extragenomic DNAs), genes, peptide nucleic acids (PNAs) RNAs (including, but not limited to, rRNAs, mRNAs and tRNAs), nucleosides, and suitable nucleic acid segments either obtained from natural sources, chemically synthesized, modified, or otherwise prepared or synthesized in whole or in part by the hand of man.

Unless defined otherwise, all technical and scientific terms used herein have the same meaning as commonly understood by one of ordinary skill in the art to which this invention belongs. Although any methods and compositions similar or equivalent to those described herein can be used in the practice or testing of the present invention, the preferred methods and compositions are described herein. For purposes of the present invention, the following terms are defined below:

A, an: In accordance with long standing patent law convention, the words "a" and "an" when used in this application, including the claims, denotes "one or more."

Expression: The combination of intracellular processes, including transcription and translation undergone by a polynucleotide such as a structural gene to synthesize the encoded peptide or polypeptide.

Promoter: a term used to generally describe the region or regions of a nucleic acid sequence that regulates transcription.

Regulatory Element: a term used to generally describe the region or regions of a nucleic acid sequence that regulates transcription. Exemplary regulatory elements include, but are not limited to, enhancers, post-transcriptional elements, transcriptional control sequences, and such like.

Structural gene: A polynucleotide, such as a gene, that is expressed to produce an encoded peptide, polypeptide, protein, ribozyme, catalytic RNA molecule, siRNA, or antisense molecule.

Transformation: A process of introducing an exogenous polynucleotide sequence (e.g., a viral vector, a plasmid, or a recombinant DNA or RNA molecule) into a host cell or protoplast in which the exogenous polynucleotide is incorporated into at least a first chromosome or is capable of autonomous replication within the transformed host cell. Transfection, electroporation, and "naked" nucleic acid uptake all represent examples of techniques used to transform a host cell with one or more polynucleotides.

Transformed cell: A host cell whose nucleic acid complement has been altered by the introduction of one or more exogenous polynucleotides into that cell.

Transgenic cell: Any cell derived or regenerated from a transformed cell or derived from a transgenic cell, or from the progeny or offspring of any generation of such a transformed host cell.

Vector: A nucleic acid molecule (typically comprised of DNA) capable of replication in a host cell and/or to which another nucleic acid segment can be operatively linked so as to bring about replication of the attached segment. A plasmid, cosmid, or a virus is an exemplary vector.

The terms "substantially corresponds to," "substantially homologous," or "substantial identity," as used herein, denote a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared.

The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides.

Desirably, which highly homologous fragments are desired, the extent of percent identity between the two sequences will be at least about 80%, preferably at least about 85%, and more preferably about 90% or 95% or higher, as readily determined by one or more of the sequence comparison algorithms well-known to those of skill in the art, such as e.g., the FASTA program analysis described by Pearson and Lipman (*Proc. Natl. Acad. Sci. USA*, 85(8): 2444-8, April 1988).

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by the hand of man in a laboratory is naturally-occurring. As used herein, laboratory strains of rodents that may have been selectively bred according to classical genetics are considered naturally occurring animals.

As used herein, a "heterologous" is defined in relation to a predetermined referenced gene sequence. For example, with respect to a structural gene sequence, a heterologous promoter is defined as a promoter which does not naturally occur adjacent to the referenced structural gene, but which is positioned by laboratory manipulation. Likewise, a heterologous gene or nucleic acid segment is defined as a gene or segment that does not naturally occur adjacent to the referenced promoter and/or enhancer elements.

"Transcriptional regulatory element" refers to a polynucleotide sequence that activates transcription alone or in combination with one or more other nucleic acid sequences. A transcriptional regulatory element can, for example, comprise one or more promoters, one or more response elements, one or more negative regulatory elements, and/or one or more enhancers.

As used herein, a "transcription factor recognition site" and a "transcription factor binding site" refer to a polynucleotide sequence(s) or sequence motif(s) which are identified as being sites for the sequence-specific interaction of one or more transcription factors, frequently taking the form of direct protein-DNA binding. Typically, transcription factor binding sites can be identified by DNA footprinting, gel mobility shift assays, and the like, and/or can be predicted on the basis of known consensus sequence motifs, or by other methods known to those of skill in the art.

As used herein, the term "operably linked" refers to a linkage of two or more polynucleotides or two or more nucleic acid sequences in a functional relationship. A nucleic acid is "operably linked" when it is placed into a functional relationship with another nucleic acid sequence. For instance, a promoter or enhancer is operably linked to a coding sequence if it affects the transcription of the coding sequence. "Operably linked" means that the nucleic acid sequences being linked are typically contiguous, or substantially contiguous, and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

"Transcriptional unit" refers to a polynucleotide sequence that comprises at least a first structural gene operably linked to at least a first cis-acting promoter sequence and optionally linked operably to one or more other cis-acting nucleic acid sequences necessary for efficient transcription of the structural gene sequences, and at least a first distal regulatory element as may be required for the appropriate tissue-specific and developmental transcription of the structural gene sequence operably positioned under the control of the promoter and/or enhancer elements, as well as any additional cis sequences that are necessary for efficient transcription and translation (e.g., polyadenylation site(s), mRNA stability controlling sequence(s), etc.

The term "substantially complementary," when used to define either amino acid or nucleic acid sequences, means that a particular subject sequence, for example, an oligonucleotide sequence, is substantially complementary to all or a portion of the selected sequence, and thus will specifically bind to a portion of an mRNA encoding the selected sequence. As such, typically the sequences will be highly complementary to the mRNA "target" sequence, and will have no more than about 1, 2, 3, 4, 5, 6, 7, 8, 9, or 10 base mismatches throughout the complementary portion of the sequence. In many instances, it may be desirable for the sequences to be exact matches, i.e. be completely complementary to the sequence to which the oligonucleotide specifically binds, and therefore have zero mismatches along the complementary stretch. As such, highly complementary sequences will typically bind quite specifically to the target sequence region of the mRNA and will therefore be highly efficient in reducing, and/or even inhibiting the translation of the target mRNA sequence into polypeptide product.

Substantially complementary oligonucleotide sequences will be greater than about 80 percent complementary (or '% exact-match') to the corresponding mRNA target sequence to which the oligonucleotide specifically binds, and will, more preferably be greater than about 85 percent complementary to the corresponding mRNA target sequence to which the oligonucleotide specifically binds. In certain aspects, as described above, it will be desirable to have even more substantially complementary oligonucleotide sequences for use in the practice of the invention, and in such instances, the oligonucleotide sequences will be greater than about 90 percent complementary to the corresponding mRNA target sequence to which the oligonucleotide specifically binds, and may in certain embodiments be greater than about 95 percent complementary to the corresponding mRNA target sequence to which the oligonucleotide specifically binds, and even up to and including 96%, 97%, 98%, 99%, and even 100% exact match complementary to all or a portion of the target mRNA to which the designed oligonucleotide specifically binds.

Percent similarity or percent complementary of any of the disclosed sequences may be determined, for example, by comparing sequence information using the GAP computer program, version 6.0, available from the University of Wisconsin Genetics Computer Group (UWGCG). The GAP program utilizes the alignment method of Needleman and Wunsch (*J. Mol. Biol.,* 48(3):443-53, 1970). Briefly, the GAP program defines similarity as the number of aligned symbols (i.e., nucleotides or amino acids) that are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess (*Nucl. Acids Res.,* 14:6745-6763, 1986), (2) a penalty of 3.0 for each gap and an additional 0.10 penalty for each symbol in each gap; and (3) no penalty for end gaps.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human, and in particular, when administered to the human eye. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

As used herein, the term "operatively linked" means that a promoter is connected to a functional RNA in such a way that the transcription of that functional RNA is controlled and regulated by that promoter. Means for operatively linking a promoter to a functional RNA are well known in the art.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1 AAV2-Mediated Gene Transfer: A Dual Role of EGFR Protein Tyrosine Kinase Signaling in Ubiquitination of Viral Capsids and Viral Second-Strand DNA Synthesis The adeno-associated virus 2 (AAV2), a non-pathogenic human parvovirus, has gained attention as an alternative to the more commonly used retrovirus- and adenovirus-based vectors for gene transfer and gene therapy[1, 2]. Recombinant AAV2 vectors are currently in use in Phase I/II clinical trials for gene therapy of a number of diseases such as cystic fibrosis, α-1 antitrypsin deficiency, Parkinson's disease, Batten's disease, and muscular dystrophy,[3, 4, 5] and have been shown to transduce a wide variety of cells and tissues in vitro and in vivo.[2, 6-8] Systematic studies have been exploited to elucidate some of the fundamental steps in the life cycle of AAV vectors, which include viral binding, entry,[9-13] intracellular trafficking,[14-17] uncoating,[18, 19] second-strand DNA synthesis,[20-28] and viral genome integration into host cell chromosome.[29, 30]

Two independent laboratories have described that the viral second-strand DNA synthesis is a rate-limiting step, which accounts for inefficient transduction of certain cell types by AAV vectors.[20, 21] The inventors have also demonstrated that a cellular protein (designated FKBP52), which interacts with the single-stranded D-sequence in the AAV2 inverted terminal repeat (ITR), is phosphorylated at tyrosine residues by the epidermal growth factor receptor protein tyrosine kinase (EGFR-PTK), and inhibits the viral second-strand DNA synthesis leading to inefficient transgene expression,[24] It has also been documented that FKBP52 is dephosphorylated at tyrosine residues by T-cell protein tyrosine phosphatase (TC-PTP), which negatively regulates EGFR-PTK signaling, leading to efficient viral second-strand DNA synthesis.[25] Tyrosine-dephosphorylation of FKBP52 in TC-PTP-transgenic (TC-PTP TG) mice, and removal of FKBP52 in FKBP52 knockout (FKBP52-KO) mice also lead to efficient AAV2 transduction of murine hepatocytes in vivo.

An additional rate-limiting step in AAV-mediated transduction, viral intracellular trafficking, has also become apparent, and is being studied extensively. The ubiquitin-proteasome pathway has been shown to play an essential role in this step. AAV2 is likely to be degraded if it fails to escape the late endosome. If the virus escapes into the cytoplasm perinuclearly, it may be ubiquitinated and degraded by the cytoplasmic proteasome.[16, 31-32] In previous studies with murine fibroblast,[14, 15] it was documented that AAV2 vectors failed to traffic to the nucleus efficiently, but over-expression of TC-PTP in TC-PTP-TG mice facilitated this process.[19] These studies suggested that TC-PTP and/or EGFR-PTK signaling were involved in AAV2 intracellular trafficking.

In the present studies, the role of EGFR-PTK signaling in ubiquitination, intracellular trafficking, and AAV-mediated transgene expression was systematically examined. It was demonstrated that in addition to augmenting viral second-strand DNA synthesis, perturbations in EGFR-PTK signaling affects AAV2 transduction efficiency by facilitating intracellular trafficking from cytoplasm to nucleus. Since the free ubiquitin content within a cell that regulates lysosomal degradation of EGFR, with proteasome inhibitors affect receptor endocytosis,[33] proteasome inhibitors augment AAV transduction,[16, 31-35] and protein phosphorylation modulates ubiquitination of cellular and viral proteins,[36-42] evidence is presented documenting that inhibition of EGFR-PTK signaling decreases ubiquitination of AAV2 capsid proteins, suggesting that ubiquitination followed by proteasome-mediated degradation of AAV2 capsid proteins is also affected by EGFR-PTK. These studies suggest that complex interactions between EGFR-PTK signaling and ubiquitin/proteasome pathway play a role in AAV-mediated transduction, which is likely to be important in yielding new insights in the optimal use of recombinant AAV vectors in human gene therapy.

Materials and Methods

Cells, Viruses, Plasmids, Antibodies, and Chemicals.

The human cervical carcinoma cell line, HeLa, was obtained from the American Type Culture Collection (ATCC, Rockville, Md., USA), and maintained as monolayer cultures in Iscove's-modified Dulbecco's medium (IMDM) supplemented with 10% newborn calf serum (NCS) and 1% (by volume) of 100× stock solution of antibiotics (10,000 U penicillin+10,000 μg streptomycin). Highly-purified stocks of ss recombinant AAV2 vectors containing the β-galactosidase (lacZ) reporter gene, or red fluorescence protein (RFP) gene, or ss and sc recombinant AAV2 vectors containing enhanced green fluorescence protein (EGFP) gene driven by the cytomegalovirus (CMV) immediate-early promoter (ssAAV2-lacZ, ssAAV2-RFP, ssAAV2-EGFP or scAAV2-EGFP) were generated as described previously.[49]

Physical particle titers of recombinant vector stocks were determined by quantitative DNA slot blot analysis. Horseradish peroxidase (HRP)-conjugated antibody specific for ubiquitin (Ub) (mouse monoclonal immunoglobulin $G_1$ [$IgG_1$], clone P4D1), and normal mouse $IgG_1$ were purchased from Santa Cruz Biotechnology (Santa Cruz, Calif., USA). Antibodies specific for intact AAV2 particles (mouse monoclonal $IgG_1$, clone A20) was obtained from Research Diagnostics, Inc., (Flanders, N.J., USA). MG132 was purchased from Calbiochem (La Jolla, Calif., USA), and all other chemicals used were purchased from Sigma-Aldrich Co. (St. Louis, Mo. USA).

Recombinant AAV Vector Transduction Assay.

Approximately $1 \times 10^5$ HeLa cells were plated in each well in 12-well plates and incubated at 37° C. for 12 hr. Cells were washed once with IMDM and then infected at 37° C. for 2 hr with $5 \times 10^3$ particles per cell of recombinant AAV2-lacZ, ssAAV2-EGFP or scAAV2-EGFP vectors as described previously.[24, 26, 28] Cells were incubated in complete IMDM containing 10% NCS and 1% antibiotics for 48 hr. For lacZ expression, cells were fixed and stained with X-Gal (5-bromo-4-chloro-indolyl-β-D-galactopyranoside). The transduction efficiency was measured by GFP imaging using a LEICA DM IRB/E fluorescence microscope (Leica Microsystems Wetzlar GmbH, Germany). Images from three visual fields of mock-infected and vector-infected HeLa cells at 48 hr post-injection were analyzed quantitatively by ImageJ analysis software (NIH, Bethesda, Md., USA). Transgene expression was assessed as total area of green fluorescence (pixel$^2$) per visual field (mean±SD). Analysis of variance (ANOVA) was used to compare between test results and the control and they were determined to be statistically significant.

Isolation of Nuclear and Cytoplasmic Fractions from HeLa Cells.

Nuclear and cytoplasmic fractions from HeLa cells were isolated as described previously.[19] Cells were mock-infected or infected with recombinant AAV2-lacZ vectors were washed twice with PBS 12 hr post-infection. Cells were treated with 0.01% trypsin and washed extensively with PBS to remove any adsorbed and unadsorbed virus particles. Cell pellets were gently resuspended in 200 μl hypotonic buffer (10 mM HEPES, pH 7.9. 1.5 mM $MgCl_2$, 10 mM KCl, 0.5 mM DTT, 0.5 mM PMSF) and incubated on ice for 5 min, after which 10 μl 10% NP-40 was added to each tube for ~3 min, and observed under a light microscope. Samples were mixed gently and centrifuged for 5 min at 500 rpm at 4° C. Supernatants (cytoplasmic fractions) were decanted and stored on ice. Pellets (nuclear fractions) were washed twice with 1 ml hypotonic buffer and stored on ice. The purity of each fraction was determined to be >95%, as measured by the absence of acid phosphatase activity (nuclear fractions) and absence of histone H3 (cytoplasmic fractions) as described previously.[14, 19]

Southern Blot Analysis for AAV Trafficking.

Low $M_r$ DNA samples from nuclear and cytoplasmic fractions were isolated and electrophoresed on 1% agarose gels or 1% alkaline-agarose gels followed by Southern blot hybridization using a $^{32}$P-labeled lacZ-specific DNA probe as described previously.[14, 19] Densitometric scanning of autoradiographs for the quantitation was evaluated with ImageJ® analysis software (National Institutes of Health, Bethesda, Md., USA).

Preparation of Whole Cell Lysates (WCL) and Co-Immunoprecipitation.

WCL were prepared as described previously,[17, 26, 50] with the following modifications: briefly, $2 \times 10^6$ HeLa cells were either mock-treated, or treated with 500 mM Tyr23, 4 mM MG132, or both (treatment with MG132 for 2 hr and then with Try23 for an additional 2 hr) for 4 hr. Cells were mock-infected or infected with ssAAV-RFP vectors at $10^4$ particles/cell for 2 hr at 37° C. Mock-transfected cells and cells stably transfected with wt- or mTC-PTP expression plasmids were treated with MG132 and also subjected to mock-infection or infection with ssAAV-RFP vectors.

For cellular protein analyses, treated or mock-treated cells were lysed on ice in cell lysis buffer (1% Triton X-100®, 10% glycerol, 50 mM HEPES, pH 7.5, 150 mM NaCl, 1.5 mM $MgCl_2$, 1 mM EDTA) containing 1 mM DTT, 10 mM NaF, 2 mM $Na_3VO_4$, 0.5 mM PMSF, 10 mg/ml aprotinin, 10 mg/ml leupeptin and 10 mg/ml pepstatin. For immunoprecipitation, cells were treated with 0.01% trypsin and washed extensively with PBS to remove any adsorbed and unadsorbed virus particles after treatment or at 4 hr post-infection and then resuspended in 2 ml hypotonic buffer (20 mM HEPES pH 7.5, 5 mM KCl, 0.5 mM $MgCl_2$) containing 1 mM DTT, 10 mM NaF, 2 mM $Na_3VO_4$, 0.5 mM PMSF, 10 mg/ml aprotinin, 10 mg/ml leupeptin and 10 mg/ml. WCL was prepared by homogenization in a tight-fitting Duall tissue grinder until about 95% cell lysis was achieved as monitored by trypan blue dye exclusion assay. WCL were cleared of non-specific binding by incubation with 0.25 mg of normal mouse $IgG_1$ together with 20 ml of protein G-agarose beads for 60 min at 4° C. in an orbital shaker.

After preclearing, 2 mg of capsid antibody against intact AAV2 particles (A20) (mouse $IgG_1$) or 2 mg of normal mouse $IgG_1$ (as a negative control) was added and incubated at 4° C. for 1 hr, followed by precipitation with protein G-agarose beads at 4° C. for 12 hr in a shaker. Pellets were collected by centrifugation at 2,500 rpm for 5 min at 4° C.

and washed four times with PBS. After the final wash, supernatants were aspirated and discarded, and pellets were resuspended in equal volume of 2×SDS sample buffer. Twenty ml of resuspended pellet solutions were used for Western blotting with HRP-conjugated anti-Ub antibody as described below.

Western Blot Analyses.

Western blotting was performed as described previously.[17, 26, 50] For cellular protein analyses, equivalent amounts (~5 mg) WCL samples were separated by 10% SDS-polyacrylamide gel electrophoresis (SDS-PAGE) and transferred to Immobilon-P® membranes (Millipore, Bedford, Mass., USA). For immunoprecipitation, resuspended pellet solutions were boiled for 2-3 min and 20 ml of samples were used for SDS-PAGE. Membranes were blocked at 4° C. for 12 hr with 5% nonfat milk in 1× Tris-buffered saline (TBS, 20 mM Tris-HCl, pH 7.5, 150 mM NaCl). Membranes were treated with monoclonal HRP-conjugated anti-Ub antibody (1:2,000 dilution). Immunoreactive bands were visualized using chemiluminescence (ECL-Plus™, Amersham Pharmacia Biotech, Piscataway, N.J., USA).

Results

Inhibition of EGFR-PTK Signaling Increases EGFP Transgene Expression Following Transduction with Both ssAAV2 and scAAV2 Vectors.

In previously-published studies,[23-25, 27, 43] the inventors and their collaborators have documented that the inhibition of EGFR-PTK signaling leads to dephosphorylation of FKBP52 at tyrosine residues, and facilitates viral second-strand DNA synthesis resulting in efficient transgene expression. Since double-stranded scAAV2 vectors,[44, 45] which bypass the requirement for second-strand DNA synthesis, achieve much higher transduction efficiency, the following predication was assessed: scAAV2-mediated transgene expression should not be influenced by the inhibition of EGFR-PTK signaling if viral second-strand DNA synthesis is the sole mechanism involved. In the first set of studies, HeLa cells were treated with Tyr23, a specific inhibitor of EGFR-PTK[43], transduced with recombinant ssAAV2-EGFP or scAAV2-EGFP vectors, and transgene expression was determined 48 hr post-transduction.

Figure 1A:
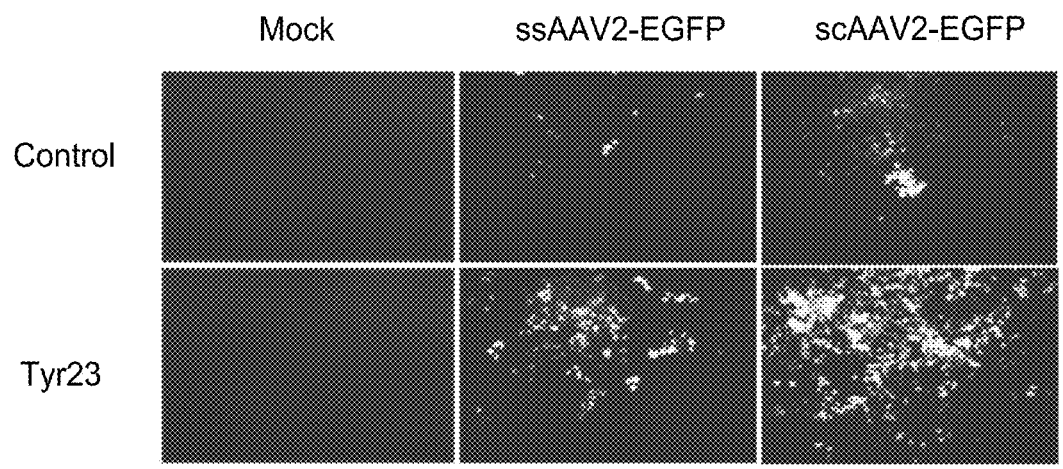
FIG. 1A and FIG. 1B show the AAV2-mediated transgene expression in HeLa cells, pre-treated with or without Tyr23, following transduction with either ssAAV2-EGFP or scAAV2-EGFP vectors.
Figure 1B:
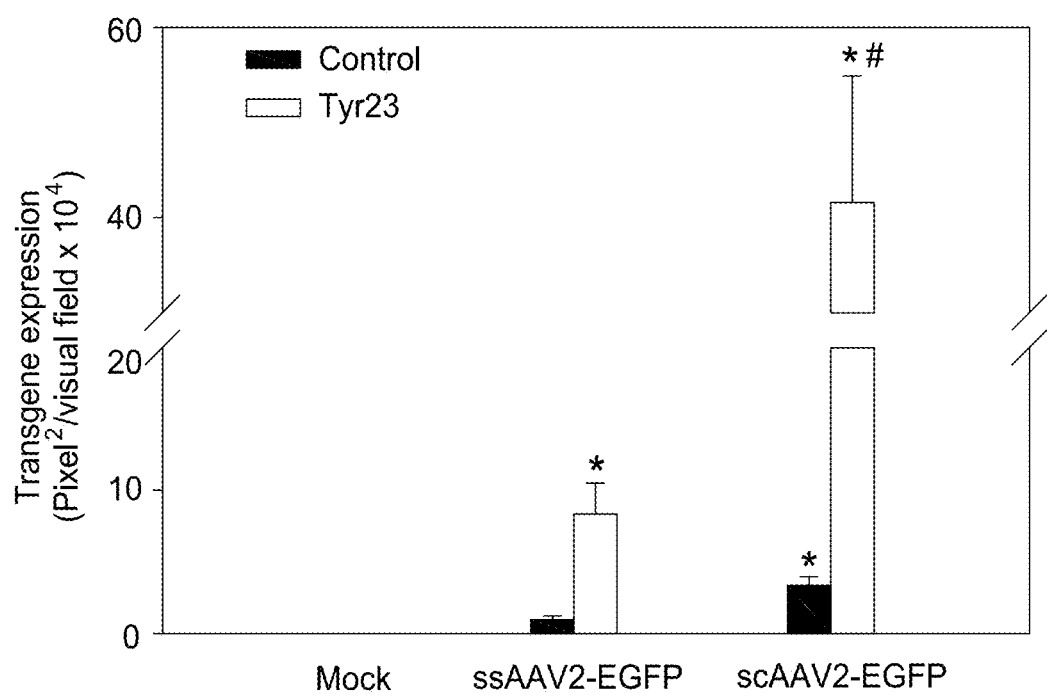

From the results shown in FIG. 1A, it is evident that whereas mock-infected HeLa cells showed no green fluorescence, only ~3% of HeLa cells transduced with the ssAAV2-EGFP vector were EGFP-positive, and Tyr23 treatment led to ~12-fold increase in ssAAV transduction efficiency (FIG. 1B), consistent with earlier results[23-25, 27, 43]. Although the transduction efficiency of rAAV vectors was ~4-fold higher compared with that of their single-stranded counterparts, as expected, but surprisingly, Tyr23 treatment also led to a further ~10-fold increase in the transduction efficiency of rAAV vectors (FIG. 1B).

This increase was not due to contamination of rAAV vectors with ssAAV vectors, the generation of which has been recently documented[46]. These data, nonetheless, suggested that perturbations in EGFR signaling affect additional aspects of AAV-mediated transduction beyond viral second-strand DNA synthesis.

Figure 2A:
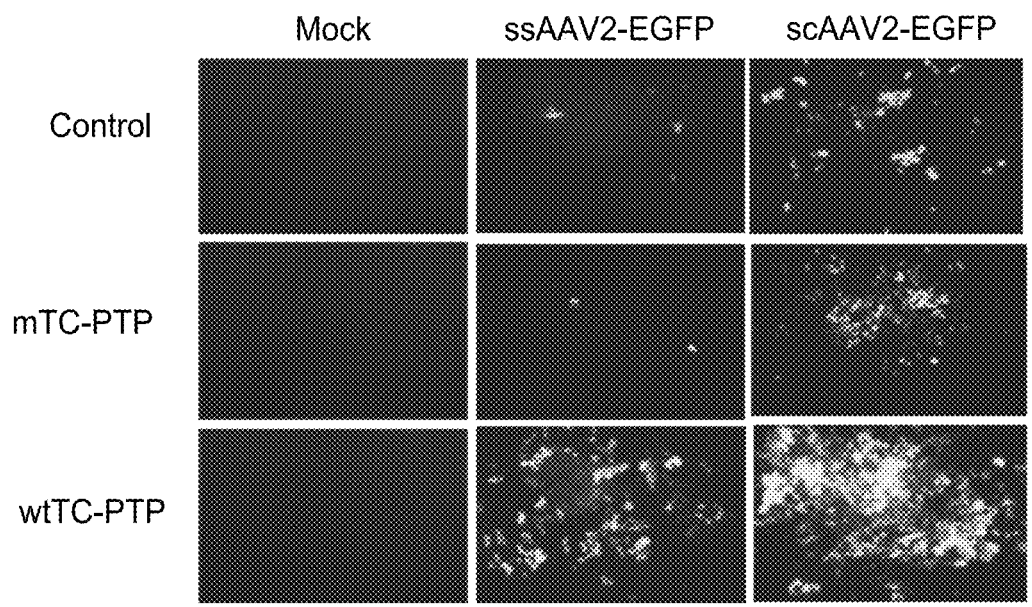
FIG. 2A and FIG. 2B illustrate the AAV-mediated transgene expression in HeLa cells mock-transfected, or stably transfected with wt- or C-S mutant TC-PTP expression plasmids, following transduction with either ssAAV2-EGFP or scAAV2-EGFP vectors.

Since stable transfection with a TC-PTP expression plasmid leads to inhibition of EGFR-PTK signaling and efficient transgene expression mediated by ssAAV vectors[25], it was reasoned that deliberate over-expression of TC-PTP would also lead to a significant increase in transduction efficiency of scAAV2 vectors. HeLa cells were either mock-transfected or stably transfected with the wild-type (wt)- or a C-S mutant (m)-TC-PTP expression plasmid, and were infected with ssAAV2-EGFP or scAAV2-EGFP vectors, and transgene expression was visualized 48-hrs' post-infection. As can be seen in FIG. 2A, whereas mock-infected HeLa cells showed no green fluorescence, and only ~3% of mock-transfected cells transduced with ssAAV-EGFP vector were EGFP-positive, a significantly increase (~15-fold) in transduction efficiency of ssAAV2 vectors in cells stably transfected with the wtTC-PTP expression plasmid was obtained, consistent with previously published reports[22, 27]. This increase was not observed when the mTC-PTP expression plasmid was used.

Figure 2B:
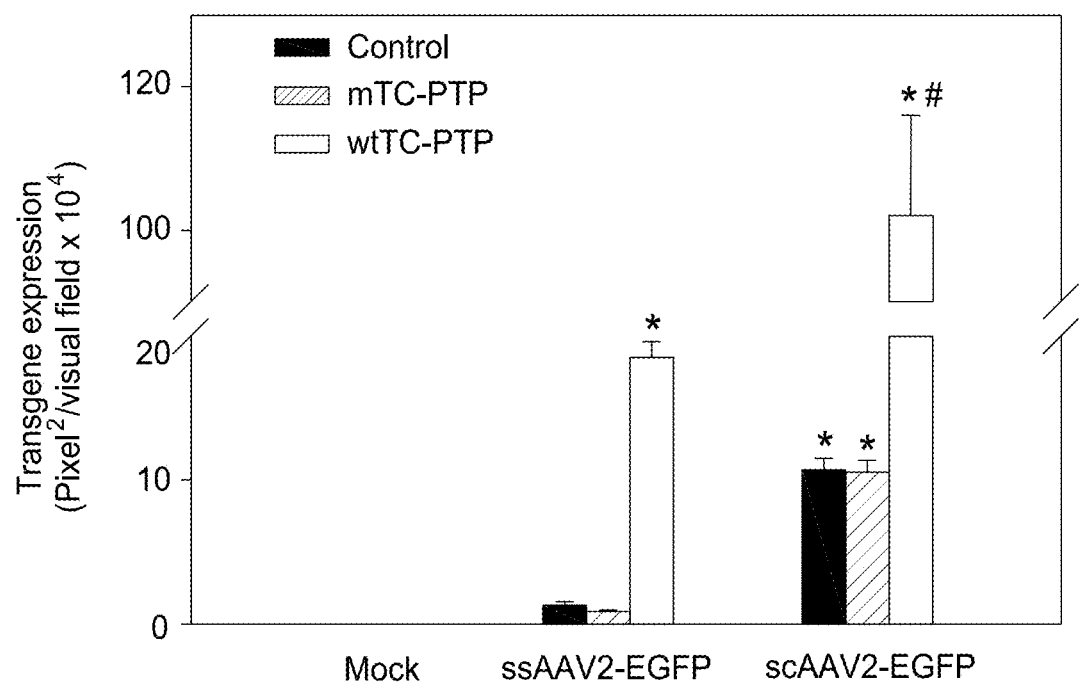

It is noteworthy that although the transduction efficiency of scAAV2 vectors in HeLa cells is ~8-fold higher compared with their ss counterparts, stably transfection with the wtTC-PTP expression plasmid leads to a further ~10-fold increase (FIG. 2B). These data corroborate that inhibition of EGFR-PTK signaling by pre-treatment with Tyr23 or over-expression of TC-PTP augments AAV2 transduction involves other mechanism(s) in addition to facilitating viral second-strand DNA synthesis.

Nuclear Transport of AAV is Improved Following Pre-Treatment with Tyr23, Over-Expression of wtTC-PTP, or Proteasome Inhibitor, MG132.

Figure 3A:
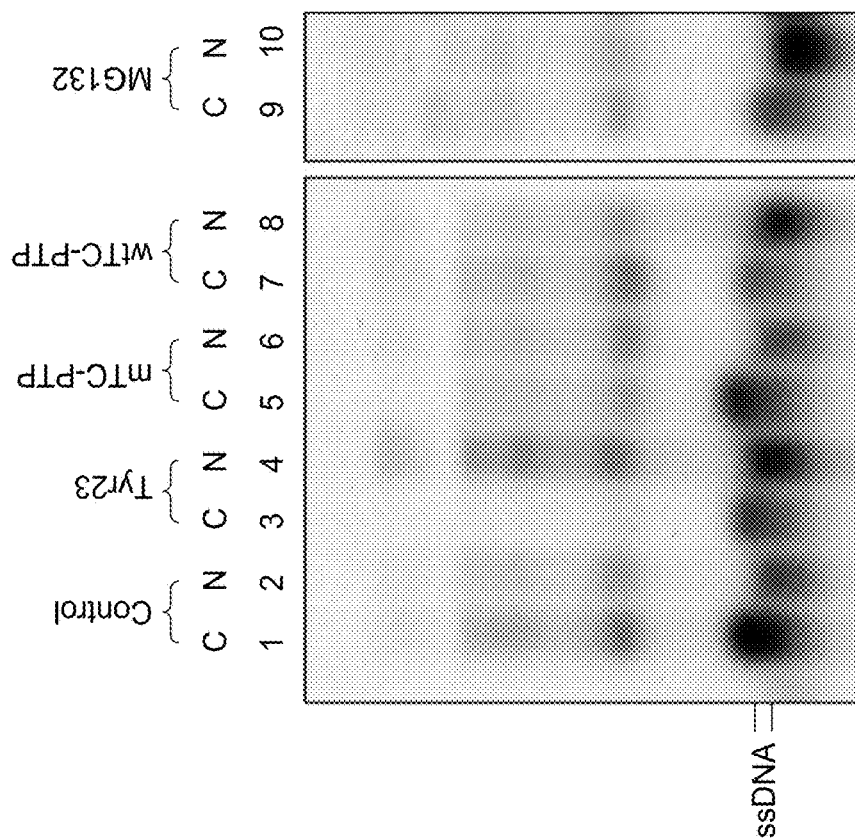
FIG. 3A and FIG. 3B show Southern blot analyses of cytoplasmic and nuclear distribution of AAV2 genomes in HeLa cells following pre-treatment with Tyr23, over-expression of wtTC-PTP, or treatment with MG132 (FIG. 3A), and densitometric scanning of autoradiographs for the quantitation of relative amounts of viral genomes (FIG. 3B). These results are representative of two independent studies.
Figure 3B:
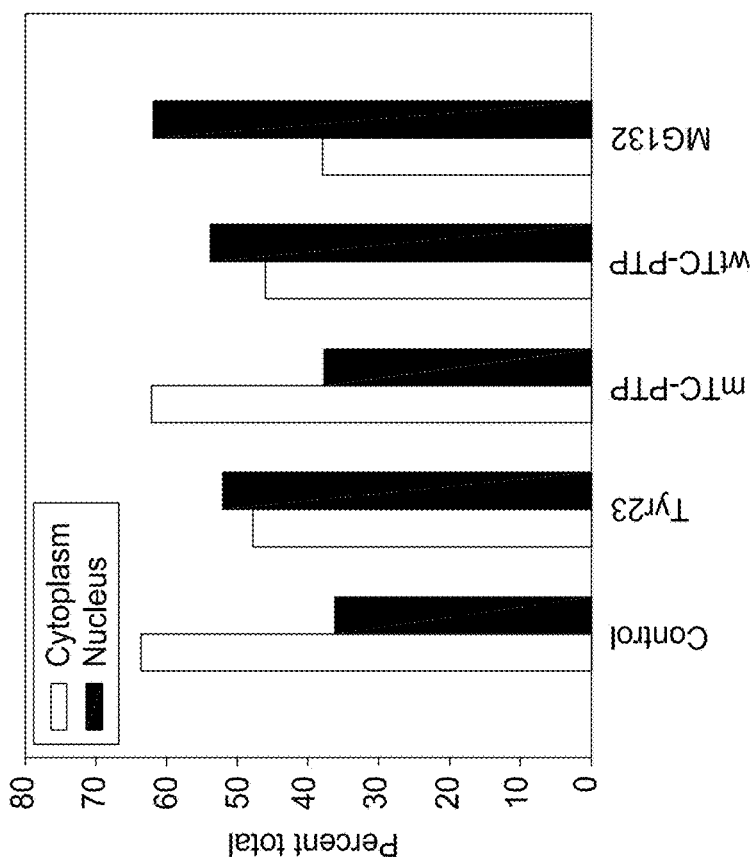

It was previously documented that over-expression of TC-PTP in TC-PTP-TG mice facilitated AAV2 vector transport to the nucleus in primary murine hematopoietic cells,[19] which suggested that EGFR-PTK signaling might also be involved in AAV trafficking. To further examine this hypothesis, the fate of the input viral DNA was examined in cells treated with Tyr23, or stably transfected with the wtTC-PTP. Mock-treated cells, cells stably transfected with mTC-PTP, and cells treated with MG132, a specific inhibitor of proteasome,[16, 31, 32] known to augment AAV nuclear transport,[16, 34, 35] were used as appropriate controls. Nuclear and cytoplasmic fractions were obtained 12 hr post-infection, low $M_r$ DNA was isolated from these fractions, and were electrophoresed on 1% agarose gels followed by Southern blot analysis (FIG. 3A) and densitometric scanning of autoradiographs (FIG. 3B).

Figure 9:
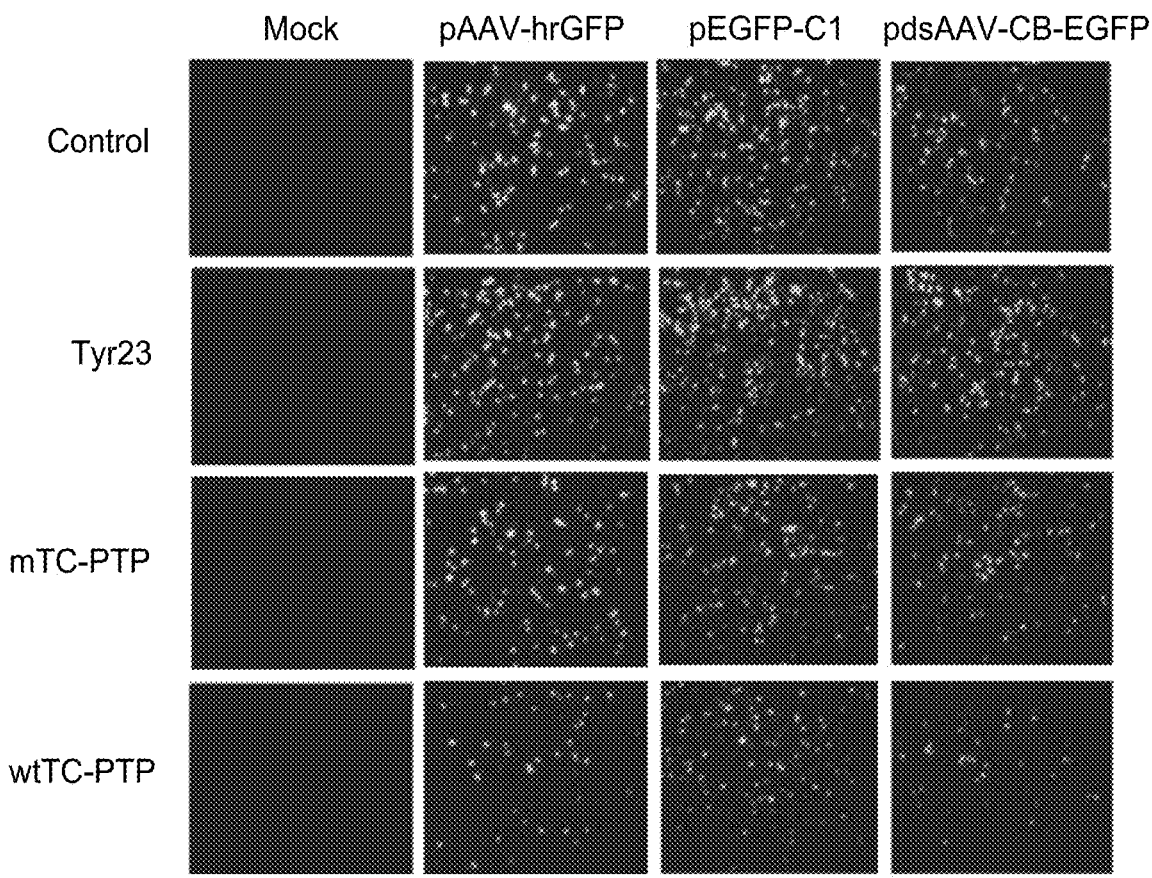
FIG. 9 shows the tyrosine-dephosphorylation of FKBP52, either by pre-treatment with Tyr23 or over-expression of TC-PTP, does not affect GFP gene expression following plasmid-mediated transfection in HeLa cells.
Figure 13:
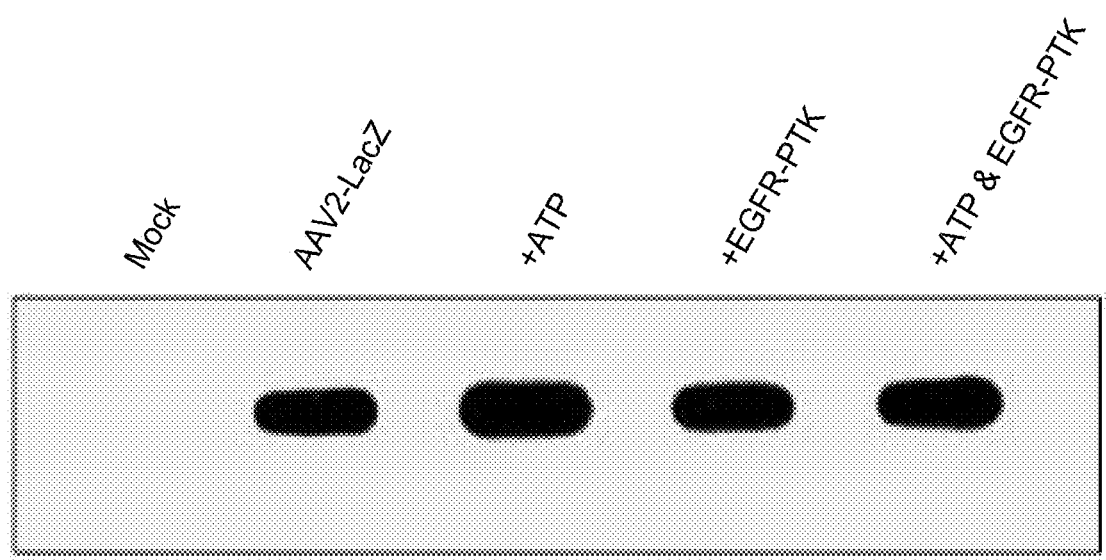
FIG. 13 shows the slot blot analysis for AAV2 entry to HeLa cells after in vitro phosphorylation of AAV capsids by EGFR-PTK. HeLa cells were infected by AAV2-LacZ vectors, which were pre-incubated with ATP, EGFR-TPK or both. Low-$M_r$ DNA samples were isolated at 2 hr post-infection and analyzed by Slot blot hybridization using a $^{32}$P-labeled LacZ DNA probe.
Figure 10A:
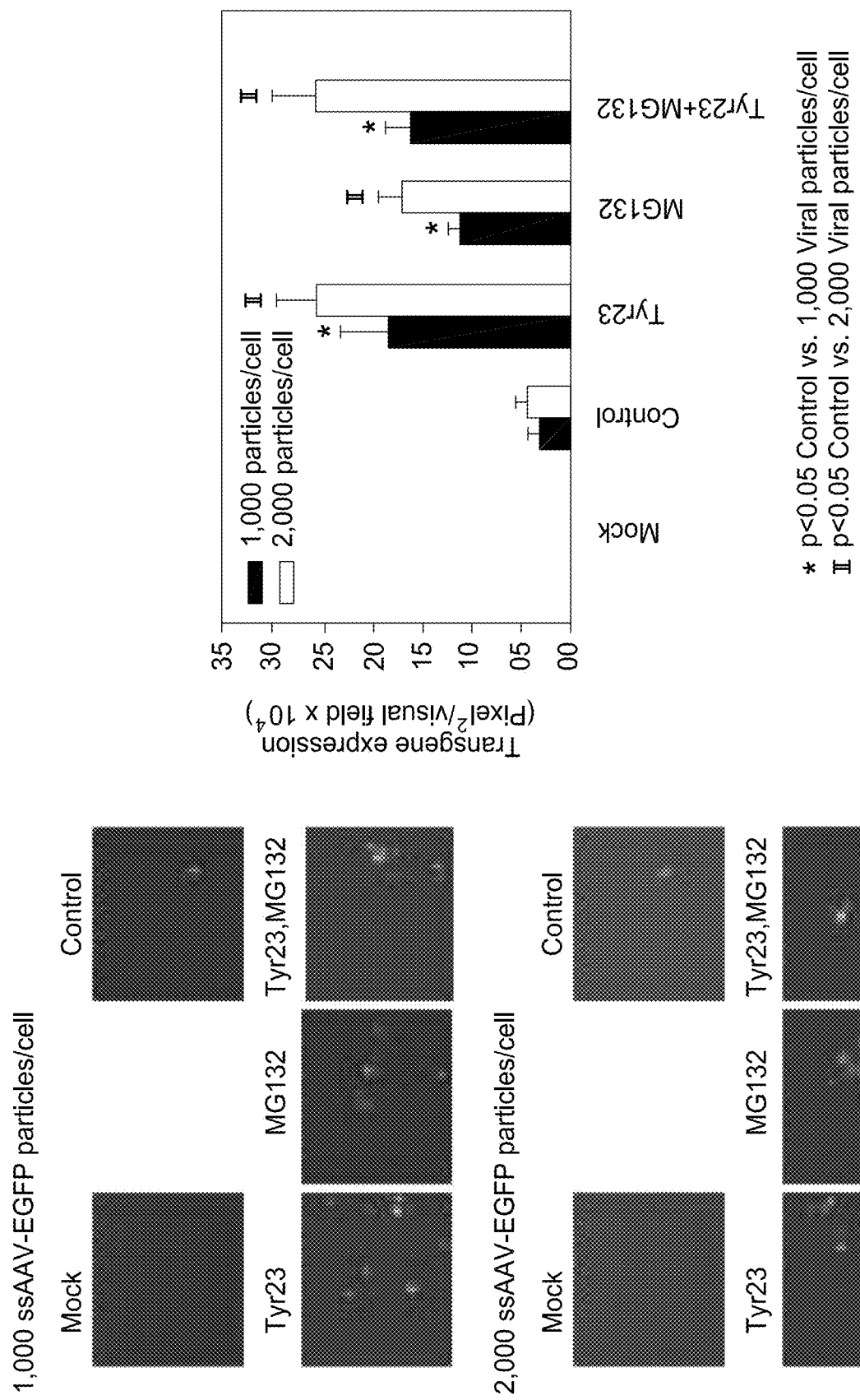
FIG. 10A and FIG. 10B show the transduction efficiency of neither ssAAV (FIG. 10A) nor rAAV vectors (FIG. 10B) in HeLa cells over-expressing TC-PTP, or following pre-treatment with Tyr23, was further enhanced by treatment with MG132 under non-saturating conditions (1,000 or 2,000 viral particles/cell) of transduction.
Figure 10B:
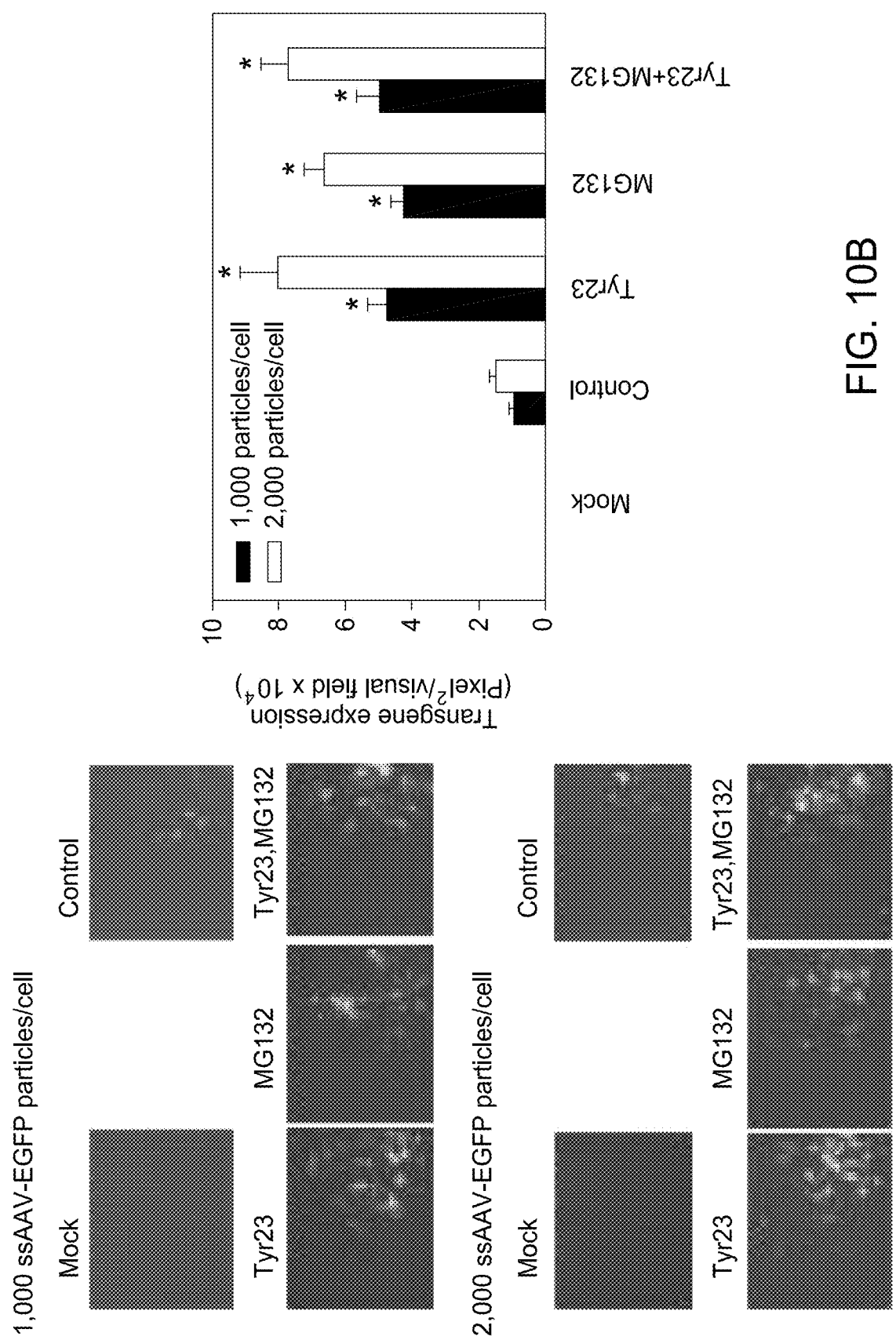
Figure 11:
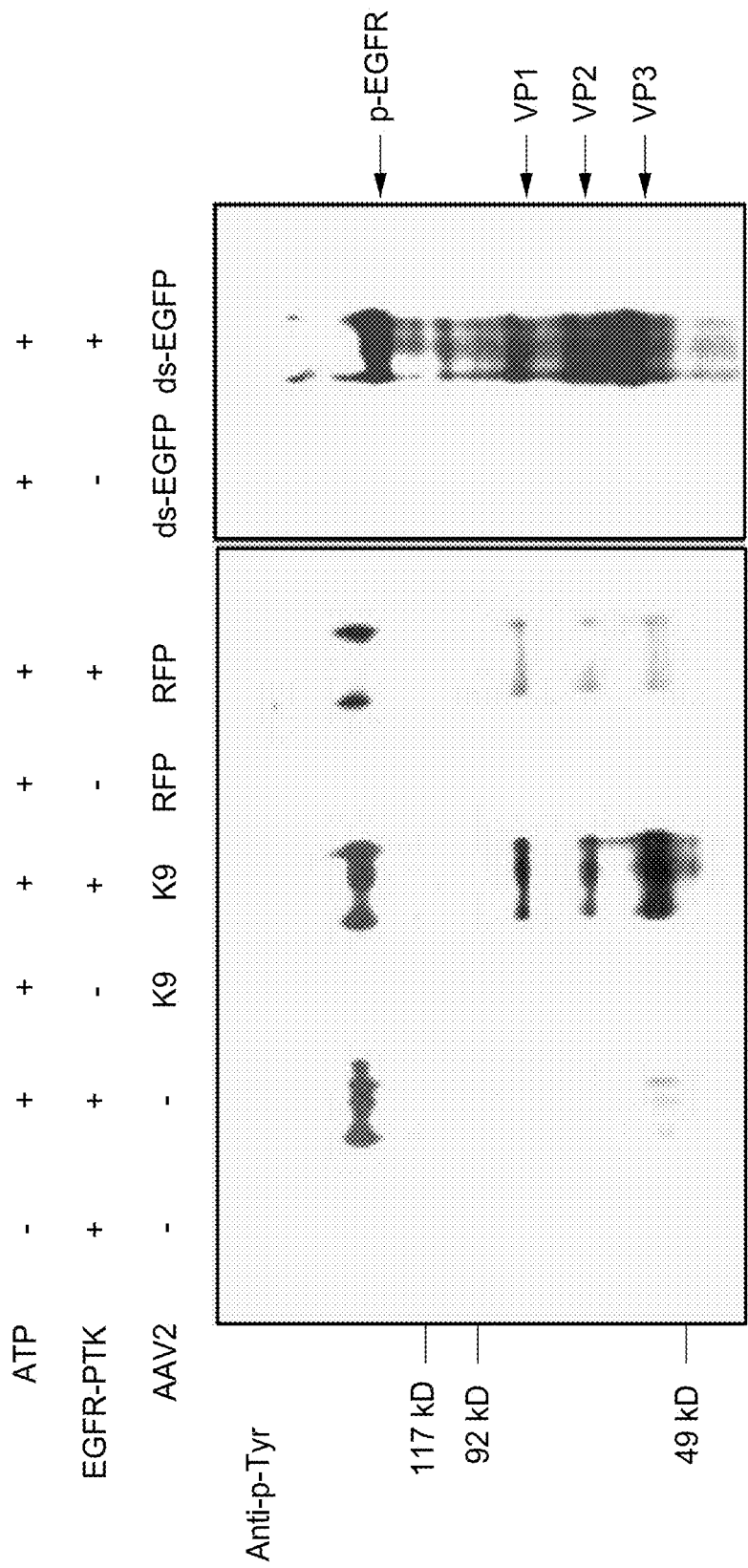
FIG. 11 shows the in vitro phosphorylation of AAV2 capsids by EGFR-PTK from two different packaging systems was analyzed by Western Blotting using anti-p-Tyr antibody for detection of phosphotyrosine containing capsid proteins. K9: AAV2-adiponectin (baculovirus-based heterologous rAAV packaging system); RFP: ssAAV2-RFP (293 cells-based rAAV packaging system); ds-EGFP: scAAV2-CB-EGFP (293 cells-based rAAV packaging system).
Figure 12:
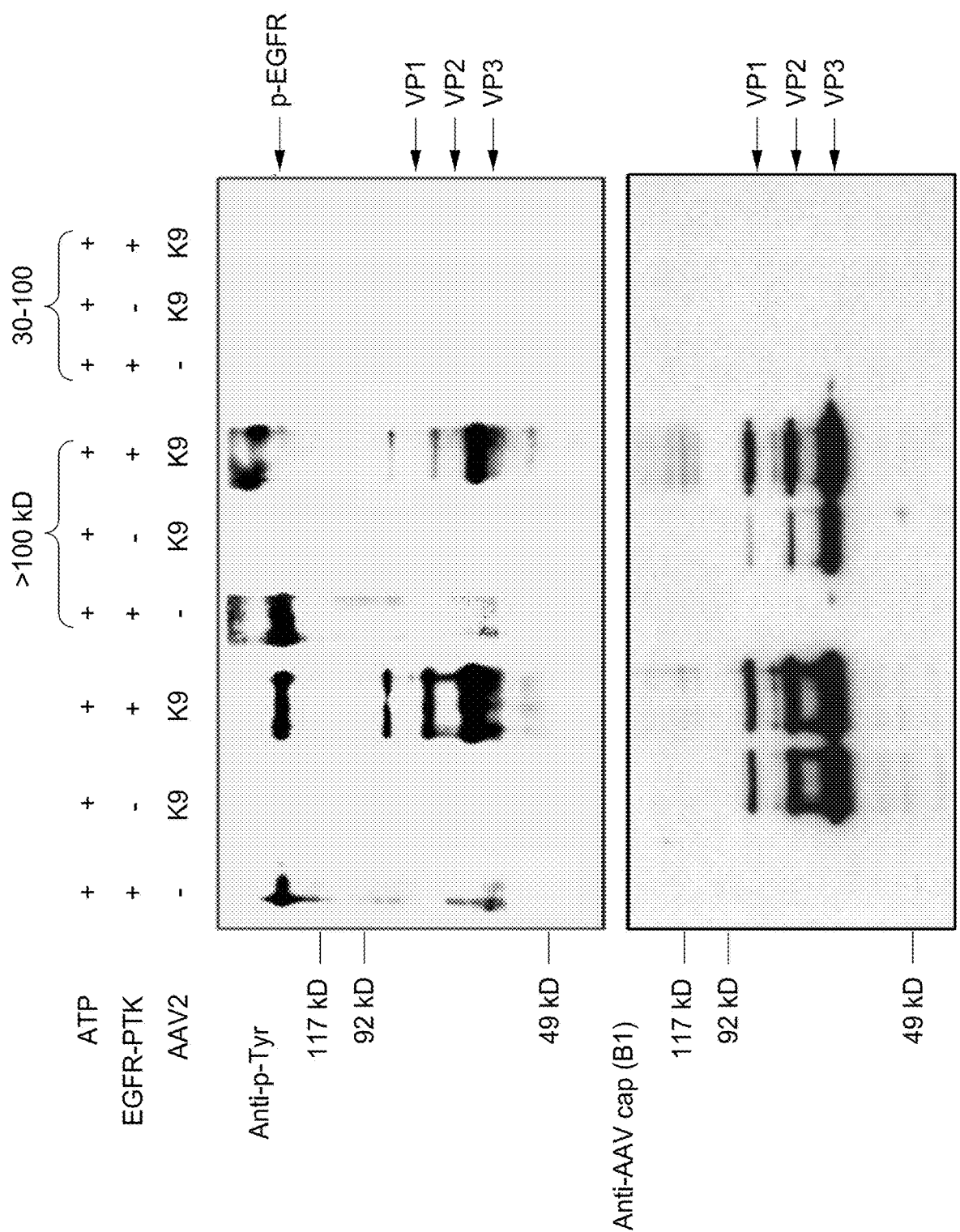
FIG. 12 shows the in vitro phosphorylation of AAV2 capsids by EGFR-PTK followed by separating intact virions and free capsid proteins using centrifugal filter devices [(Ultracel™ YM-100 (kDa) and YM-30 (kDa)] was analyzed by Western blotting using anti-p-Tyr antibody for detection of phosphotyrosine containing capsid proteins and anti-AAV cap (B1) antibody for detection of total capsid proteins. K9: AAV2-adiponectin (baculovirus-based heterologous rAAV packaging system).
Figure 14A:
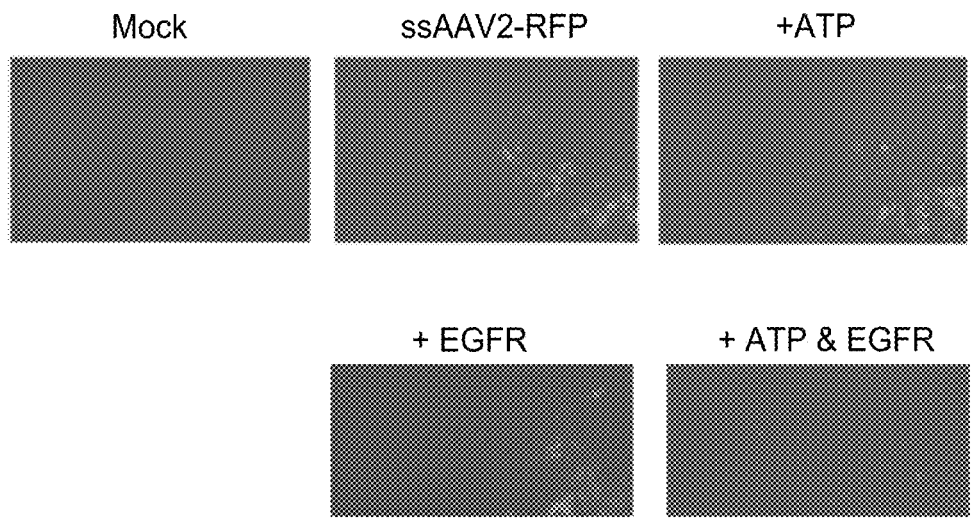
FIG. 14A and FIG. 14B detail the comparative analyses of ssAAV2-mediated transduction efficiency in HeLa cells after in vitro phosphorylation of AAV capsids by EGFR-PTK.
Figure 14B:
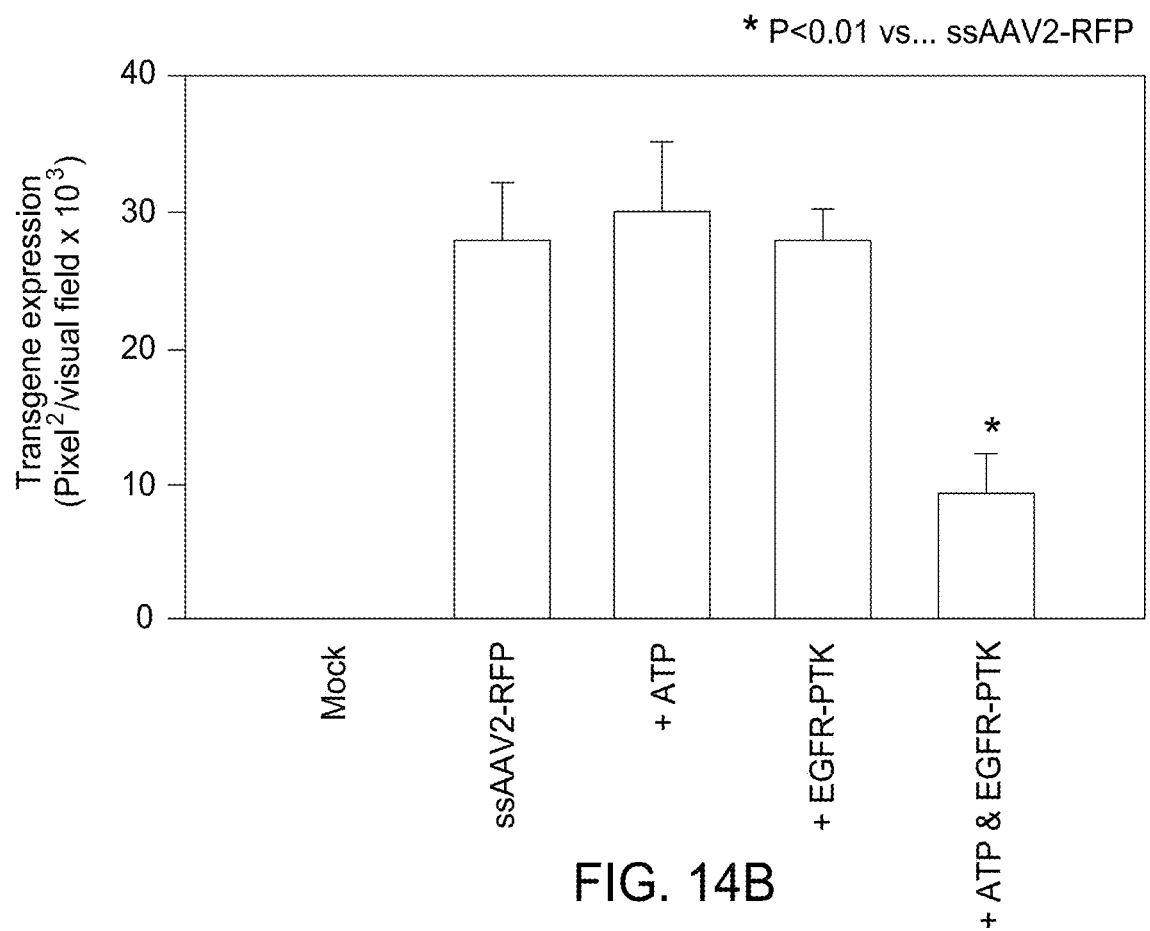
Figure 15A:
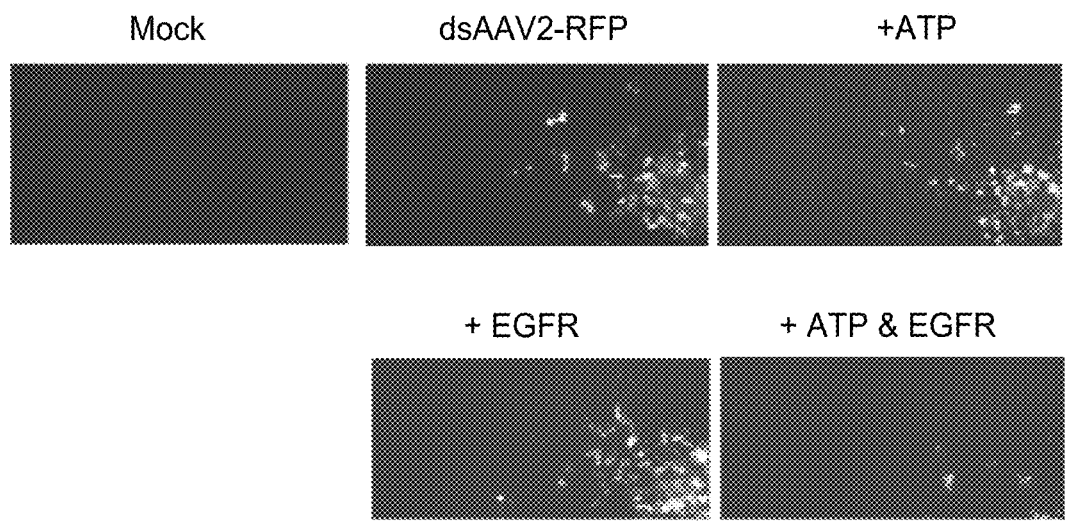
FIG. 15A and FIG. 15B illustrate the comparative analyses of scAAV2-mediated transduction efficiency in HeLa cells after in vitro phosphorylation of AAV2 capsids by EGFR-PTK.
Figure 15B:
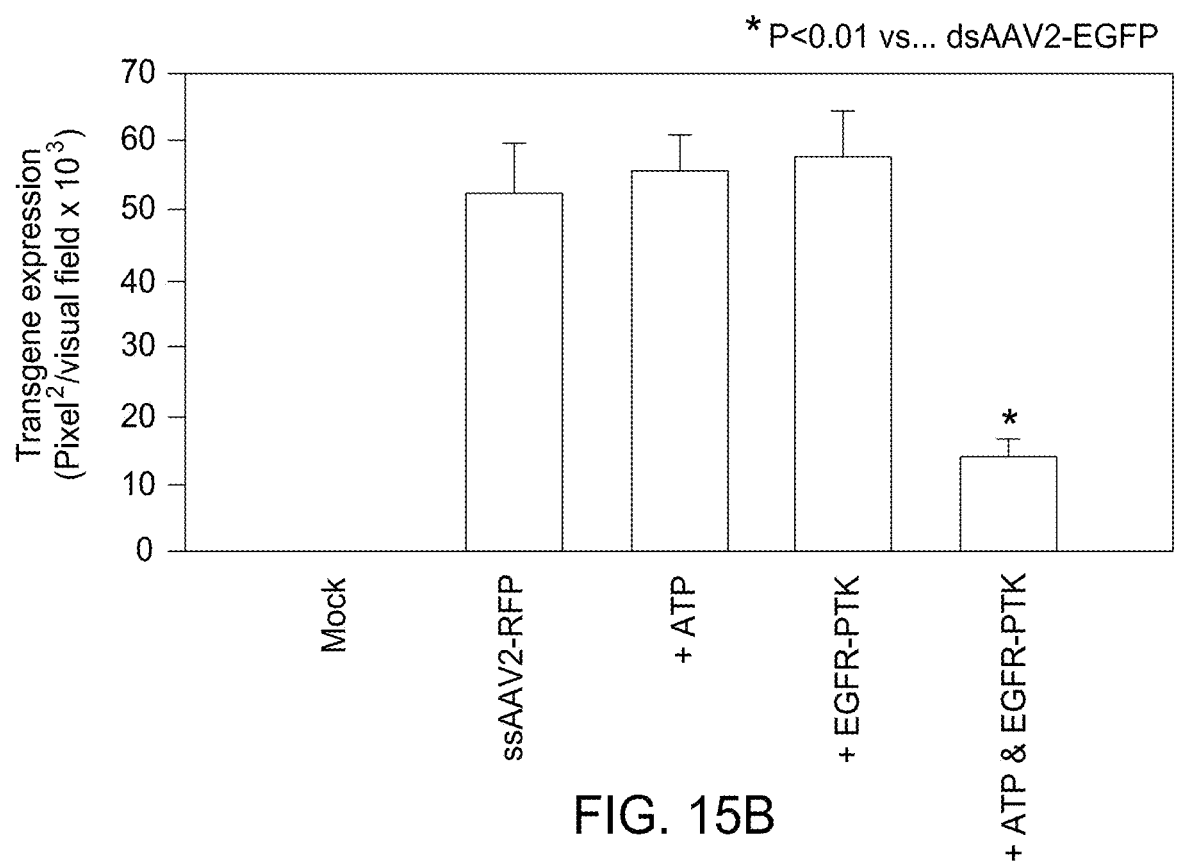
Figure 16B:
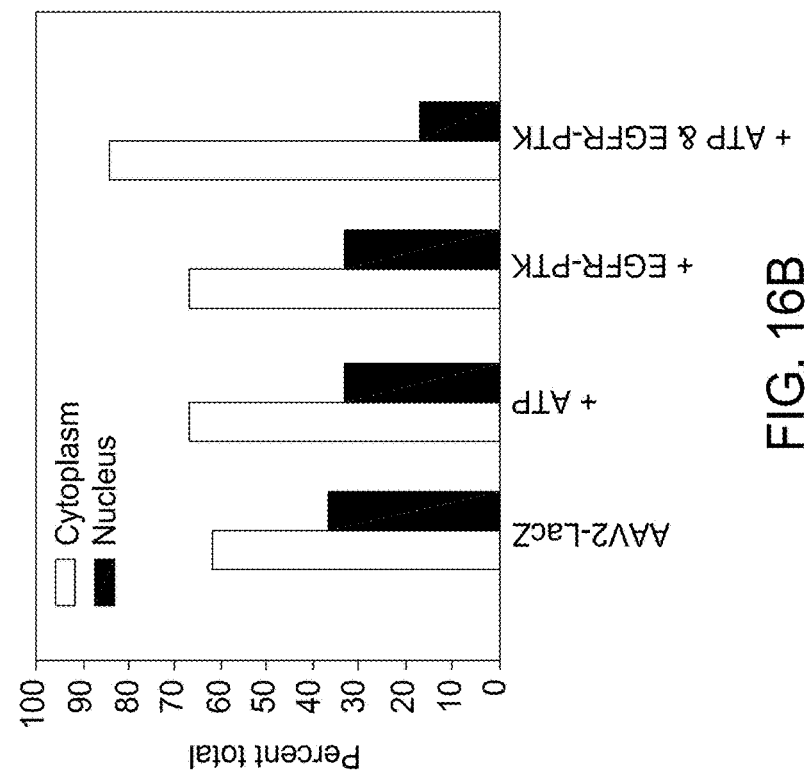
FIG. 16A and FIG. 16B depict Southern hybridization analyses of cytoplasmic and nuclear distribution of AAV2 genomes in HeLa cells after in vitro phosphorylation of AAV2 capsids by EGFR-PTK. HeLa cells were infected by AAV2-LacZ vectors, which were pre-incubated with ATP, EGFR-TPK or both. Low-$M_r$ DNA samples were isolated at 18 hr post-infection and electrophoresed on 1% agarose gels followed analyzed by Southern blot hybridization using a $^{32}$P-labeled LacZ DNA probe (FIG. 16A), and densitometric scanning of autoradiographs for the quantitation of relative amounts of viral genomes (FIG. 16B).
Figure 16A:
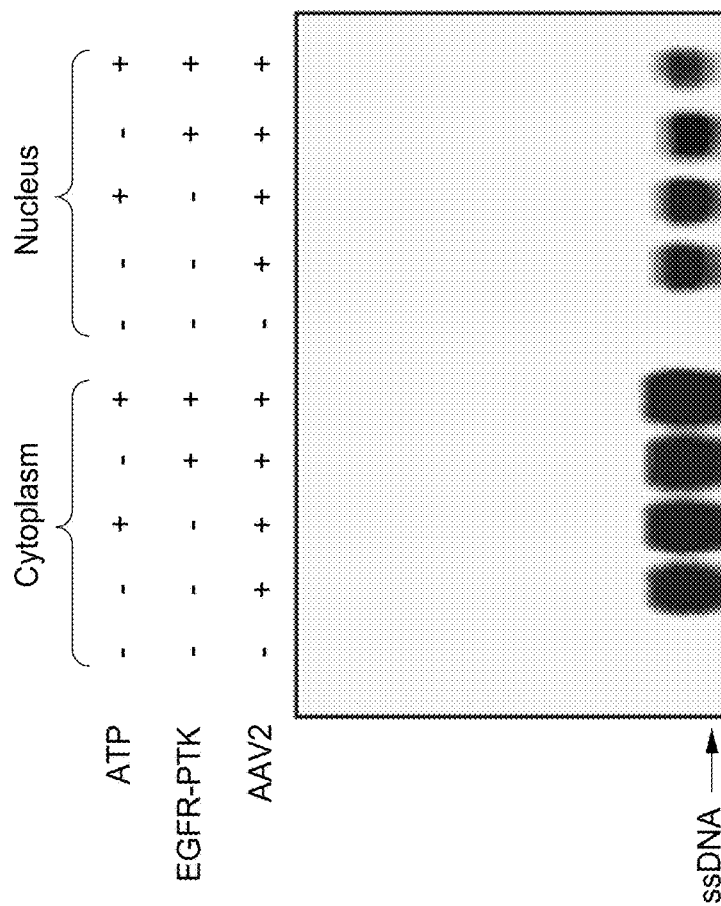

As is evident, ~64% of the input ssAAV DNA was present in the cytoplasmic fraction in control cells (lane 1). Consistent with previously published studies[16, 34, 35], pre-treatment with MG132 improved AAV2 trafficking to the nucleus up to ~62% (lane 10). Interestingly, in cells pre-treated with Tyr23, or stably transfected with the wtTC-PTP, the input ssAAV2 DNA in the nuclear fraction was increased to ~52% and ~54%, respectively (lanes 4 and 8). In cells transfected with the mTC-PTP, on the other hand, only ~38% of the input ssAAV DNA was present in the nuclear fraction (lane 6), which was similar to that in control cells (lane 2). The possibility that Tyr23 and TC-PTP affect transcriptional and translational events to increase transgene expression, as they do not improve nuclear delivery of AAV as well as MG132, was ruled out by plasmid DNA-mediated transfection of HeLa cells in which neither treatment with Tyr23, nor over-expression of TC-PTP, showed any increase in transgene expression (FIG. 9). These results further document that inhibition of EGFR-PTK signaling facilitates nuclear transport of AAV vectors.

Transduction Efficiency of Both ssAAV and rAAV Vectors in Cells Over-Expressing TC-PTP, or Following Pre-Treatment with Tyr23, is not Further Enhanced by MG132.

Figure 4A:
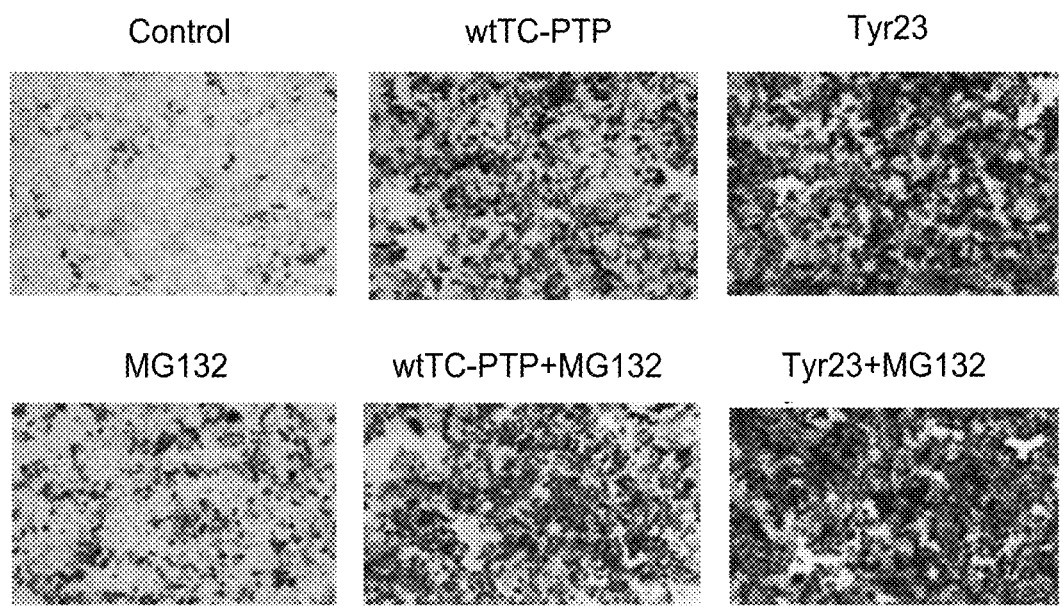
FIG. 4A and FIG. 4B show the comparative analyses of AAV2 transduction efficiency in HeLa cells with various treatments.

It was then examined whether inhibition of EGFR-PTK signaling by treatment with Tyr23, or over-expression of TC-PTP, modulates the ubiquitin/proteasome pathway involved in AAV2 transduction, because the free ubiquitin content within a cell that regulates lysosomal degradation of EGFR, and proteasome inhibitors have been implicated in the regulation of EGFR Endocytosis,[33] proteasome inhibitors have been shown to augment AAV transduction,[16, 31, 32, 34, 35] and protein phosphorylation has been implicated in the regulation of ubiquitination of cellular and viral proteins.[36-42] Cells were mock-treated or treated with Tyr23, MG132 or both, or either stably transfected with wt- or mTC-PTP expression plasmids were either mock-treated or treated with MG132. All treated cells and appropriate controls were infected with recombinant ssAAV2-lacZ or scAAV2-EGFP vectors, and transgene expression was determined 48 hrs post-transduction. These results are shown in FIG. 4A.

Figure 4B:
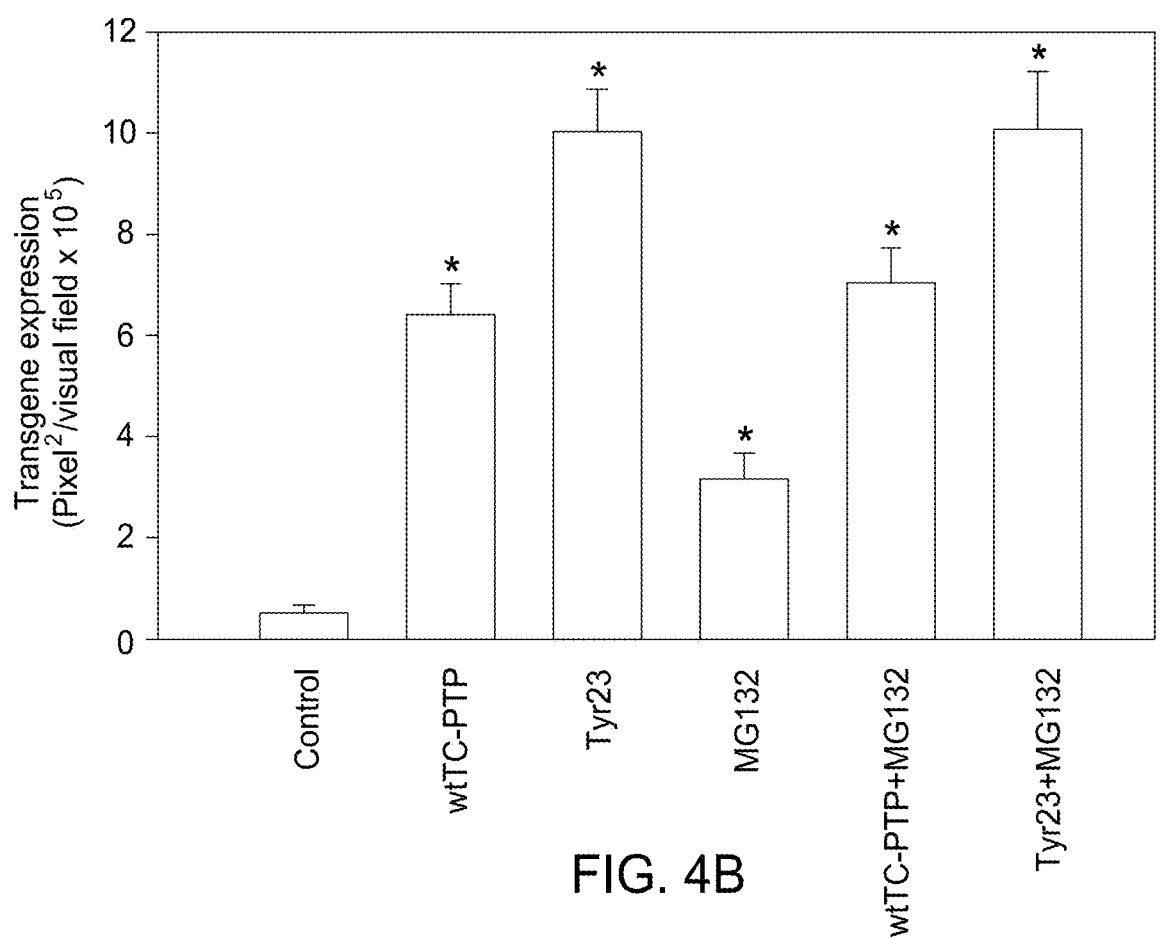
Figure 5A:
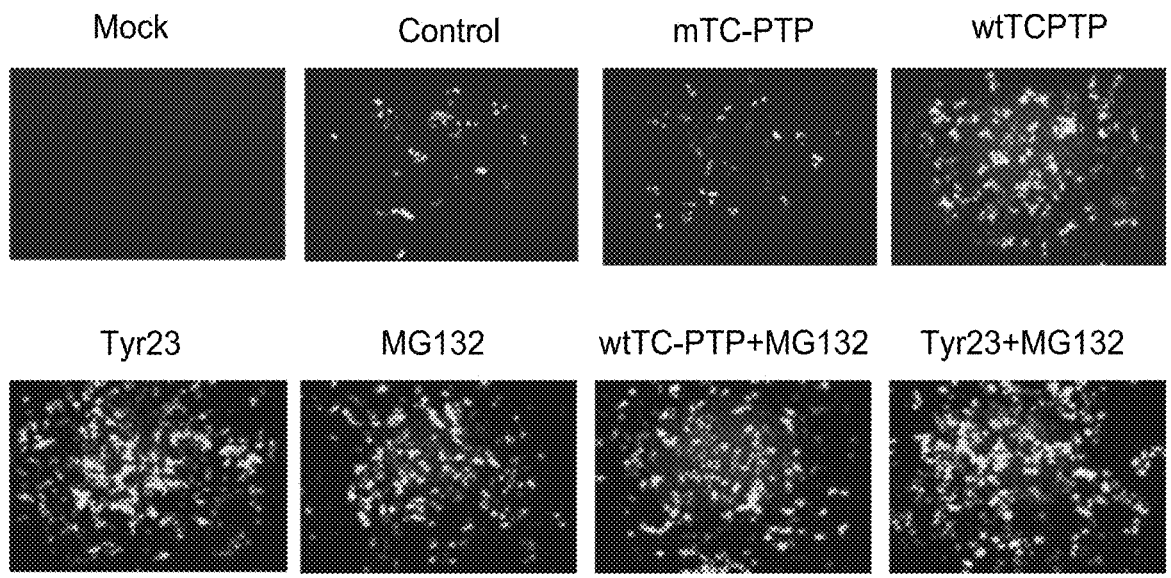
FIG. 5A and FIG. 5B show the comparative analyses of AAV2-mediated transduction efficiency in HeLa cells with various treatments, following transduction with scAAV2-EGFP vectors.
Figure 5B:
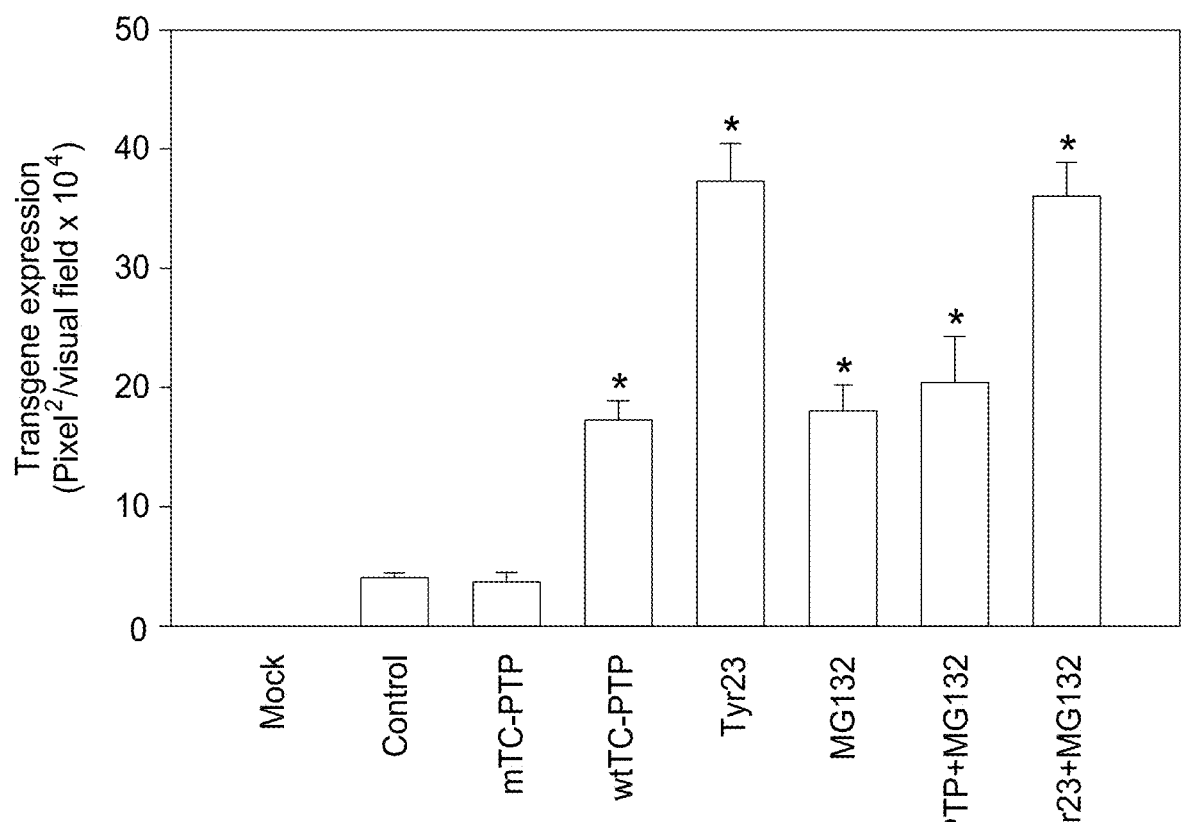

Consistent with previously published studies,[23-25, 27, 43] >5% of cells transduced with ssAAV2 vectors were lacZ-positive, whereas in cells over-expressing wtTC-PTP, or following pre-treatment with Tyr23, there was ~13-fold and ~20-fold increase, respectively, in transduction efficiency of ssAAV vectors (FIG. 4B). Treatment with MG132 for 4 hr (2 hr for pretreatment and 2 hr for treatment together with AAV2 infection) led to ~6-fold increase in transduction efficiency of ssAAV2 vectors (FIG. 4B). Surprisingly, however, the transduction efficiency of ssAAV2 vectors following pretreatment with Tyr23, or TC-PTP over-expression, was not further enhanced by MG132. Similar results were obtained when rAAV-EGFP vectors were used under identical conditions. As can be seen in FIG. 5A, whereas mock-infected cells showed no green fluorescence, and ~15% of mock-treated cells transduced with scAAV2 vectors were EGFP-positive, over-expression of TC-PTP, or pre-treatment with Tyr23 led to ~5-fold and ~9-fold increase, respectively, in transduction efficiency of scAAV2 vectors (FIG. 5B). Treatment with MG132 led to ~5-fold increase in scAAV2 transduction efficiency (FIG. 5B). This increase was not observed when the mTC-PTP expression plasmid was used.

It is noteworthy that the transduction efficiency of scAAV2 vectors following pre-treatment with Tyr23, or over-expression of TC-PTP, was not further enhanced by MG132 (FIG. 5B). Similar results were obtained when lower viral particles/cell (1,000 and 2,000) ratios were used (FIG. 9). These data further suggest that inhibition of EGFR-PTK signaling modulates the ubiquitin/proteasome pathway, which affects aspects of intracellular trafficking as well as second-strand DNA synthesis of AAV2 vectors.

Inhibition of EGFR-PTK Signaling Decreases Ubiquitination of AAV2 Capsid Proteins as Well as Total Cellular Proteins.

Figure 6:
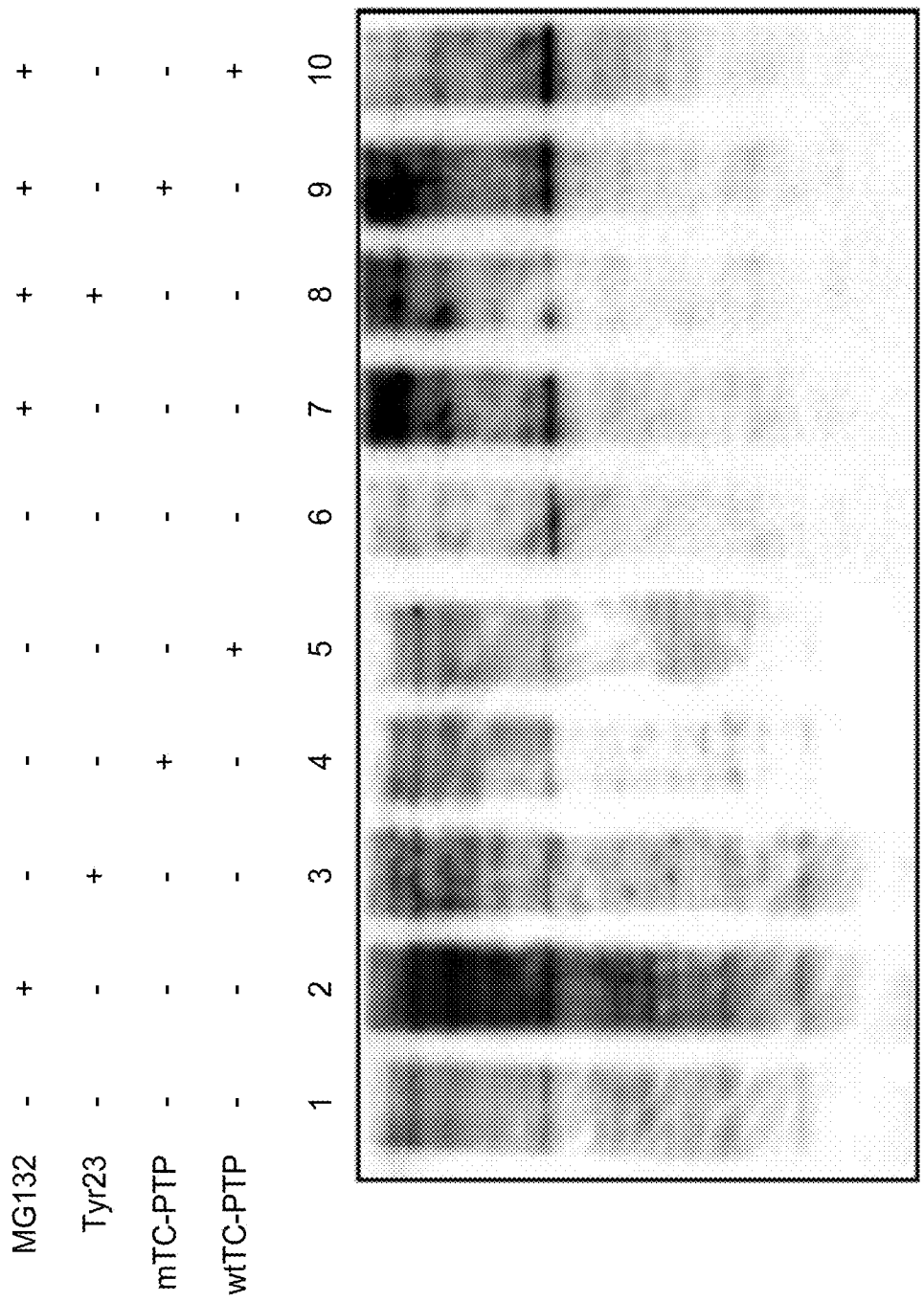
FIG. 6 shows the western blot analyses of ubiquitinated proteins in HeLa cells following treatment with MG132 in the presence or absence of Tyr23 or TC-PTP. Whole cell lysates (WCL) prepared from untreated cells (lanes 1 and 6), and following treatment with MG132 (lanes 2 and 7), Tyr23 (lane 3), or both (lane 8), and cells either stably transfected with the wt- or mTC-PTP expression plasmids following either mock-treatment (lanes 4 and 5) or treatment with MG132 (lanes 9 and 10) were probed with anti-Ub monoclonal antibody.

The ubiquitin-proteasome pathway plays an important role in the cell by specifically degrading both endogenous and foreign proteins.[47] A previous study[48] reported that immunoprecipitated AAV2 capsid proteins from infected cell lysates are conjugated with ubiquitin (Ub) and heat-denatured virus particles are substrates for in vitro ubiquitination. A more recently study[42] documented that casein kinase II-induced phosphorylation of serine residue 301 promotes ubiquitination and degradation of the bovine papillomavirus E2 protein by the proteasome pathway. To further examine whether EGFR-signaling is involved in ubiquitination of AAV2 capsid proteins, the following two sets of studies were performed: In the first study, cells were either mock-treated or treated with MG132, Tyr23, or both, and cells either stably transfected with the wt- or mTC-PTP expression plasmids were either mock-treated or treated with MG132 as described supra. WCL were prepared and equivalent amounts of proteins were subjected to Western blot analyses with anti-Ub monoclonal antibody. These results are shown in FIG. 6. Whereas the total level of smeary ubiquitinated cellular proteins was low in untreated cells (lanes 1 and 6), and remained unchanged in Tyr23-teated cells (lane 3) as well as in cells either stably transfected with wt- or mTC-PTP expression plasmids (lanes 4 and 5), because these molecules are quickly degraded by the proteasome following ubiquitination, the significant accumulation of smeary ubiquitinated proteins in HeLa cells following inhibition of proteasome activity by treatment with MG132 was observed as expected (lanes 2 and 7). Interestingly, however, Tyr23 treatment, or over-expression of wtTC-PTP, significantly decreased the accumulation of MG132-induced ubiquitinated proteins (lanes 8 and 10), whereas over-expression of mTC-PTP had no effect (lane 9). In the second set, all mock-treated and treated cells were infected with AAV2 for 2 hrs at 37° C. WCL were prepared at 4 hrs post-infection and equivalent amounts of proteins were immunoprecipitated first with anti-AAV2 capsid antibody A20 followed by Western blot analyses with anti-Ub monoclonal antibody.

Figure 7:
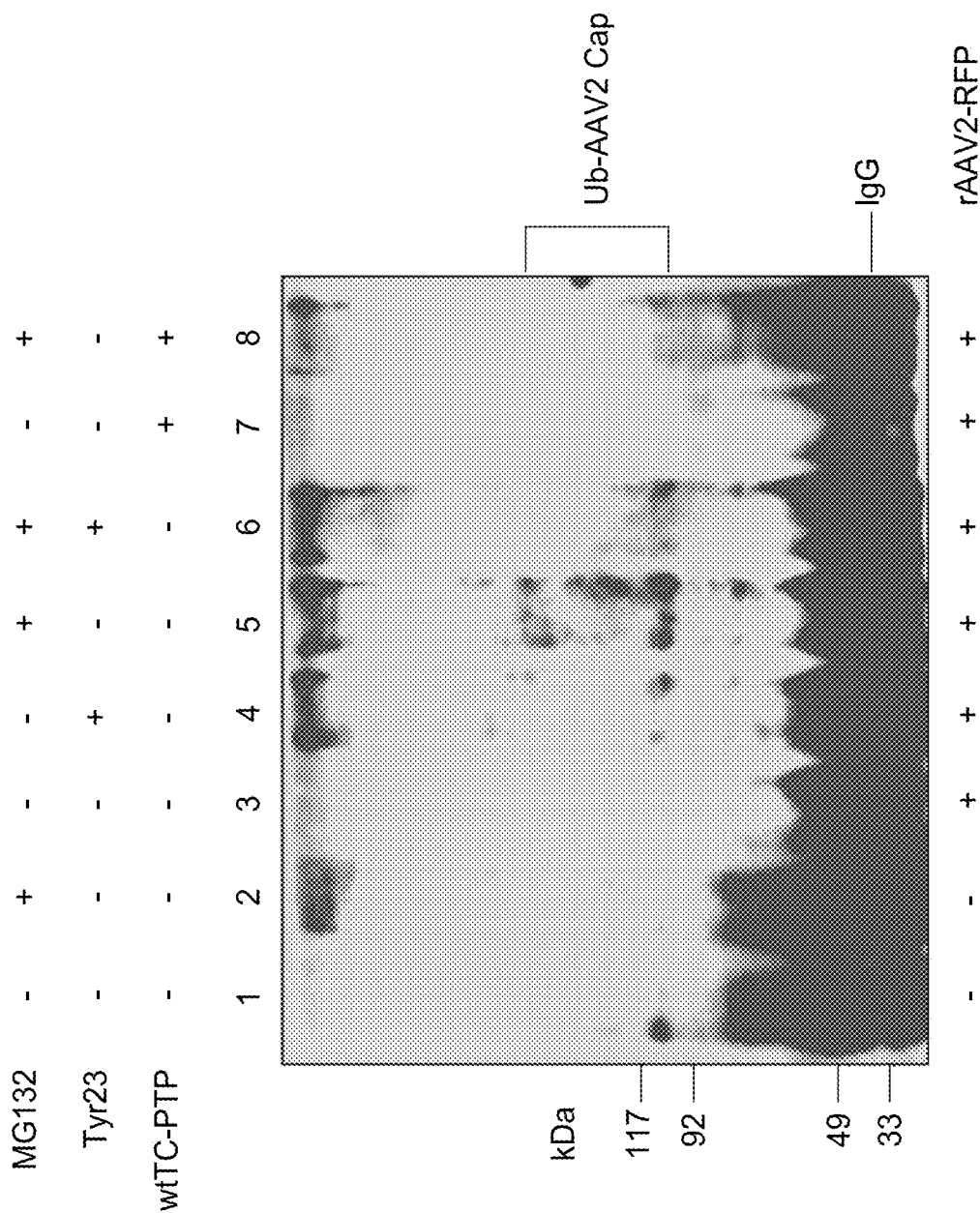
FIG. 7 shows the western blot analyses of ubiquitinated AAV2 capsid proteins in HeLa cells treated with MG132 in the presence or absence of Tyr23 or wtTC-PTP, following transduction with ssAAV2-RFP vectors. WCL prepared from HeLa cells untreated or treated with MG132 following mock-infected (lane 1 and 2), and HeLa cells untreated (lane 3), treated with Tyr23 (lane 4), MG132 (lane 5), or both (lane 6), or cells stably transfected with the wtTC-PTP expression plasmid following either mock-treatment (lane 7) or treatment with MG132 (lane 8), following infection with ssAAV2-RFP vectors were immunoprecipitated with anti-AAV2 capsid antibody A20 followed by Western blot analyses with anti-Ub monoclonal antibody.

Similar results, shown in FIG. 7, indicate that whereas the ubiquitinated AAV2 capsid proteins (Ub-AAV Cap, bracket) were undetectable in mock-infected cells (lanes 1 and 2), the signal of ubiquitinated AAV2 capsid proteins was weaker in untreated cells (lane 3), and remained unchanged in Tyr23-teated cells (lane 4) as well as in cells stably transfected with wtTC-PTP expression plasmid (lane 7), a significant accumulation of ubiquitinated AAV2 capsid proteins occurred following treatment with MG132 (lane 5). However, treatment with Tyr23, or over-expression of wtTC-PTP dramatically inhibited the extent of accumulation of MG132-induced ubiquitinated AAV2 capsid proteins (lanes 6 and 8). These results substantiate that inhibition of EGFR protein tyrosine kinase signaling also decreases ubiquitination of total cellular proteins as well as AAV2 capsid proteins.

Discussion

In published studies[19] the inventors and their colleagues have documented that intracellular trafficking of AAV2 from cytoplasm to nucleus is improved in murine hematopoietic stem cells from TC-PTP-transgenic mice. These data suggested that in addition to its crucial role in viral second-strand DNA synthesis, EGFR-PTK signaling was also involved in intracellular trafficking and/or nuclear transport of AAV2. The ubiquitin-proteasome pathway plays an essential role in AAV2 intracellular trafficking, and proteasome inhibitors can promote AAV2 nuclear transport, leading to augmentation of AAV2 transduction.[16, 31, 32] Direct evidence for ubiquitination of AAV2 capsid proteins in HeLa cells and in in vitro ubiquitination assays has been presented,[48] where only denatured AAV2 capsids, but not intact AAV2, could be ubiquitinated in vitro, which indicated that the intact AAV2 capsid required a conformational change or a modification, such as phosphorylation before its ubiquitination. A number of studies have reported that phosphorylation of cellular proteins by tyrosine or serine/threonine protein kinase is required for efficient ubiquitination and degradation of these proteins.[36-42] For example, phosphorylation of inhibitory κBα (IκBα) at serine residue #32 (Ser32) and serine residue #36 (Ser36) is a pre-requisite for cytokine-induced IκBα ubiquitination and degradation.[36, 37]

Receptor-mediated tyrosine kinase activation has been shown to be a requirement for T cell antigen receptor ubiquitination,[38] and ubiquitination of CD16 ζ chain in human NK cells following receptor engagement has been shown to be tyrosine kinase-dependent.[39] Modification of bovine papillomavirus E2 transactivator protein by ubiquitination was reduced by mutation of serine residue #301 (Ser301), which indicated that phosphorylation of this residue was required for efficient ubiquitination and degradation of this protein by the ubiquitin-proteasome pathway.[41] Furthermore, casein kinase II-induced phosphorylation of Ser301 in E2 protein induced a conformational change and decreased the local thermodynamic stability of this region, promoting ubiquitination and targeted degradation of the E2 protein by the proteasome pathway.[42]

Figure 8:
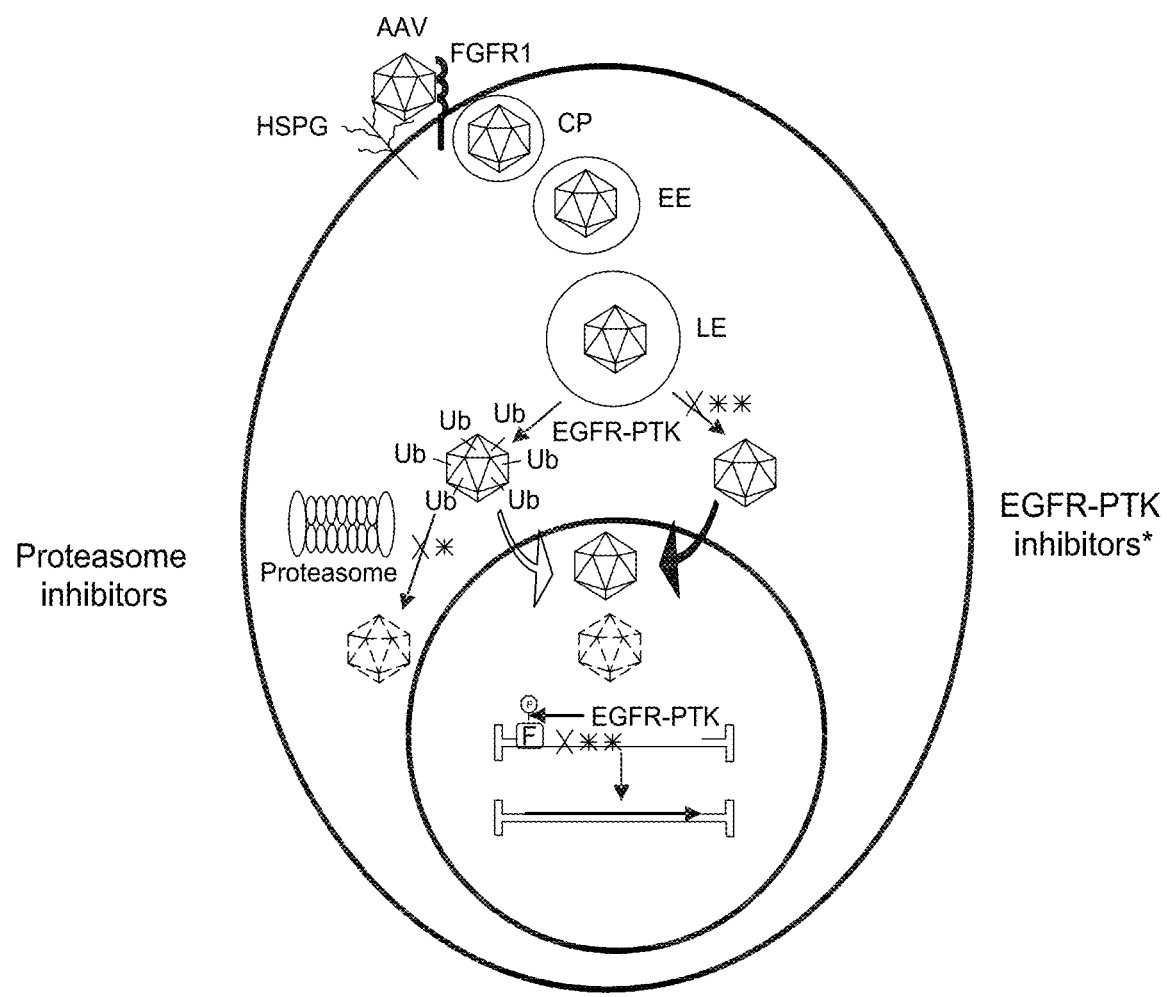
FIG. 8 shows a model for interaction between EGFR-PTK signaling and ubiquitin/proteasome pathway in the regulation of intracellular trafficking as well as second-strand DNA synthesis of AAV2 vectors. Early endosome (EE); clathrin-coated pits (CP); late endosome (LE); FKBP52 (F); phosphotyrosine residues (P).

The present studies have demonstrated that EGFR-PTK signaling is indeed involved in the ubiquitin/proteasome pathway for modulation of nuclear transport of AAV2 vectors in addition to regulating viral second-strand DNA synthesis in HeLa cells. Similar results were also obtained with the murine fibroblast cell line NIH3T3, adult mouse hepatocyte cell line H2.35, and fetal mouse hepatocyte cell line FL83B. Based on the available data, a model (shown schematically in FIG. 8) has been postulated, which helps explain the interactions between EGFR-PTK signaling and ubiquitin/proteasome pathway in modulating intracellular trafficking of AAV2 vectors as well as viral second-strand DNA synthesis. In this model, following infection via binding to its primary cellular receptor, heparan sulfate proteoglycan (HSPG), and entry mediated by a co-receptor(s), such as FGFR1, AAV2 enters into the early endosome (EE) through clathrin-coated pits (CP)-mediated endocytosis. The EE then matures into late endosome (LE), in which AAV is degraded by lysosomal enzymes, if it fails to escape from the LE. If AAV2 escapes into cytoplasm perinuclearly, it is ubiquitinated. It is hypothesized that EGFR-PTK-mediated phosphorylation of capsid proteins at tyrosine residues is a prerequisite for ubiquitination.

A substantial number of ubiquitinated virions are then recognized and degraded by cytoplasmic proteasomes on their way to the nucleus, leading to inefficient nuclear transport (open arrow). In the presence of proteasome inhibitors, vector degradation is reduced, leading to more efficient nuclear transport of AAV. Inhibition of AAV2 capsid phosphorylation at tyrosine residues by EGFR-PTK inhibitors results in decreased ubiquitination of intact virions, which in turn, escape proteasome-mediated degradation, an effect similar to what is seen with proteasome inhibitors. The net result is that intact virions enter the nucleus more efficiently (closed arrow). Following uncoating in the nucleus, the D-sequence in the AAV2 ITR forms a complex with FKBP52 [F], which is phosphorylated at tyrosine residues [P] by EGFR-PTK, and inhibits viral second-strand DNA synthesis. EGFR-PTK inhibitors prevent phosphorylation of FKBP52 at tyrosine residues, and dephosphorylated FKBP52 no longer binds to the AAV2 D-sequence, which in turn, facilitates viral second-strand DNA synthesis and efficient transgene expression ensues.

Consistent with this model, it was observed that AAV2 capsids can indeed be phosphorylated at tyrosine residues by EGFR-PTK in in vitro phosphorylation assays, and that phosphorylated AAV2 virions transduce cells much less efficiently.

Example 2—AAV2-Mediated Gene Transfer: Tyrosine Phosphorylation of Capsid Proteins and its Consequences on Transgene Expression The transduction efficiency of recombinant adeno-associated virus 2 (AAV) vectors varies greatly in different cells and tissues in vitro and in vivo. Data from exemplary studies are illustrated in FIG. 11, FIG. 12, FIG. 13, FIG. 14, and FIG. 15. Systematic studies were performed to elucidate the fundamental steps in the life cycle of AAV. For example, the inventors have shown that a cellular protein, FKBP52, phosphorylated at tyrosine residues by epidermal growth factor receptor protein tyrosine kinase (EGFR-PTK), inhibits AAV second-strand DNA synthesis and consequently, transgene expression in vitro[24, 25] as well as in vivo.[19, 27, 28]

The inventors have also demonstrated that EGFR-PTK signaling modulates the ubiquitin/proteasome pathway-mediated intracellular trafficking as well as FKBP52-mediated second-strand DNA synthesis of AAV vectors. In those studies, inhibition of EGFR-PTK signaling led to decreased ubiquitination of AAV capsid proteins, which in turn, facilitated nuclear transport by limiting proteasome-mediated degradation of AAV vectors, implicating EGFR-PTK-mediated phosphorylation of tyrosine residues on AAV capsids.

The present example shows that AAV capsids can indeed be phosphorylated at tyrosine residues by EGFR-PTK in in vitro phosphorylation assays, and that phosphorylated AAV capsids retained their structural integrity. However, although phosphorylated AAV vectors could enter cells as efficiently as their unphosphorylated counterparts, their transduction efficiency was reduced. This reduction was not due to impaired viral second-strand DNA synthesis since transduction efficiency of both single-stranded AAV (ssAAV) and self-complementary AAV (rAAV) vectors was decreased by ~68% and ~74%, respectively. Intracellular trafficking of tyrosine-phosphorylated AAV vectors from cytoplasm to nucleus was also significantly decreased, which most likely led to ubiquitination of AAV capsids followed by proteasome-mediated degradation.

AAV capsids can be phosphorylated at tyrosine residues by EGFR-PTK in in vitro phosphorylation assay and that phosphorylated AAV capsids retained their structural integrity. Although phosphorylated AAV vectors could enter cells as efficiently as their unphosphorylated counterparts, their transduction efficiency was significantly reduced. This reduction was not due to impaired viral second-strand DNA synthesis since transduction efficiency of both single-stranded AAV (ssAAV) and self-complementary AAV (rAAV) vectors was decreased by ~68% and ~74%, respectively. Intracellular trafficking of tyrosine-phosphorylated AAV vectors from cytoplasm to nucleus was also significantly decreased, most likely led to ubiquitination of AAV capsids followed by proteasome-mediated degradation. Taken together, these data illustrate that the complex interactions occurring between EGFR-PTK signaling and ubiquitin/proteasome pathway affects various aspects of intracellular trafficking as well as second-strand DNA synthesis of AAV vectors.

Example 3—Next Generation RAAV2 Vectors: Point Mutations in Tyrosines Lead to High-Efficiency Transduction at Lower Doses The present example demonstrates that mutations of surface-exposed tyrosine residues on AAV2 capsids circumvents the ubiquitination step, thereby avoiding proteasome-mediated degradation, and resulting in high-efficiency transduction by these vectors in human cells in vitro and murine hepatocytes in vivo, leading to the production of therapeutic levels of human coagulation factor at reduced vector doses. The increased transduction efficiency observed for tyrosine-mutant vectors is due to lack of ubiquitination, and improved intracellular trafficking to the nucleus. In addition to yielding insights into the role of tyrosine phosphorylation of AAV2 capsid in various steps in the life cycle of AAV2, these studies have resulted in the development of novel AAV2 vectors that are capable of high-efficiency transduction at lower doses.

Materials and Methods

Recombinant AAV2 vectors. Highly purified stocks of or scAAV2 vectors containing the enhanced green fluorescence protein (EGFP) gene driven by the chicken β-actin (CBA) promoter (scAAV2-EGFP), and ssAAV2 vectors containing the factor IX (F.IX) gene under the control of the apolipoprotein enhancer/human α-1 antitrypsin (ApoE/hAAT) promoter (ssAAV2-F.IX) were generated as described previously.

Localization of Surface-Tyrosines on the AAV2 Capsid Surface.

The crystal structure of AAV2 (PDB accession number 1lp3) was used to localize the tyrosine residues on the AAV2 capsid surface. The icosahedral two-, three- and five-fold related VP3 monomers were generated by applying icosahedral symmetry operators to a reference monomer using Program 0 on a Silicon graphics Octane workstation. The position of the tyrosine residues were then visualized and analyzed in the context of a viral asymmetric unit using the program COOT, and graphically presented using the program PyMOL Molecular Graphics System (DeLano Scientific, San Carlos, Calif., USA).

Construction of Surface-Exposed Tyrosine Residue Mutant AAV2 Capsid Plasmid.

A two-stage procedure, based on QuikChange II® site-directed mutagenesis (Stratagene, La Jolla, Calif.) was performed using plasmid pACG-2. Briefly, in stage one, two PCR extension reactions were performed in separate tubes for each mutant. One tube contained the forward PCR primer and the other contained the reverse primer (Table 2). In stage two, the two reactions were mixed and a standard PCR mutagenesis assay was carried out as per the manufacturer's instructions. PCR primers were designed to introduce changes from tyrosine to phenylalanine residues as well as a silent change to create a new restriction endonuclease site for screening purposes (Table 2). All mutants were screened with the appropriate restriction enzyme and were sequenced prior to use.

Preparation of Whole Cell Lysates (WCL) and Co-Immunoprecipitations.

WCL were prepared as described. Approximately $2 \times 10^6$ HeLa cells, mock-treated or treated with MG132, were also subjected to mock-infection or infection with the WT scAAV2-EGFP or Y730F mutant vectors at $5 \times 10^3$ particles/cell for 2 hr at 37° C. For immunoprecipitations, cells were treated with 0.01% trypsin and washed extensively with PBS. WCL were cleared of non-specific binding by incubation with 0.25 mg of normal mouse IgG together with 20 μl of protein G-agarose beads. After preclearing, 2 μg of capsid antibody against intact AAV2 particles (mouse monoclonal IgG$_3$, clone A20; Research Diagnostics, Inc. (Flanders, N.J.), or 2 μg of normal mouse IgG (as a negative control) were added and incubated at 4° C. for 1 hr, followed by precipitation with protein G-agarose beads. For immunoprecipitations, resuspended pellet solutions were used for SDS-PAGE. Membranes were treated with monoclonal HRP-conjugated anti-Ub antibody (1:2,000 dilution) specific for ubiquitin (Ub) (mouse monoclonal immunoglobulin G$_1$ [IgG$_1$], clone P4D1; Santa Cruz, Calif.) Immunoreactive bands were visualized using chemiluminescence (ECL-plus, Amersham Pharmacia Biotech, Piscataway, N.J.).

Isolation of Nuclear and Cytoplasmic Fractions from HeLa Cells.

Nuclear and cytoplasmic fractions from HeLa cells were isolated and mock-infected or recombinant wt scAAV2-EGFP or Y700F vector-infected cells were used to isolate the cytoplasmic and nuclear fractions. The purity of each fraction was determined to be >95%.

Southern Blot Analysis for AAV2 Trafficking.

Low-M$_r$ DNA samples from nuclear and cytoplasmic fractions were isolated and electrophoresed on 1% agarose gels or 1% alkaline-agarose gels followed by Southern blot hybridization using a $^{32}$P-labeled EGFP-specific DNA probe.

Recombinant AAV2 Vector Transduction Assays In Vitro.

Approximately $1 \times 10^5$ HeLa cells were used for transductions with recombinant AAV2 vectors. The transduction efficiency was measured 48 hr post-transduction by EGFP imaging using fluorescence microscopy. Images from three to five visual fields were analyzed quantitatively by ImageJ analysis software (NIH, Bethesda, Md., USA). Transgene expression was assessed as total area of green fluorescence (pixel$^2$) per visual field (mean±SD). Analysis of variance (ANOVA) was used to compare between test results and the control and they were determined to be statistically significant.

TABLE 2

NUCLEOTIDE SEQUENCES OF PRIMERS USED FOR SITE-DIRECTED MUTAGENESIS

| Mutant | SEQ ID NO: | Primer Sequences (5' to 3') |
|---|---|---|
| Y252F | SEQ ID NO: 1 | CCCTGCCCACCTTCAACAACCACCTGTACAAACAAATTTCCAGCC<br>              Tyr-Phe   BsrGI |
| Y272F | SEQ ID NO: 2 | CCAATCAGGAGCTTCGAACGACAATCACTTCTTTGGCTACAG<br>            BstBI          Tyr-Phe |
| Y444F | SEQ ID NO: 3 | CGACCAGTACCTGTATTTCTTAAGCAGAACAAACACTCCAAG<br>               Tyr-Phe     Afl11 |
| Y500F | SEQ ID NO: 4 | CAACAACAGTGAATTCTCGTGGACCGGTGCTACCAAGTACC<br>              Tyr-Phe     AgeI |
| Y700F | SEQ ID NO: 5 | GGAATCCCGAAATTCAGTTCACTTCGAACTACAACAAGTCTG<br>              Tyr-Phe     BstBI |
| Y704F | SEQ ID NO: 6 | GGAATCCCGAAATTCAGTACACTTCGAACTTCAACAAGTCTG<br>             BstBI         Tyr-Phe |
| Y730F | SEQ ID NO: 7 | CCTCGCCCCATTGGTACCAGATTCCTGACTCGTAATC<br>             Acc65I       Tyr-Phe |

Recombinant AAV2 Vector Transduction Studies In Vivo.

scAAV2-EGFP vectors were injected intravenously via the tail vein into C57BL/6 mice at $1\times10^{10}$ virus particles per animal. Liver sections from three hepatic lobes of the mock-injected and injected mice 2 weeks after injection were mounted on slides. The transduction efficiency was measured by EGFP imaging as described. ssAAV2-F.IX vectors were injected intravenously (via the tail vein) or into the portal vein of C57BL/6, BALB/c, and C3H/HeJ mice at $1\times10^{10}$ or $1\times10^{11}$ virus particles per animal. Plasma samples were obtained by retro-orbital bleed and analyzed for hF.IX expression by ELISA.

Results

Mutations in Surface-Exposed Tyrosine Residues Significantly Improve the Transduction Efficiency of AAV2 Vectors in HeLa Cells In Vitro.

To demonstrate that tyrosine-phosphorylation of AAV2 capsids leads to increased ubiquitination and results in impaired intracellular trafficking, and is therefore unfavorable to viral transduction, surface-exposed tyrosine residues were modified on AAV2 capsids. Inspection of the capsid surface of the AAV2 structure revealed a total of 7 surface-exposed tyrosine residues (Y252, Y272, Y444, Y500, Y700, Y704, and Y730). Site-directed mutagenesis was performed for each of the 7 tyrosine residues, which were conservatively substituted with phenylalanine residues (tyrosine-phenylalanine, Y-F) (Table 2). scAAV2-EGFP genomes encapsidated in each of the tyrosine-mutant capsids were successfully packaged (Table 3), and mutations of the surface-exposed tyrosine residues did not lead to reduced vector stability.

TABLE 3

TITERS OF WILDTYPE (WT) AND TYROSINE-MODIFIED (Y-F MUTANTS) AAV2 VECTORS

| AAV Vectors | $1^{st}$ packaging titers (vgs/ml) | $2^{nd}$ packaging titers (vgs/ml) | $3^{rd}$ packaging titers (vgs/ml) | $4^{th}$ packaging titers (vgs/ml) |
|---|---|---|---|---|
| WT scAAV2-EGFP | $3.4 \times 10^{11}$ | $1.0 \times 10^{12}$ | $3.2 \times 10^{11}$ | $3.0 \times 10^{11}$ |
| Y252F scAAV2-EGFP | $3.8 \times 10^{11}$ | $4.0 \times 10^{11}$ | ND | ND |
| Y272 scAAV2-EGFP | $7.7 \times 10^{11}$ | $1.0 \times 10^{11}$ | ND | ND |
| Y444F scAAV2-EGFP | $9.7 \times 10^{10}$ | $4.0 \times 10^{10}$ | $6.0 \times 10^{9}$ | $5.0 \times 10^{10}$ |
| Y500F scAAV2-EGFP | $8.8 \times 10^{10}$ | $2.0 \times 10^{9}$ | $4.0 \times 10^{10}$ | $6.0 \times 10^{10}$ |
| Y700F scAAV2-EGFP | $1.0 \times 10^{11}$ | $4.0 \times 10^{11}$ | ND | ND |
| Y704F scAAV2-EGFP | $6.0 \times 10^{11}$ | $2.0 \times 10^{11}$ | ND | ND |
| Y730F scAAV2-EGFP | $1.2 \times 10^{11}$ | $5.0 \times 10^{11}$ | $1.2 \times 10^{11}$ | $4.0 \times 10^{11}$ |

ND = Not done.

The transduction efficiency of each of the tyrosine-mutant vectors was analyzed and compared with the WT scAAV2-EGFP vector in HeLa cells in vitro under identical conditions. From the results it was evident that whereas mock-infected cells showed no green fluorescence, the transduction efficiency of each of the tyrosine-mutant vectors was significantly higher compared with the WT scAAV2-EGFP vector at 2,000 viral particles/cell. Specifically, the transduction efficiency of Y444F, Y500F, Y730F vectors was ~8-to 11-fold higher than the WT vector.

Mutations in Surface-Exposed Tyrosine Residues Dramatically Improve the Transduction Efficiency of AAV2 Vectors in Murine Hepatocytes In Vivo.

Figure 17B:
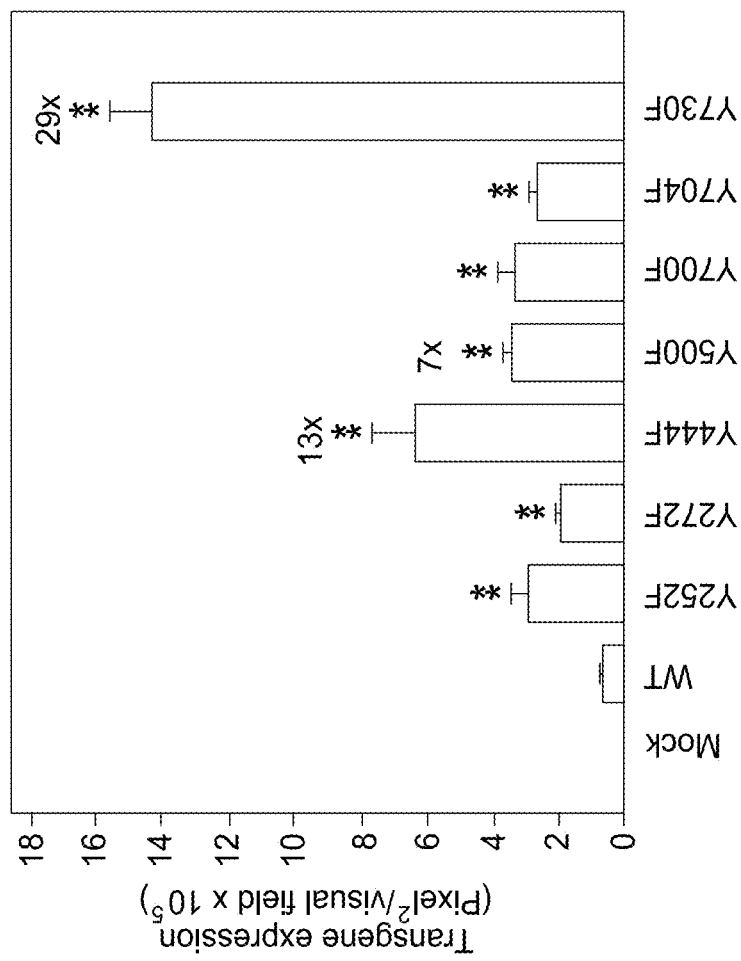
FIG. 17A and FIG. 17B show AAV2-mediated transduction of hepatocytes from normal C57BL/6 mice injected via tail vein with tyrosine-mutant capsid scAAV2-EGFP vectors.
Figure 17A:
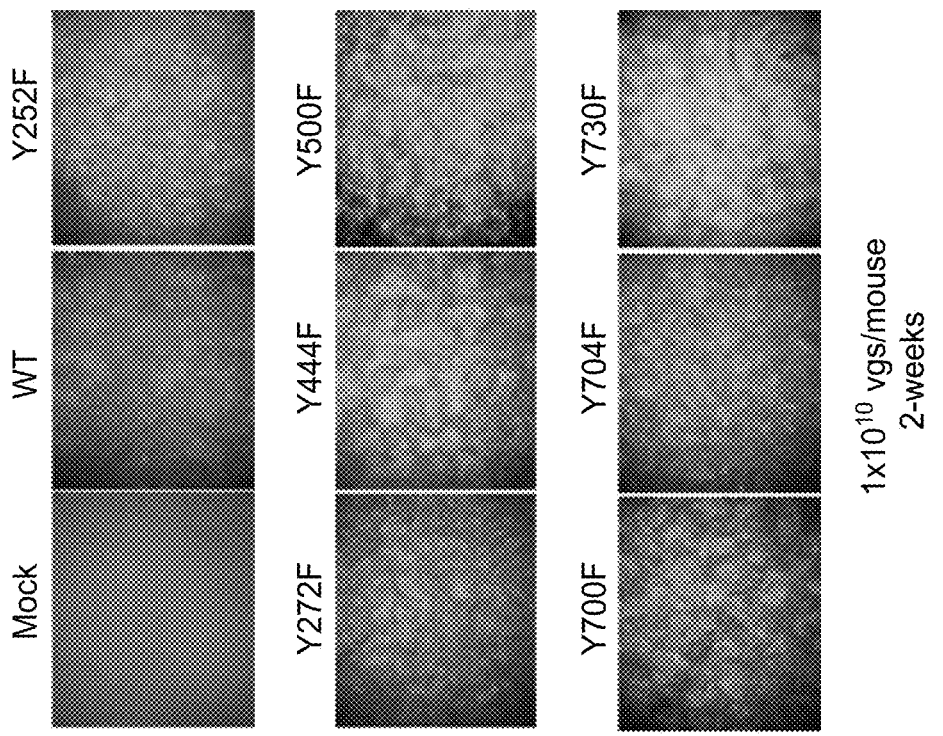

The efficacy of WT and tyrosine-mutant scAAV2-EGFP vectors was also evaluated in a mouse model in vivo. As can be seen in FIG. 17A, the transduction efficiency of tyrosine-mutant vectors was significantly higher, and ranged between 4-29-fold, compared with the WT vector (FIG. 17B). When other tissues, such as heart, lung, kidney, spleen, pancreas, GI tract (jejunum, colon), testis, skeletal muscle, and brain were harvested from mice injected with $1\times10^{10}$ particles of the tyrosine-mutant vectors and analyzed, no evidence of EGFP gene expression was seen. Thus, mutations in the surface-exposed tyrosine residues did not appear to alter the liver-tropism following tail vein injection of these vectors in vivo.

The Increased Transduction Efficiency of Tyrosine-Mutant Vectors is Due to Lack of Ubiquitination, and Improved Intracellular Trafficking to the Nucleus.

To further confirm the hypothesis that EGFR-PTK-mediated phosphorylation of capsid proteins at tyrosine residues is a pre-requisite for ubiquitination of AAV2 capsids, and that ubiquitinated virions are recognized and degraded by cytoplasmic proteasome on their way to the nucleus, leading to inefficient nuclear transport, a series of experiments were performed as follows.

In the first set of studies, HeLa C12 cells, carrying adenovirus-inducible AAV2 rep and cap genes, were mock-infected or infected with WT, Y444F or Y730F scAAV2-EGFP vectors. As shown in FIG. 18A and FIG. 18B, whereas mock-infected cells showed no green fluorescence, and ~15% of cells were transduced with the WT scAAV2-EGFP vectors in the absence of co-infection with adenovirus, the transduction efficiency of Y444F and Y730F scAAV2-EGFP vectors was increased by ~9 and ~18-fold, respectively, compared with the WT vector. Interestingly, whereas co-infection with adenovirus led to ~11-fold increase (cf. FIG. 18B), the transduction efficiency of Y444F and Y730F scAAV2-EGFP vectors was not further enhanced by co-infection with adenovirus. Since adenovirus can improve AAV2 vector nuclear transport in HeLa cells, these data suggest that the surface-exposed tyrosine residues play a role in intracellular trafficking of AAV2, and that their removal leads to efficient nuclear transport of AAV2 vectors.

In the second set of studies, HeLa cells, either mock-treated or treated with Tyr23, a specific inhibitor of EGFR-PTK, or MG132, a proteasome inhibitor, both known to increase the transduction efficiency of AAV vectors, were mock-infected or infected with the WT or Y730F scAAV2-EGFP vectors. These data are shown in FIG. 18C. Whereas mock-infected cells showed no green fluorescence, and ~5% of cells were transduced with the WT scAAV2-EGFP vectors in mock-treated cells, pretreatment with Tyr23 or MG132 led to an ~9-fold and ~6-fold increase in the transduction efficiency, respectively (FIG. 18D). Although the transduction efficiency of Y730F scAAV2-EGFP vectors was increased by ~14-fold compared with the WT vectors, it was not further enhanced by pretreatment with either Tyr23 or MG132 (FIG. 18D). These data strongly suggest that the absence of surface-exposed tyrosine residues, which prevented phosphorylation of the mutant vectors, likely prevented ubiquitination of the capsid proteins, and these vectors on their way to the nucleus could not be recognized and degraded by the proteasome, which led to their efficient nuclear translocation.

Figure 19:
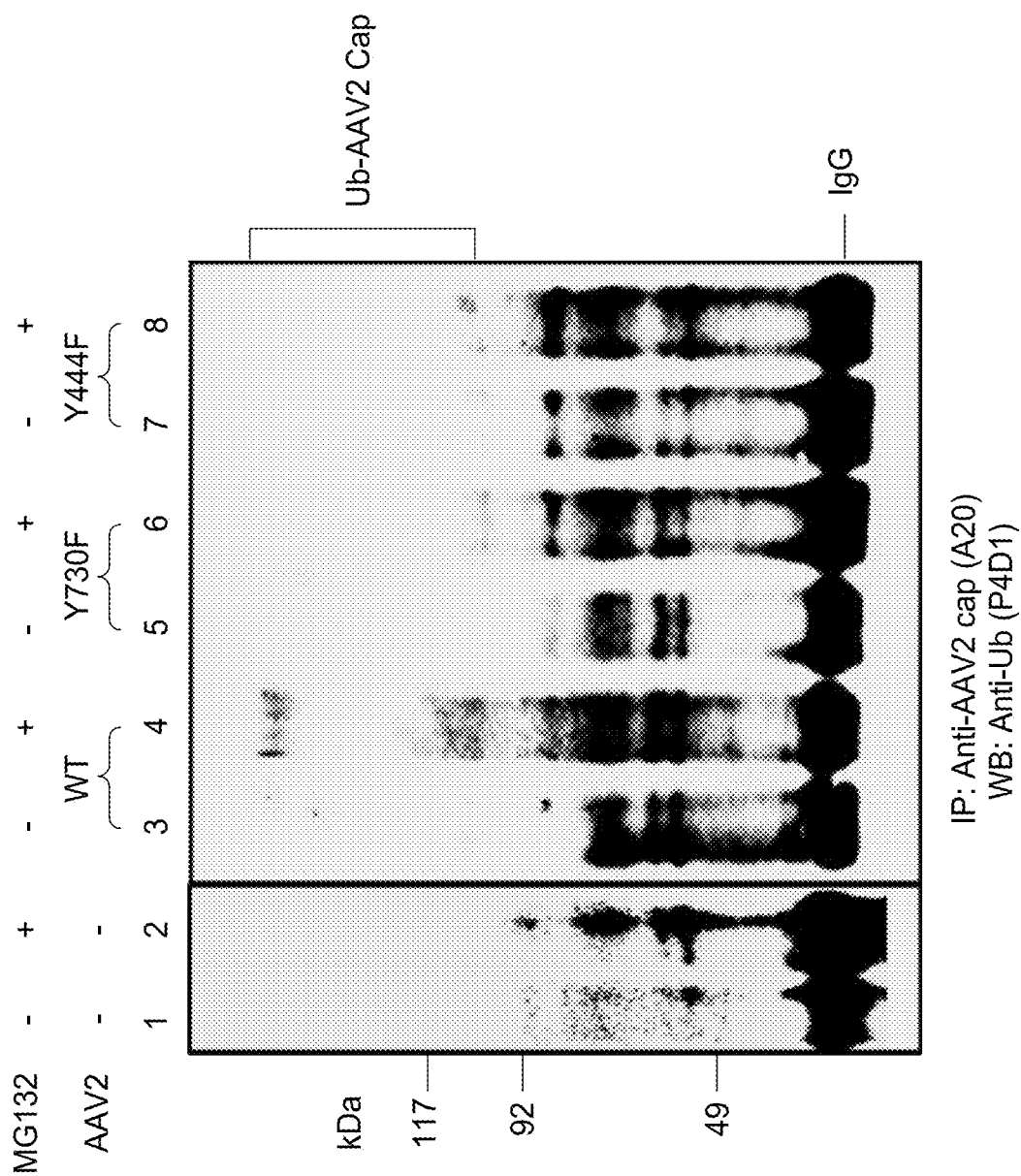
FIG. 19 illustrates a western hybridization analysis of ubiquitinated AAV2 capsid proteins in HeLa cells following transduction with tyrosine-mutant scAAV2-EGFP vectors. Whole cell lysates (WCL) prepared from cells, untreated or treated with MG132, following mock-infection (lanes 1 and 2), or infected with the WT (lanes 3 and 4), Y730F (lanes 5 and 6), or Y444F (lanes 7 and 8) scAAV2-EGFP vectors were immunoprecipitated with anti-AAV2 capsid antibody A20 followed by Western blot analyses with anti-Ub monoclonal antibody P4D1.

In the third set of studies, HeLa cells, either mock-treated or treated with MG132, were mock-infected or infected with the WT, Y730F, or Y444F scAAV2-EGFP vectors. WCL were prepared 4 hrs post-infection and equivalent amounts of proteins were immunoprecipitated first with anti-AAV2 capsid antibody (A20) followed by Western blot analyses with anti-Ub monoclonal antibody. These results are shown in FIG. 19. As can be seen, whereas ubiquitinated AAV2 capsid proteins (Ub-AAV2 Cap) were undetectable in mock-infected cells (lanes 1, 2), the signal of ubiquitinated AAV2 capsid proteins was weaker in untreated cells (lanes 3, 5), and a significant accumulation of ubiquitinated AAV2 capsid proteins occurred following treatment with MG132 (lane 4). Interestingly, infections with Y730F or Y444F vectors dramatically decreased the extent of accumulation of MG132-induced ubiquitinated AAV2 capsid proteins (lanes 6, 8). These results substantiate that mutation in tyrosine residues circumvents proteasome-mediated degradation of the vectors.

In the fourth set of studies, the fate of the input WT, Y444F, and Y730F vector viral DNA was determined in HeLa cells. Southern blot analysis of low-$M_r$ DNA samples isolated from cytoplasmic [C] and nuclear [N] fractions (FIG. 5A) and densitometric scanning of autoradiographs (FIG. 20B), revealed that ~36% of the input scAAV2 DNA was present in the nuclear fraction in cells infected with the WT vector (FIG. 20A, lane 4 and FIG. 20B), consistent with previous studies. Interestingly, however, the amount of input Y730F and Y444F scAAV2 vector DNA in the nuclear fraction was increased to ~72% and ~70%, respectively (FIG. 20B). These results further document that mutations in the surface-exposed tyrosine residues prevent ubiquitination of AAV2 capsids, resulting in a decrease of proteasome-mediated degradation, and in turn, facilitate nuclear transport of AAV2 vectors.

Tyrosine-Mutant Vectors Express Therapeutic Levels of Human Factor IX Protein at ~10-Fold Reduced Vector Dose in Mice.

It was important to examine whether tyrosine-mutant AAV2 vectors were capable of delivering a therapeutic gene efficiently at a reduced vector dose in vivo. To this end, a single-stranded, hepatocyte-specific human Factor IX (h.FIX) expression cassette was encapsidated in the Y730F vector, and the efficacy of this vector was tested in 3 different strains of mice (BALB/c, C3H/HeJ, and C57BL/6). Consistently in all 3 strains, Y730F vector achieved ~10-fold higher circulating hF.IX levels compared with the WT vector following tail vein or portal vein administration, with the latter being the more effective route. These results, shown in FIG. 21A, FIG. 21B, FIG. 21C, and FIG. 21D, clearly indicate that the Y730F vectors expressed therapeutic levels of human F.IX protein (~50 ng/ml) at ~10-fold reduced vector dose ($10^{10}$ particles/mouse) in C57BL/6 mice by port vein injection. It should be noted that hepatic viral gene transfer in C57BL/6 mice is generally more efficient than in the other two strains.

These results demonstrated here are consistent with the interpretation that EGFR-PTK-induced tyrosine phosphorylation of AAV2 capsid proteins promotes ubiquitination and degradation of AAV2, thus leading to impairment of viral nuclear transport and decrease in transduction efficiency. Mutational analyses of each of the seven surface-exposed tyrosine residues yield AAV2 vectors with significantly increased transduction efficiency in vitro as well as in vivo. Specifically, Y444F and Y730F mutant vectors bypass the ubiquitination step, which results in a significantly improved intracellular trafficking and delivery of the viral genome to the nucleus.

Despite long-term therapeutic expression achieved in preclinical animal models by AAV2 vectors composed of the WT capsid proteins, in a recent gene therapy trial, two patients with severe hemophilia B developed vector dose-dependent transaminitis that limited duration of hepatocyte-derived hF.IX expression to <8 weeks. Subsequent analyses demonstrated presence of memory $CD8^+$ T cells to AAV capsids in humans and an MHC I-restricted, capsid-specific cytotoxic T lymphocyte (CTL) response in one of the hemophilia B patients, which mirrored the time course of the transaminitis. It was concluded that this $CD8^+T$ cell response to input capsid eliminated AAV2-transduced hepatocytes. The present studies show that a lower capsid antigen dose is sufficient for efficient gene transfer with the Y730F vector. The data also show much-reduced ubiquitination of AAV-Y730F compared to WT capsid, a prerequisite for MHC I presentation. Thus, the T-cell response to AAV2 capsid (a serious hurdle for therapeutic gene transfer in the liver), may be avoided by using the surface-exposed tyrosine-mutant AAV2 vectors.

Dramatically increased transduction efficiency of tyrosine-mutant vectors have also been observed in primary human neuronal and hematopoietic stem cells in vitro and in various tissues and organs in mice in vivo. Double, triple, and quadruple tyrosine-mutants have also been constructed to examine whether such multiple mutants are viable, and whether the transduction efficiency of these vectors can be augmented further. It is noteworthy that with a few exceptions (Y444 positioned equivalent to a glycine in AAV4 and arginine in AAV5; Y700 positioned equivalent to phenylalanine in AAV4 and AAV5; and Y704 positioned equivalent to a phenylalanine in AAV7), these tyrosine residues are highly conserved in AAV serotypes 1 through 10.

Example 4—Analysis of Tyrosine Positions on the AAV2 Capsid

The following summary is a list of all Tyr residues in the structurally ordered region of VP3 (217-735):

These Tyr residues are classified based upon whether they are exposed, partially hidden, or not exposed:
Surface Exposed
  Tyr252[1]—Surface exposed—canyon floor
  Tyr272—Surface exposed—raised region between the 2- and 5-fold depressions
  Tyr444—Surface exposed—wall of 3-fold protrusions
  Tyr500—Surface exposed—wall of 3-fold protrusions
  Tyr700—Surface exposed—2-fold axis
  Tyr704[2]—Surface exposed—2-fold axis
  Tyr730—Surface exposed—2-fold axis
[1]Tyr252 has been mutated and confirmed by partial sequencing. [2]Tyr704 has been muted and completely sequenced. All others listed have also been mutated, with sequence analysis being performed to confirm each.
Surface, but Mostly Hidden Tyrosine Residues
  Tyrosine resides Tyr275, Tyr281, Tyr508, Tyr576, Tyr612, Tyr673, and Tyr720.
Not Exposed
  Tyr257, Tyr348, Tyr352, Tyr375, Tyr377, Tyr393, Tyr397, Tyr413, Tyr424, Tyr441, Tyr443, and Tyr483.

REFERENCES

The following references, to the extent that they provide exemplary procedural or other details supplementary to those set forth herein, are specifically incorporated herein by reference:

1. Berns, K I and Giraud, C, "Biology of adeno-associated virus," *Curr. Top. Microbiol. Immunol.*, 218:1-23, 1996.
2. Muzyczka, N, "Use of adeno-associated virus as a general transduction vector for mammalian cells," *Curr. Top. Microbiol. Immunol.*, 158:97-129, 1992.
3. Flotte, T, Carter, B, Conrad, C, Guggino, W, Reynolds T, Rosenstein, B, et al., "A phase I study of an adeno-associated virus-CFTR gene vector in adult CF patients with mild lung disease," *Hum. Gene Ther.,* 7:1145-1159, 1996.
4. Kay, M A, Manno, C S, Ragni, M V, Larson, R I, Couto, L B, McClelland, A, et al., "Evidence for gene transfer and expression of factor IX in haemophilia B patients treated with an AAV vector," *Nat. Genet.,* 24:257-261, 2000.
5. Flotte, T R, Brantly, M L, Spencer, L T, Byrne, B J, Spencer, C T, Baker, D J, et al., "Phase I trial of intramuscular injection of a recombinant adeno-associated virus alpha 1-antitrypsin (rAAV2-CB-hAAT) gene vector to AAT-deficient adults," *Hum. Gene Ther.,* 15:93-128, 2004.
6. Kaplitt, M G, Leone, P, Samulski, R J, Xiao, X, Pfaff, D W, O'Malley, K L, et al., "Long-term gene expression and phenotypic correction using adeno-associated virus vectors in the mammalian brain," *Nat. Genet.,* 8:148-154, 1994.
7. Xiao, X, Li, J and Samulski, R J, "Efficient long-term gene transfer into muscle tissue of immunocompetent mice by adeno-associated virus vector," *J. Virol.,* 70:8098-8108, 1996.
8. Yang, G S, Schmidt, M, Yan, Z, Lindbloom, J D, Harding, T C, Donahue, B A, et al., "Virus-mediated transduction of murine retina with adeno-associated virus: effects of viral capsid and genome size," *J. Virol.,* 76:7651-7660, 2002.
9. Summerford, C and Samulski, R J, "Membrane-associated heparan sulfate proteoglycan is a receptor for adeno-associated virus type 2 virions," *J. Virol.,* 72:1438-1445, 1998.
10. Qing, K, Mah, C, Hansen, J, Zhou, S, Dwarki, V and Srivastava, A, "Human fibroblast growth factor receptor 1 is a co-receptor for infection by adeno-associated virus 2," *Nat. Med.,* 5:71-77, 1999.
11. Summerford, C, Bartlett, J S and Samulski, R J, "AlphaVbeta5 integrin: a co-receptor for adeno-associated virus type 2 infection," *Nat. Med.,* 5:78-82, 1999.
12. Kashiwakura, Y, Tamayose, K, Iwabuchi, K, Hirai, Y, Shimada, T, Matsumoto, K, et al., "Hepatocyte growth factor receptor is a coreceptor for adeno-associated virus type 2 infection," *J. Virol.,* 79:609-614, 2005.
13. Akache, B, Grimm, D, Pandey, K, Yant, S R, Xu, H and Kay, M A, "The 37/67-kilodalton laminin receptor is a receptor for adeno-associated virus serotypes 8, 2, 3, and 9," *J. Virol.,* 80:9831-9836. 2006.
14. Hansen, J, Qing, K, Kwon, H J, Mah, C and Srivastava, A, "Impaired intracellular trafficking of adeno-associated virus type 2 vectors limits efficient transduction of murine fibroblasts," *J. Virol.,* 74:992-996, 2000.
15. Hansen, J, Qing, K and Srivastava, A, "Adeno-associated virus type 2-mediated gene transfer: altered endocytic processing enhances transduction efficiency in murine fibroblasts," *J. Virol.,* 75:4080-4090, 2001.
16. Douar, A M, Poulard, K, Stockholm, D and Danos, O, "Intracellular trafficking of adeno-associated virus vectors: routing to the late endosomal compartment and proteasome degradation," *J. Virol.,* 75:1824-1833, 2001.
17. Zhao, W, Zhong, L, Wu, J, Chen, L, Qing, K, Weigel-Kelley, K A, et al., "Role of cellular FKBP52 protein in intracellular trafficking of recombinant adeno-associated virus 2 vectors," *Virology,* 353:283-293, 2006.
18. Thomas, C E, Storm, T A, Huang, Z and Kay, M A, "Rapid uncoating of vector genomes is the key to efficient liver transduction with pseudotyped adeno-associated virus vectors," *J. Virol.,* 78:3110-3122, 2004.
19. Zhong, L, Li, W, Yang, Z, Qing, K, Tan, M, Hansen, J, et al., "Impaired nuclear transport and uncoating limit recombinant adeno-associated virus 2 vector-mediated transduction of primary murine hematopoietic cells," *Hum. Gene Ther.,* 15(12):1207-1218, December 2004.
20. Ferrari, F K, Samulski, T, Shenk, T and Samulski, R J, "Second-strand synthesis is a rate-limiting step for efficient transduction by recombinant adeno-associated virus vectors," *J. Virol.,* 70:3227-3234, 1996.
21. Fisher, K J, Gao, G P, Weitzman, M D, DeMatteo, R, Burda, J F and Wilson, J M, "Transduction with recombinant adeno-associated virus for gene therapy is limited by leading-strand synthesis," *J. Virol.,* 70:520-532, 1996.
22. Qing, K, Wang, X S, Kube, D M, Ponnazhagan, S, Bajpai, A and Srivastava, A, "Role of tyrosine phosphorylation of a cellular protein in adeno-associated virus 2-mediated transgene expression," *Proc. Natl. Acad. Sci. USA,* 94:10879-10884, 1997.
23. Qing, K, Khuntirat, B, Mah, C, Kube, D M, Wang, X S, Ponnazhagan, S, et al., "Adeno-associated virus type 2-mediated gene transfer: correlation of tyrosine phosphorylation of the cellular single-stranded D sequence-binding protein with transgene expression in human cells in vitro and murine tissues in vivo," *J. Virol.,* 72:1593-1599, 2004.
24. Qing, K, Hansen, J, Weigel-Kelley, K A, Tan, M, Zhou, S and Srivastava, A., "Adeno-associated virus type 2-mediated gene transfer: role of cellular FKBP52 protein in transgene expression," *J. Virol.,* 75(19):8968-8976, October 2001.
25. Qing, K, Li, W, Zhong, L, Tan, M, Hansen, J, Weigel-Kelley, K A, et al., "Adeno-associated virus type 2-mediated gene transfer: role of cellular T-cell protein tyrosine phosphatase in transgene expression in established cell lines in vitro and transgenic mice in vivo," *J. Virol.,* 77(4):2741-2746-2746, February 2003.
26. Zhong, L, Qing, K, Si, Y, Chen, L, Tan, M and Srivastava, A, "Heat-shock treatment-mediated increase in transduction by recombinant adeno-associated virus 2 vectors is independent of the cellular heat-shock protein 90," *J. Biol. Chem.,* 279:12714-12723, 2004.
27. Zhong, L, Li, W, Yang, Z, Chen, L, Li, Y, Qing, K et al., "Improved transduction of primary murine hepatocytes by recombinant adeno-associated virus 2 vectors in vivo," *Gene Ther.,* 11(20):1165-1169, July 2001.
28. Zhong, L, Chen, L, Li, Y, Qing, K, Weigel-Kelley, K A, Chan, R J, et al., "Self-complementary adeno-associated virus 2 (AAV)-T cell protein tyrosine phosphatase vectors as helper viruses to improve transduction efficiency of conventional single-stranded AAV vectors in vitro and in vivo," *Mol. Ther.,* 10(5):950-957, November 2004.
29. Tan, M, Qing, K, Zhou, S, Yoder, M C and Srivastava, A, "Adeno-associated virus 2-mediated transduction and erythroid lineage-restricted long-term expression of the human beta-globin gene in hematopoietic cells from homozygous beta-thalassemic mice," *Mol. Ther.,* 3:940-946, 2001.
30. Zhong, L, Li, W, Li, Y, Zhao, W, Wu, J, Li, B, et al, "Evaluation of primitive murine hematopoietic stem and progenitor cell transduction in vitro and in vivo by recombinant adeno-associated virus vector serotypes 1 through 5," *Hum. Gene Ther.,* 17:321-333, 2006.
31. Duan, D, Yue, Y, Yan, Z, Yang, J and Engelhardt, J F, "Endosomal processing limits gene transfer to polarized airway epithelia by adeno-associated virus," *J. Clin. Invest.,* 105:1573-1587, 2000.

32. Ding, W, Zhang, L N, Yeaman, C and Engelhardt, J F, "rAAV2 traffics through both the late and the recycling endosomes in a dose-dependent fashion," *Mol. Ther.,* 13:671-682, 2006.
33. Haglund, K, Sigismund, S, Polo, S, Szymkiewicz, I, Di Fiore, P P and Dikic, I, "Multiple monoubiquitination of RTKs is sufficient for their endocytosis and degradation," *Nat. Cell. Biol.,* 5:461-466, 2003.
34. Yan, Z, Zak, R, Zhang, Y, Ding, W, Godwin S, Munson, K, et al., "Distinct classes of proteasome-modulating agents cooperatively augment recombinant adeno-associated virus type 2 and type 5-mediated transduction from the apical surfaces of human airway epithelia," *J. Virol.,* 78:2863-2874, 2004.
35. Jennings, K, Miyamae T, Traister, R, Marinov, A, Katakura, S, Sowders, D, et al., "Proteasome inhibition enhances AAV-mediated transgene expression in human synoviocytes in vitro and in vivo," *Mol. Ther.,* 11:600-607, 2005.
36. Brown, K, Gerstberger, S, Carlson, L, Franzoso, G and Siebenlist, U, "Control of I kappa B-alpha proteolysis by site-specific, signal-induced phosphorylation," *Science,* 267:1485-1488, 1995.
37. Traenckner, E B, Pahl, H L, Henkel, T, Schmidt, K N, Wilk, S and Baeuerle, P A, "Phosphorylation of human I kappa B-alpha on serines 32 and 36 controls I kappa B-alpha proteolysis and N F-kappa B activation in response to diverse stimuli," *EMBO J.,* 14:2876-2883, 1995.
38. Cenciarelli, C, Wilhelm, K G Jr, Guo, A and Weissman, A M, "T cell antigen receptor ubiquitination is a consequence of receptor-mediated tyrosine kinase activation," *J. Biol. Chem.,* 271:8709-8713, 1996.
39. Paolini, R, Serra, A, Molfetta, R, Piccoli, M, Frati, L and Santoni, A, "Tyrosine kinase-dependent ubiquitination of CD16 zeta subunit in human N K cells following receptor engagement," *Eur. J. Immunol.,* 29:3179-3187, 1999.
40. Stern, K A, Visser Smit, G D, Place, T L, Winistorfer, S, Piper, R C and Lill, N L, "EGF receptor fate is controlled by Hrs tyrosine phosphorylation sites that regulate Hrs degradation," *Mol. Cell. Biol.,* 27:888-898, 2007.
41. Penrose, K J and McBride, A A, "Proteasome-mediated degradation of the papillomavirus E2-TA protein is regulated by phosphorylation and can modulate viral genome copy number," *J. Virol.,* 74:6031-6038, 2000.
42. Penrose, K J, Garcia-Alai, M, de Prat-Gay, G and McBride, A A, "Casein Kinase II phosphorylation-induced conformational switch triggers degradation of the papillomavirus E2 protein," *J. Biol. Chem.,* 279:22430-22439, 2004.
43. Mah, C, Qing, K, Khuntirat, B, Ponnazhagan, S, Wang, X S, Kube, D M, et al., "Adeno-associated virus type 2-mediated gene transfer: role of epidermal growth factor receptor protein tyrosine kinase in transgene expression," *J. Virol.,* 72:9835-9843, 1998.
44. McCarty, D M, Fu, H, Monahan, P E, Toulson, C E, Naik, P and Samulski, R J, "Adeno-associated virus terminal repeat (T R) mutant generates self-complementary vectors to overcome the rate-limiting step to transduction in vivo," *Gene Ther.,* 10:2112-2118, 2003.
45. Wang, Z, Ma, H I, Li, J, Sun, L, Zhang, J and Xiao, X, "Rapid and highly efficient transduction by double-stranded adeno-associated virus vectors in vitro and in vivo," *Gene Ther.,* 10:2105-2111, 2003.
46. Wu, J, Zhao, W, Zhong, L, Han, Z, Li, B, Ma, W, et al., "Self-complementary recombinant adeno-associated virus vectors: Packaging capacity and the role of Rep proteins in vector purity," *Hum. Gene Ther.,* 18:171-182, 2007.
47. Pickart, C M, "Mechanisms underlying ubiquitination, *Ann. Rev. Biochem.,* 70:503-533, 2001.
48. Yan, Z, Zak, R, Luxton, G W, Ritchie, T C, Bantel-Schaal, U and Engelhardt, J F, "Ubiquitination of both adeno-associated virus type 2 and 5 capsid proteins affects the transduction efficiency of recombinant vectors," *J. Virol.,* 76:2043-2053, 2002.
49. Auricchio, A, Hildinger, M, O'Connor, E, Gao, G P and Wilson, J M, "Isolation of highly infectious and pure adeno-associated virus type 2 vectors with a single-step gravity-flow column," *Hum. Gene Ther.,* 12:71-76, 2001.
50. Zhong, L and Su, J Y, "Isoflurane activates PKC and $Ca^{2+}$-calmodulin-dependent protein kinase II via MAP kinase signaling in cultured vascular smooth muscle cells," *Anesthesiology,* 96:148-154, 2002.
51. U.S. Pat. No. 4,216,209.
52. U.S. Pat. No. 4,237,244.
53. U.S. Pat. No. 4,554,101.
54. U.S. Pat. No. 4,683,195.
55. U.S. Pat. No. 4,683,202.
56. U.S. Pat. No. 4,800,159.
57. U.S. Pat. No. 4,883,750.
58. U.S. Pat. No. 4,987,071.
59. U.S. Pat. No. 5,037,746.
60. U.S. Pat. No. 5,093,246.
61. U.S. Pat. No. 5,098,887.
62. U.S. Pat. No. 5,116,742.
63. U.S. Pat. No. 5,145,684.
64. U.S. Pat. No. 5,219,727.
65. U.S. Pat. No. 5,238,921.
66. U.S. Pat. No. 5,297,721.
67. U.S. Pat. No. 5,334,711.
68. U.S. Pat. No. 5,348,978.
69. U.S. Pat. No. 5,354,855.
70. U.S. Pat. No. 5,399,346.
71. U.S. Pat. No. 5,399,363.
72. U.S. Pat. No. 5,455,166.
73. U.S. Pat. No. 5,466,468.
74. U.S. Pat. No. 5,543,158.
75. U.S. Pat. No. 5,552,157.
76. U.S. Pat. No. 5,552,397.
77. U.S. Pat. No. 5,565,213.
78. U.S. Pat. No. 5,567,434.
79. U.S. Pat. No. 5,580,579.
80. U.S. Pat. No. 5,602,306.
81. U.S. Pat. No. 5,631,359.
82. U.S. Pat. No. 5,639,655.
83. U.S. Pat. No. 5,639,940
84. U.S. Pat. No. 5,641,515
85. U.S. Pat. No. 5,646,020.
86. U.S. Pat. No. 5,646,031.
87. U.S. Pat. No. 5,648,211.
88. U.S. Pat. No. 5,656,016.
89. U.S. Pat. No. 5,697,899.
90. U.S. Pat. No. 5,712,124.
91. U.S. Pat. No. 5,720,936.
92. U.S. Pat. No. 5,725,871.
93. U.S. Pat. No. 5,738,868.
94. U.S. Pat. No. 5,741,516.
95. U.S. Pat. No. 5,744,311.
96. U.S. Pat. No. 5,756,353.
97. U.S. Pat. No. 5,770,219.
98. U.S. Pat. No. 5,779,708
99. U.S. Pat. No. 5,780,045

100. U.S. Pat. No. 5,783,208
101. U.S. Pat. No. 5,789,655.
102. U.S. Pat. No. 5,792,451.
103. U.S. Pat. No. 5,795,587.
104. U.S. Pat. No. 5,797,898.
105. U.S. Pat. No. 5,804,212.
106. U.S. Pat. No. 5,863,736.
107. Snyder R O et al. (1997) Persistent and therapeutic concentrations of human factor IX in mice after hepatic gene transfer of recombinant AAV vectors. Nat Genet 16: 270-276.
108. Snyder R O, Francis J. (2005) Adeno-associated viral vectors for clinical gene transfer studies. Curr Gene Ther 5: 311-321.
109. Sanlioglu S et al. (2000) Endocytosis and nuclear trafficking of adeno-associated virus type 2 are controlled by racl and phosphatidylinositol-3 kinase activation. J Virol 74: 9184-9196.
110. Zhong L et al. (2008) Single-polarity recombinant adeno-associated virus 2 vector-mediated transgene expression in vitro and in vivo: mechanism of transduction. Mol Ther 16: 290-295.
111. McCarty D M, Young S M, Jr., Samulski R J. (2004) Integration of adeno-associated virus (AAV) and recombinant AAV vectors. Annu Rev Genet 38: 819-845.
112. Zhong L et al. (2007) A dual role of EGFR protein tyrosine kinase signaling in ubiquitination of AAV2 capsids and viral second-strand DNA synthesis. Mol Ther 15: 1323-1330.
113. Zhong L et al. (2008) Tyrosine-Phosphorylation of AAV2 Capsid Proteins and its Consequences on Viral Intracellular Trafficking and Transgene Expression. Mol Ther: in press.
114. Xiao W, Warrington K H, Jr., Hearing P, Hughes J, Muzyczka N. (2002) Adenovirus-facilitated nuclear translocation of adeno-associated virus type 2. J Virol 76: 11505-11517.
115. Pajusola K et al. (2002) Cell-type-specific characteristics modulate the transduction efficiency of adeno-associated virus type 2 and restrain infection of endothelial cells. J Virol 76: 11530-11540.
116. Warrington K H, Jr., Herzog R W. (2006) Treatment of human disease by adeno-associated viral gene transfer. Hum Genet 119: 571-603.
117. Manno C S et al. (2006) Successful transduction of liver in hemophilia by AAV-Factor IX and limitations imposed by the host immune response. Nat Med 12: 342-347.
118. Mingozzi F et al. (2007) CD8(+) T-cell responses to adeno-associated virus capsid in humans. Nat Med 13: 419-422.
119. Auricchio A, Hildinger M, O'Connor E, Gao G P, Wilson J M. (2001) Isolation of highly infectious and pure adeno-associated virus type 2 vectors with a single-step gravity-flow column. Hum Gene Ther 12: 71-76.
120. Xie Q et al. (2002) The atomic structure of adeno-associated virus (AAV-2), a vector for human gene therapy. Proc Natl Acad Sci USA 99: 10405-10410.
121. Jones T A, Zou J Y, Cowan S W, Kjeldgaard M. (1991) Improved methods for building protein models in electron density maps and the location of errors in these models. Acta Crystallogr A 47 (Pt 2): 110-119.
122. Emsley P, Cowtan K. (2004) Coot: model-building tools for molecular graphics.
123. Acta Crystallogr D Biol Crystallogr 60: 2126-2132.
124. Wang W, Malcolm B A. (1999) Two-stage PCR protocol allowing introduction of multiple mutations, deletions and insertions using QuikChange Site-Directed Mutagenesis. Biotechniques 26: 680-682.
125. Mingozzi F et al. (2003) Induction of immune tolerance to coagulation factor IX antigen by in vivo hepatic gene transfer. J Clin Invest 111: 1347-1356.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A modified adeno associated virus (AAV) capsid protein comprising a non-tyrosine amino acid at one or more positions that correspond to Tyr252, Tyr272, Tyr275, Tyr281, Tyr444, Tyr500, Tyr508, Tyr612, Tyr704, Tyr720, Tyr730, or Tyr673 in a wild-type AAV2 capsid protein.

2. The modified AAV capsid protein according to claim 1, wherein the non-tyrosine amino acid is a phenylalanine.

3. The modified AAV capsid protein according to claim 1, wherein the capsid protein is of a serotype selected from the group consisting of an AAV serotype 1, an AAV serotype 2, an AAV serotype 3, an AAV serotype 4, an AAV serotype 5 and an AAV serotype 6.

4. The modified AAV capsid protein according to claim 1, wherein the capsid protein is comprised within an AAV particle.

5. A recombinant adeno-associated viral (rAAV) particle that comprises the modified AAV capsid protein according to claim 1.

6. The rAAV particle of claim 5, that is of a serotype selected from AAV1, AAV2, AAV3, AAV4, AAV5 and AAV6.

7. The rAAV particle according to claim 5, further comprising at least a first nucleic acid segment that encodes a therapeutic agent operably linked to a promoter capable of expressing said segment in a host cell.

8. The rAAV particle according to claim 7, further comprising an enhancer sequence operably linked to said nucleic acid segment.

9. The rAAV particle according to claim 8, wherein the enhancer sequence is selected from the group consisting of a CMV enhancer, a synthetic enhancer, a liver-specific enhancer, a vascular-specific enhancer, a brain-specific enhancer, a neural cell-specific enhancer, a lung-specific enhancer, a muscle-specific enhancer, a kidney-specific enhancer, a pancreas-specific enhancer, and an islet cell-specific enhancer.

10. The rAAV particle according to claim 7, wherein said promoter is a heterologous, tissue-specific, constitutive or inducible promoter.

11. The rAAV particle according to claim 10, wherein said promoter is selected from the group consisting of a CMV promoter, a β-actin promoter, an insulin promoter, an enolase promoter, a BDNF promoter, an NGF promoter, an EGF promoter, a growth factor promoter, an axon-specific promoter, a dendrite-specific promoter, a brain-specific promoter, a hippocampal-specific promoter, a kidney-specific promoter, an elafin promoter, a cytokine promoter, an interferon promoter, a growth factor promoter, an alpha-1 antitrypsin promoter, a brain-specific promoter, a neural cell-specific promoter, a central nervous system cell-specific promoter, a peripheral nervous system cell-specific promoter, an interleukin promoter, a serpin promoter, a hybrid CMV promoter, a hybrid β-actin promoter, an EF1 promoter, a U1a promoter, a U1b promoter, a Tet-inducible promoter and a VP16-LexA promoter.

12. The rAAV particle according to claim 7, wherein the therapeutic agent is selected from the group consisting of a polypeptide, a peptide, an antibody, an antigen binding fragment, a ribozyme, a peptide nucleic acid, an siRNA, an RNAi, an antisense oligonucleotide and an antisense polynucleotide.

13. A composition comprising the rAAV particle according to claim 5.

14. A method for administering a therapeutic or a diagnostic agent to a mammal in need thereof, the method comprising: providing to at least a first cell, tissue or organ of the mammal the composition according to claim 13, wherein the transduction efficiency of the rAAV particle comprised in the composition is higher than that of a particle comprising a corresponding, unmodified, wild-type capsid protein.

15. The method of claim 14, wherein the rAAV particle is a serotype selected from AAV1, AAV2, AAV3, AAV4, AAV5 and AAV6.

16. The method according to claim 14, wherein the transduction efficiency of the rAAV particle comprising the modified capsid protein is at least 4-fold higher than that of a rAAV particle comprising the corresponding, unmodified capsid protein.

17. The method according to claim 14, wherein the non-tyrosine amino acid is a phenylalanine.

18. The method according to claim 14, wherein the rAAV particle further comprises a polynucleotide that encodes a therapeutic agent operably linked to a promoter.

19. The method according to claim 14, wherein the rAAV particle is comprised within a mammalian host cell.

20. The method according to claim 19, wherein the mammalian host cell is a human endothelial, epithelial, vascular, liver, lung, heart, pancreas, intestinal, kidney, muscle, bone, neural, blood, or brain cell.

21. A method of providing a therapeutic peptide, polypeptide, or RNA to a mammal in need thereof, the method comprising:
introducing into a selected population of cells of the mammal an effective amount of a recombinant adeno-associated viral (rAAV) particle according to claim 5;
wherein the rAAV particle comprises a nucleic acid segment that encodes the therapeutic peptide, polypeptide, or RNA, and is operably linked to at least one promoter that expresses the nucleic acid segment in one or more cells of the selected population.

22. The method of claim 21, wherein the rAAV particle is a serotype selected from AAV1, AAV2, AAV3, AAV4, AAV5 and AAV6.

23. The method according to claim 21, wherein the therapeutic peptide or polypeptide is an antibody or an antigen-binding fragment thereof; or wherein the therapeutic RNA is a ribozyme, a peptide-nucleic acid, an siRNA, an RNAi, or an antisense oligonucleotide.

24. The method according to claim 21, wherein the nucleic acid segment is further operably linked to at least one enhancer sequence.

25. The method according to claim 21, wherein the promoter is a heterologous promoter, a tissue-specific promoter, a constitutive promoter, a cell-specific promoter, an inducible promoter, or any combination thereof.

26. The method of claim 21, wherein the selected population of cells is a population of human endothelial, epithelial, vascular, liver, lung, heart, pancreas, intestinal, kidney, muscle, bone, neural, blood, or brain cell.

27. The method according to claim 21, wherein the therapeutic peptide, polypeptide, or RNA, is expressed in one or more cells of the selected population in an amount, and for a time sufficient to treat or ameliorate at least one symptom of a disease, a disorder, a dysfunction, an injury, or trauma in a human patient.

28. The method according to claim 21, wherein the mammal has cancer, diabetes, autoimmune disease, kidney disease, cardiovascular disease, pancreatic disease, intestinal disease, liver disease, neurological disease, neuromuscular disease, Bratten's disease, Alzheimer's disease, Huntington disease, Parkinson's disease, pulmonary disease, an a-1 antitrypsin deficiency, neurological disability, neuromotor deficit, neuroskeletal impairment, ischemia, stroke, or any combination thereof.

29. A method of treating or ameliorating one or more symptoms of a disease, a disorder, a dysfunction, an injury, or trauma in a mammal, comprising administering to the mammal an effective amount of the recombinant adeno-associated viral (rAAV) particle according to claim 5; wherein the particle comprises a nucleic acid segment that encodes a therapeutic peptide, polypeptide, or RNA, operably linked to at least one promoter that expresses the nucleic acid segment in one or more cells of the selected population.

30. The method of claim 29, wherein the rAAV particle is a serotype selected from AAV1, AAV2, AAV3, AAV4, AAV5 and AAV6.

31. The method according to claim 29, wherein the one or more cells are human endothelial, epithelial, vascular, liver, lung, heart, pancreas, intestinal, kidney, muscle, bone, neural, blood, or brain cells.

* * * * *

UNITED STATES PATENT AND TRADEMARK OFFICE
CERTIFICATE OF CORRECTION

PATENT NO. : 10,723,768 B2
APPLICATION NO. : 15/680668
DATED : July 28, 2020
INVENTOR(S) : Li Zhong et al.

Page 1 of 1

It is certified that error appears in the above-identified patent and that said Letters Patent is hereby corrected as shown below:

In the Claims

At Column 53, Claim 15, Line 49, the text:
"AAVS and AAV6" should be replaced with --AAV5 and AAV6--

At Column 54, Claim 26, Line 31, the text:
"neural, blood, or brain cell." should be replaced with --neural, blood, or brain cells.--

At Column 54, Claim 28, Line 44, the text:
"a-1 antitrypsin deficiency," should be replaced with --α-1 antitrypsin deficiency,--

Signed and Sealed this
Fifth Day of January, 2021

Andrei Iancu
*Director of the United States Patent and Trademark Office*

SEQUENCE LISTING

```
<160> NUMBER OF SEQ ID NOS: 7

<210> SEQ ID NO 1
<211> LENGTH: 45
<212> TYPE: DNA
<213> ORGANISM: Artificial Sequence
<220> FEATURE:
<223> OTHER INFORMATION: Primer

<400> SEQUENCE: 1
ccctgcccac cttcaacaac cacctgtaca aacaaatttc cagcc              45

<210> SEQ ID NO 2
<211> LENGTH: 42
<212> TYPE: DNA
<213> ORGANISM: Artificial Sequence
<220> FEATURE:
<223> OTHER INFORMATION: Primer

<400> SEQUENCE: 2
```

```
ccaatcagga gcttcgaacg acaatcactt ctttggctac ag                                42

<210> SEQ ID NO 3
<211> LENGTH: 42
<212> TYPE: DNA
<213> ORGANISM: Artificial Sequence
<220> FEATURE:
<223> OTHER INFORMATION: Primer

<400> SEQUENCE: 3
cgaccagtac ctgtatttct taagcagaac aaacactcca ag                                42

<210> SEQ ID NO 4
<211> LENGTH: 41
<212> TYPE: DNA
<213> ORGANISM: Artificial Sequence
<220> FEATURE:
<223> OTHER INFORMATION: Primer

<400> SEQUENCE: 4
caacaacagt gaattctcgt ggaccggtgc taccaagtac c                                 41

<210> SEQ ID NO 5
<211> LENGTH: 42
<212> TYPE: DNA
<213> ORGANISM: Artificial Sequence
<220> FEATURE:
<223> OTHER INFORMATION: Primer

<400> SEQUENCE: 5
ggaatcccga aattcagttc acttcgaact acaacaagtc tg                                42

<210> SEQ ID NO 6
<211> LENGTH: 42
<212> TYPE: DNA
<213> ORGANISM: Artificial Sequence
<220> FEATURE:
<223> OTHER INFORMATION: Primer

<400> SEQUENCE: 6
ggaatcccga aattcagtac acttcgaact tcaacaagtc tg                                42

<210> SEQ ID NO 7
<211> LENGTH: 37
<212> TYPE: DNA
<213> ORGANISM: Artificial Sequence
<220> FEATURE:
<223> OTHER INFORMATION: Primer

<400> SEQUENCE: 7
cctcgcccca ttggtaccag attcctgact cgtaatc                                      37
```